US012747433B2

(12) United States Patent
Cargill et al.

(10) Patent No.: US 12,747,433 B2
(45) Date of Patent: Sep. 29, 2026

(54) METHODS AND COMPOSITIONS FOR GENERATING DOMINANT BRACHYTIC ALLELES USING GENOME EDITING

(71) Applicant: Monsanto Technology LLC, St. Louis, MO (US)

(72) Inventors: Edward J. Cargill, Chesterfield, MO (US); Linda A. Rymarquis, High Ridge, MO (US); Michelle Valentine, Troy, MO (US)

(73) Assignee: Monsanto Technology LLC, St. Louis, MO (US)

( * ) Notice: Subject to any disclaimer, the term of this patent is extended or adjusted under 35 U.S.C. 154(b) by 92 days.

(21) Appl. No.: 18/866,453

(22) PCT Filed: May 15, 2023

(86) PCT No.: PCT/US2023/066999
§ 371 (c)(1),
(2) Date: Nov. 15, 2024

(87) PCT Pub. No.: WO2023/225475
PCT Pub. Date: Nov. 23, 2023

(65) Prior Publication Data

US 2025/0320264 A1 Oct. 16, 2025

Related U.S. Application Data

(60) Provisional application No. 63/343,511, filed on May 18, 2022.

(51) Int. Cl.
*C07K 14/415* (2006.01)
*C12N 15/82* (2006.01)

(52) U.S. Cl.
CPC ........ *C07K 14/415* (2013.01); *C12N 15/8213* (2013.01); *C12N 15/8262* (2013.01); *C12N 15/8271* (2013.01)

(58) Field of Classification Search
None
See application file for complete search history.

(56) References Cited

U.S. PATENT DOCUMENTS

| | | | |
|---|---|---|---|
| 4,368,592 | A | 1/1983 | Welch |
| 5,159,135 | A | 10/1992 | Umbeck |
| 5,188,958 | A | 2/1993 | Moloney et al. |
| 5,322,938 | A | 6/1994 | McPherson et al. |
| 5,352,605 | A | 10/1994 | Fraley et al. |
| 5,463,174 | A | 10/1995 | Moloney et al. |
| 5,510,474 | A | 4/1996 | Quail et al. |
| 5,538,880 | A | 7/1996 | Lundquist et al. |
| 5,550,318 | A | 8/1996 | Adams et al. |
| 5,591,616 | A | 1/1997 | Hiei et al. |
| 5,641,876 | A | 6/1997 | McElroy et al. |
| 5,750,871 | A | 5/1998 | Moloney et al. |
| 5,824,877 | A | 10/1998 | Hinchee et al. |
| 5,850,019 | A | 12/1998 | Maiti et al. |
| 5,939,539 | A | 8/1999 | Lange et al. |
| 6,153,812 | A | 11/2000 | Fry et al. |
| 6,160,208 | A | 12/2000 | Lundquist et al. |
| 6,198,021 | B1 | 3/2001 | Lange et al. |
| 6,372,211 | B1 | 4/2002 | Isaac et al. |
| 6,380,467 | B1 | 4/2002 | Duclos |
| 6,384,301 | B1 | 5/2002 | Martinell et al. |
| 6,399,861 | B1 | 6/2002 | Anderson et al. |
| 6,420,547 | B1 | 7/2002 | Maiti et al. |
| 6,429,357 | B1 | 8/2002 | McElroy et al. |
| 6,723,897 | B2 | 4/2004 | Brown et al. |
| 6,765,133 | B2 | 7/2004 | Koehring |
| 7,041,874 | B2 | 5/2006 | Johal et al. |
| 7,049,490 | B2 | 5/2006 | Tanaka et al. |
| 7,057,088 | B2 | 6/2006 | Tanaka et al. |

(Continued)

FOREIGN PATENT DOCUMENTS

| | | |
|---|---|---|
| CN | 101440374 | 5/2009 |
| CN | 102149821 | 8/2011 |

(Continued)

OTHER PUBLICATIONS

Lai Wei et. al., A new allele of the Brachytic2 gene in maize can efficiently modify plant architecture, Heredity (2018) 121:75-86 (Year: 2018).*

Shannon A. Bage et. al., Genetic characterization of novel and CRISPR-Cas9 gene edited maize brachytic 2 alleles, Plant Gene 21 (2020) 200198, pp. 1-7 (Year: 2020).*

Oikawa, et al., "A role of OsGA20ox1, encoding an isoform of gibberellin 20-oxidase, for regulation of plant stature in rice," Plant Molecular Biology, 55:687-700 (2004).

Ookawa, et al., "Precise estimation of genomic regions controlling lodging resistance using a set of reciprocal chromosome segment substitution lines in rice," Scientific Reports, 6(30572) pp. 1-12 (2016).

Parizotto, et al., "In vivo investigation of the transcription, processing, endonucleolytic activity, and functional relevance of the spatial distribution of a plant miRNA," Genes & Development, 18:2237-2242 (2004).

(Continued)

*Primary Examiner* — Weihua Fan
*Assistant Examiner* — Yanxin Shen
(74) *Attorney, Agent, or Firm* — Dentons US LLP; David Lanzotti

(57) ABSTRACT

The present disclosure provides compositions and methods for altering auxin accumulation in corn or maize plants. Methods and compositions are also provided for altering the expression of genes related to auxin efflux through editing or mutagenesis of a brachytic2 (br2) gene to introduce a premature stop codon or a deletion into the gene such that a truncated Br2 protein encoded by the mutant allele of the br2 gene, which may be a dominant or semi-dominant allele, has at least part of a transmembrane domain without a nucleotide binding domain or motif. Modified plant, plant parts and cells having such a mutant allele with reduced or altered expression or activity of a br2 gene product can have improved characteristics, such as reduced plant height and increased lodging resistance, but without off-types in the plant.

20 Claims, 1 Drawing Sheet

Specification includes a Sequence Listing.

(56) References Cited

U.S. PATENT DOCUMENTS

| | | | |
|---|---|---|---|
| 7,138,567 | B2 | 11/2006 | Okawa et al. |
| 7,154,028 | B2 | 12/2006 | Tanaka et al. |
| 7,597,055 | B2 | 10/2009 | Choulet |
| 8,835,353 | B2 | 9/2014 | Fugiel et al. |
| 8,843,283 | B2 | 9/2014 | Strelioff et al. |
| 9,012,722 | B2 | 4/2015 | Narva et al. |
| 9,040,774 | B2 | 5/2015 | Ivashuta et al. |
| 9,303,919 | B2 | 4/2016 | Hultgren |
| 9,309,512 | B2 | 4/2016 | Allen et al. |
| 9,845,479 | B2 | 12/2017 | Beghyn et al. |
| 10,123,473 | B2 | 11/2018 | Cavender-Bares et al. |
| 10,472,684 | B2 | 11/2019 | Barten et al. |
| 10,724,047 | B2 | 7/2020 | Allen et al. |
| 10,881,057 | B2 | 1/2021 | Cannon et al. |
| 11,627,736 | B2 | 4/2023 | Barten et al. |
| 11,632,921 | B2 | 4/2023 | Cannon et al. |
| 12,492,408 | B2 | 12/2025 | Cannon et al. |
| 12,527,250 | B2 | 1/2026 | Cannon et al. |
| 2002/0053095 | A1 | 5/2002 | Brown et al. |
| 2002/0162142 | A1 | 10/2002 | Johal et al. |
| 2003/0172409 | A1 | 9/2003 | Horn |
| 2003/0233679 | A1 | 12/2003 | Brown et al. |
| 2004/0053411 | A1 | 3/2004 | Cullen et al. |
| 2004/0121321 | A1 | 6/2004 | Brown et al. |
| 2004/0268441 | A1 | 12/2004 | Vance et al. |
| 2005/0037988 | A1 | 2/2005 | Zamore et al. |
| 2005/0064474 | A1 | 3/2005 | Umov et al. |
| 2005/0144669 | A1 | 6/2005 | Reinhart et al. |
| 2005/0197253 | A1 | 9/2005 | Stoller et al. |
| 2005/0251883 | A1 | 11/2005 | Amasino et al. |
| 2006/0200878 | A1 | 9/2006 | Lutfiyya et al. |
| 2006/0253933 | A1 | 11/2006 | Brown et al. |
| 2007/0174931 | A1 | 7/2007 | Brown et al. |
| 2007/0294789 | A1 | 12/2007 | Ghiglione et al. |
| 2008/0034453 | A1 | 2/2008 | Cheikh et al. |
| 2009/0031441 | A1 | 1/2009 | Matsuoka et al. |
| 2009/0070898 | A1 | 3/2009 | Allen et al. |
| 2009/0117617 | A1 | 5/2009 | Holmes et al. |
| 2009/0313725 | A1 | 12/2009 | Yu et al. |
| 2010/0095406 | A1 | 4/2010 | Yu et al. |
| 2010/0107283 | A1 | 4/2010 | Dasgupta et al. |
| 2011/0004958 | A1 | 1/2011 | Aloni et al. |
| 2011/0035839 | A1 | 2/2011 | Lutfiyya et al. |
| 2011/0126310 | A1 | 5/2011 | Feng et al. |
| 2011/0145940 | A1 | 6/2011 | Voytas et al. |
| 2011/0167517 | A1 | 7/2011 | Danilevskaya et al. |
| 2011/0185456 | A1 | 7/2011 | Cheikh et al. |
| 2011/0296555 | A1 | 12/2011 | Ivashuta et al. |
| 2011/0301073 | A1 | 12/2011 | Gregory et al. |
| 2012/0142062 | A1 | 6/2012 | Doyon et al. |
| 2012/0174260 | A1 | 7/2012 | Narva et al. |
| 2012/0216318 | A1 | 8/2012 | La Rosa et al. |
| 2012/0297501 | A1 | 11/2012 | Beghyn et al. |
| 2013/0117869 | A1 | 5/2013 | Duchateau et al. |
| 2013/0121101 | A1 | 5/2013 | Ochampaugh et al. |
| 2013/0260012 | A1 | 10/2013 | Rommens et al. |
| 2013/0283461 | A1 | 10/2013 | Abad et al. |
| 2013/0345937 | A1 | 12/2013 | Strelioff et al. |
| 2014/0013464 | A1 | 1/2014 | Davie |
| 2014/0074360 | A1 | 3/2014 | Rosa et al. |
| 2014/0165228 | A1 | 6/2014 | Danilevskaya et al. |
| 2014/0344996 | A1 | 11/2014 | Inze et al. |
| 2015/0052634 | A1 | 2/2015 | Park et al. |
| 2015/0201619 | A1 | 7/2015 | Annigeri et al. |
| 2015/0247154 | A1 | 9/2015 | Ivashuta et al. |
| 2015/0307889 | A1 | 10/2015 | Petolino et al. |
| 2015/0376641 | A1 | 12/2015 | Etzioni et al. |
| 2016/0010109 | A1 | 1/2016 | Albertsen et al. |
| 2016/0017349 | A1 | 1/2016 | Ayele et al. |
| 2016/0046956 | A1 | 2/2016 | Yu et al. |
| 2016/0050865 | A1 | 2/2016 | Morse et al. |
| 2016/0050920 | A1 | 2/2016 | Ott et al. |
| 2016/0076046 | A1 | 3/2016 | Alexandrov et al. |
| 2016/0319375 | A1 | 11/2016 | Barten et al. |
| 2017/0079224 | A1 | 3/2017 | Jolliffe et al. |
| 2018/0051295 | A1 | 2/2018 | Allen et al. |
| 2019/0014730 | A1 | 1/2019 | Dong et al. |
| 2019/0014731 | A1 | 1/2019 | Ovadya et al. |
| 2019/0241903 | A1 | 8/2019 | Ellis et al. |
| 2019/0246586 | A1 | 8/2019 | Cannon et al. |
| 2019/0246619 | A1 | 8/2019 | Barten et al. |
| 2020/0140874 | A1 | 5/2020 | Barten et al. |
| 2021/0032649 | A1 | 2/2021 | Manjunath et al. |
| 2022/0159905 | A1 | 5/2022 | Barten et al. |
| 2022/0159919 | A1 | 5/2022 | Cannon et al. |
| 2022/0162632 | A1 | 5/2022 | Barten et al. |
| 2022/0364108 | A1 | 11/2022 | Allen et al. |
| 2023/0110884 | A1 | 4/2023 | Allen et al. |
| 2023/0292733 | A1 | 9/2023 | Barten et al. |
| 2023/0323381 | A1 | 10/2023 | Cannon et al. |
| 2026/0015625 | A1 | 1/2026 | Cannon et al. |
| 2026/0144184 | A1 | 5/2026 | Cannon et al. |

FOREIGN PATENT DOCUMENTS

| | | | | |
|---|---|---|---|---|
| CN | 102174519 | | 9/2011 | |
| CN | 111778265 | | 10/2020 | |
| EP | 1398382 | B1 | 11/2005 | |
| JP | 3829157 | B2 | 10/2006 | |
| KR | 20150045611 | | 4/2015 | |
| RU | 2013135491 | | 2/2015 | |
| RU | 2013151447 | | 5/2015 | |
| WO | 199428141 | | 12/1994 | |
| WO | 199909174 | | 2/1999 | |
| WO | 199966029 | A2 | 12/1999 | |
| WO | 2000009722 | A2 | 2/2000 | |
| WO | 2002055725 | A2 | 7/2002 | |
| WO | 2003008540 | A2 | 1/2003 | |
| WO | 2004092390 | | 10/2004 | |
| WO | 2006032916 | A2 | 3/2006 | |
| WO | 2007134234 | | 11/2007 | |
| WO | 2008034648 | | 3/2008 | |
| WO | 2010002984 | | 1/2010 | |
| WO | 2011023537 | | 3/2011 | |
| WO | 2013037959 | | 3/2013 | |
| WO | 2013086499 | A2 | 6/2013 | |
| WO | 2014055477 | A2 | 4/2014 | |
| WO | 2014151749 | | 9/2014 | |
| WO | 2015168124 | | 11/2015 | |
| WO | 2016176286 | A1 | 11/2016 | |
| WO | 2017011791 | A1 | 1/2017 | |
| WO | 2018035354 | A1 | 2/2018 | |
| WO | WO-2018119225 | A1 * | 6/2018 | ......... C12N 15/8261 |
| WO | 2018129302 | A1 | 7/2018 | |
| WO | 2019161143 | A1 | 8/2019 | |
| WO | 2019161145 | A2 | 8/2019 | |
| WO | 2019161149 | A1 | 8/2019 | |

OTHER PUBLICATIONS

Peiffer, et al., "The Genetic Architecture of Maize Height," Genetics, 196(4):1337-1356 (2014).

Peng, et al., "'Green revolution' genes encode mutant gibberellin response modulators," Nature, 400:256-261 (1999).

Petti, et al., "Mapping of a Cellulose-Deficient Mutant Named dwarf1-1 in Sorghum bicolor to the Green Revolution Gene gibberellin20-oxidase Reveals a Positive Regulatory Association between Gibberellin and Cellulose Biosynthesis," Plant Physiology, 169(1):705-716 (2015).

Plackett, et al., "Analysis of the Developmental Roles of the *Arabidopsis gibberellin* 20-Oxidases Demonstrates That GA200x1, -2, and -3 Are the Dominant Paralogs," The Plant Cell, 24(3):941-960 (2012).

Qiao, et al., "Alteration of rice growth and development via antisense expression of OsGA20ox2 gene," African Journal of Biotechnology, 12(5):3898-3904 (2013).

Qiao, et al., "Modification of plant height via RNAi suppression of OsGA20ox2 gene in rice," Euphytica, 158-35-45 (2007).

Reynolds, et al., "Rational siRNA design for RNA interference," Nature Biotechnology, 22(3):326-330 (2004).

Rhoades, et al., "Prediction of Plant MicroRNA Targets," Cell, 110(4):513-520 (2002).

(56) References Cited

OTHER PUBLICATIONS

Rieu, et al., "The gibberellin biosynthetic genes AtGA20ox1 and AtGA20ox2 act, partially redundantly, to promote growth and development throughout the *Arabidopsis* life cycle," The Plant Journal, 53 :488-504 (2008).
Ross, et al., "Gibberellin mutants," Physiologia Plantarum, 100(3):550-560 (1997).
Sarkar, et al., "Relationship between gibberellins, height, and stress tolerance in barley (*Hordeum vulgare* L.) seedlings," Plant Growth Regulation, 42:125-135 (2004).
Sasaki, et al., "A mutant gibberellin-synthesis gene in rice," Nature, 416:701-702 (2002).
Russian Search Report dated Jun. 24, 2021, in Russian Patent Application 2019105536, and English translation of the same (pp. 1-4).
Singh, "The green revolution and the evolution of agricultural education and research in India," Genome, 42 (4):557-561 (1999).
Song, et al., "Association of the molecular regulation of ear leaf senescence/stress response and photosynthesis/metabolism with heterosis at the reproductive stage in maize," Scientific Reports, 6: 29843 (2016).
Song, et al., "Flowering time regulation: photoperiod- and temperature-sensing in leaves," Trends in Plant Science, 18(10):575-583 (2013).
Song, et al., "Genome-wide identification of gibberellins metabolic enzyme genes and expression profiling analysis during seed germination in maize," Gene, 482(1-2):34-42 (2011).
Spielmeyer, et al., "Semidwarf (sd-1), "green revolution" rice, contains a defective gibberellin 20-oxidase gene," PNAS, 99(13):9043-9048 (2002).
Sun, "Gibberellin Metabolism, Perception and Signaling Pathways in *Arabidopsis*," The *Arabidopsis* Book, 2008(6): pp. 1-28 (2008).
Sunkar, et al., "Novel and Stress-Regulated MicroRNAs and Other Small RNAs from *Arabidopsis*," Plant Cell, 16 (8):2001-2019 (2004).
Supplementary Partial European Search Report dated Jan. 14, 2020, in European Patent Application No. 17842139.2.
Svitashev, et al., "Targeted Mutagenesis, Precise Gene Editing, and Site-Specific Gene Insertion in Maize Using Cas9 and Guide RNA," Plant Physiology, 169(2):931-945 (2015).
Teng, et al., "ZmGA3ox2, a candidate gene for a major QTL, qPH3.1, for plant height in maize," The Plant Journal, 73 (3):405-416 (2013).
Tollenaar, et al., "Effect of Defoliation on Kernel Development in Maize," Canadian Journal of Plant Science, 58 (1):207-212 (1978).
Tong, et al., "Reply: Brassinosteroid Regulates Gibberellin Synthesis to Promote Cell Elongation in Rice: Critical Comments on Ross and Quittenden's Letter," The Plant Cell, vol. 28, pp. 833-835, (2016).
Traore, et al., "Bt and Non-Bt Maize Growth and Development as Affected by Temperature and Drought Stress," Agronomy Journal, 92(5): 1027-1035 (2000).
Unterholzner, et al., "Reply: Interaction Between Brassinosteroids and Gibberellins: Synthesis or Signaling? In *Arabidopsis* Both!," The Plant Cell, vol. 28, pp. 836-839, (2016).
Urakami, et al., "Immunomodulation of gibberellin biosynthesis using an anti-precursor gibberellin antibody confers gibberellin-deficient phenotypes," Planta, 228:863-873 (2008).
Voytas, "Plant Genome Engineering with Sequence-Specific Nucleases," Annual Review of Plant Biology, 64:327-50 (2013).
Wang, et al., "Gibberellin Biosynthetic Deficiency Is Responsible for Maize Dominant Dwarf11 (D11) Mutant Phenotype: Physiological and Transcriptomic Evidence," PLoS One, 8(6):e66466:1-8 (2013).
Wang, et al., "More than meets the eye? Factors that affect target selection by plant miRNAs and heterochromatic siRNAs," Current Opinion Plant Biology, 27:118-124 (2015).
Wu, et al., "Target specificity of the CRISPR-Cas9 system," Quantitative Biology, 2(2):59-70 (2014).
Xiao, et al., "Dissection of GA 20-oxidase members affecting tomato morphology by RNAi-mediated silencing," Plant Growth Regulation, 50:179-189 (2006).
Yamaguchi, et al., "Gibberellin Acts Positively Then Negatively to Control Onset of Flower Formation in *Arabidopsis*," Science, 344(6184):638-641 (2014).
Yamaguchi, "Gibberellin Metabolism and its Regulation," Annual Review of Plant Biology, 59:225-251 (2008).
Yanik, et al., "TALE-Pvull Fusion Proteins—Novel Tools for Gene Targeting," PLoS One, 8(12):e82539 pp. 1-13 (2013).
Yin, et al., "In-Season Prediction of Com Yield Using Plant Height under Major Production Systems," Agronomy Journal, 103(3):923-929 (2011).
Yoshikawa, et al., "A pathway for the biogenesis of trans-acting siRNAs in *Arabidopsis*," Genes & Development, 19:2164-2175 (2005).
Zeng, et al., "Both Natural and Designed Micro RNAs Can Inhibit the Expression of Cognate mRNAs When Expressed in Human Cells," Molecular Cell, 9(6): 1327-1333 (2002).
Invitation to Pay Additional Fees for Application No. PCT/US23/62985, mailed May 23, 2023.
Klahre, et al. "High molecular weight RNAs and small interfering RNAs induce systemic posttranscriptional gene silencing in plants." Proc. Natl. Acad. Sci. U.S.A., 99 (18) 11981-11986, (2002).
Hill and Furrow, "Pinch or Push Your Corn: Scouting for Lodging Potential", University of Illinois Urbana-Champaign, Illinois Extension, Sep. 12, 2016, 2 pages.
Cox, et al., "Row Spacing, Hybrid, and Plant Density Effects on Corn Silage Yield and Quality"; J. Prod. Agic., vol. 11, No. 1, 1998.
Pendleton, et al., "Plant Population and Row Spacing Studies with brachytic 2 Dwarf Corn"; Contribution from the Department of Agronomy, Illinois Agr. Exp. Sta., Urbana, III; pp. 433-435, 1961.
Begna, et al., "Effects of Population Density and Planting Pattern on the Yield and Yield Components of Leafy Reduced-Stature Maize in a Short-Season Area"; J. Agronomy & Crop Science 179, pp. 9-17; 1997.
Cox, et al., "Corn Silage and Grain Yield Responses to Plant Densities"; J. Prod. Agric., vol. 10, No. 3, pp. 405-410, 1997.
Abendroth & Elmore, presentation titled "Corn Growth and Development" available at https://www.ipm.iastate.edu/files/curriculum/03%20Corn%20Growth%20and%20Development_0.pdf, accessed Feb. 12, 2025.
International Search Report and Written Opinion mailed Apr. 22, 2020, in International Application No. PCT/US2019/064270, pp. 1-14.
"4 Series Sprayers," Published in May 2016, obtained from https://www.deere.com/en_CAF/docs/product/equipment/4_Series_Sprayers.pdf (2016).
Amanullah et al., "Phenology, Growth, and Grain Yield of Maize as Influenced by Foliar Applied Urea at Different Growth Stages," Journal of Plant Nutrition 33:1; 71-79 (2010).
"Corn Herbicide Application Timings," published by online by PennState Extension; obtained from https://extension.psu.edu/corn-herbicide-application-timings (2015).
Crommelinck et al., "Simulating an Autonomously Operating Low-Cost Static Terrestrial LiDAR for Multitemporal Maize Crop Height Measurements," Remote Sensing, 8(3):205, pp. 1-17 (2016).
D'Andrea et al., "Genotypic Variability in Morphological and Physiological Traits among Maize Inbred Lines-Nitrogen Responses," Crop Sci., 46:1266-1276 (2006).
GenBank Accession No. AY366085, "*Zea mays* cultivar B73 PGP1 (pgp1) gene, complete cds" (2003).
International Search Report and Written Opinion mailed Aug. 8, 2019, in International Application No. PCT/US2019/018129.
International Search Report and Written Opinion mailed May 10, 2019, in International Application No. PCT/US2019/018127.
Kempton, "Heritable Characters of Maize, III. Brachytic Culms," Jour. Hered., 11(1):111-115 (1920).
Lu, "Chapter 3 Research on Production Increase Technology in Late Harvesting of Maize in Optimum Period," Theory and Technology of High Yield of Maize (2015).
Mourtzinis et al., "Corn Grain and Stover Yield Prediction at RI Growth Stage," Agronomy Journal, 105 (4):1045-1050 (2013).

(56) References Cited

OTHER PUBLICATIONS

Multani et al., "Loss of an MDR Transporter in Compact Stalks of Maize br2 and Sorghum dw3 Mutants," Science, 302:81-84 (2003).
Pilu et al., "Isolation and characterization of a new mutant allele of brachytic 2 maize gene," Molecular Breeding, 20:83-91 (2007).
Qiao et al., "The influence of RNAi targeting of OsGA20ox2 gene on plant height in rice," Plant Molecular Biology Reporting 29.4:952-960 (2011).
Wang et al., "Analysis of hormone sensitivity of a dwarf mutant of maize," Journal of Northwest A&F University (Nat. Sci. Ed.) 45(8) (2017).
Weng et al., "Genome-Wide Association Study Identifies Candidate Genes That Affect Plant Height in Chinese Elite Maize (*Zea mays* L.) Inbred Lines," PLOS One 6(12) (2011).
Zaidi et al., "Phenotyping for Abiotic Stress Tolerance in Maize Heat Stress," CIMMYT, pp. 1-40 (2016).
Butzen, "Timing Corn Harvest," Crop Insights, (Sep. 2018).
Chen et al., "Identification and genetic mapping for rht-DM, a dominant dwarfing gene in mutant semi-dwarf maize using QTL-seq approach," Genes & Genomics 40, pp. 1091-1099 (Jun. 2018) (electronic publication).
Supplementary European Search Report dated Oct. 11, 2022 in EP 19 89 2688.
Thomison et al., "Corn Response to Harvest Date a Affected by Plant Population and Hybrid," Agron J. 103, pp. 1765-1772 (Sep. 2011) (electronic publication).
Altschul, "Basic local alignment search tool." Journal of Molecular Biology, 15:403-410 (1990).
Xia et al., "A book to understand high corn yield and disaster prevention and reduction technology", China Farmers Press, May 2016, p. 135.
Chinese Office Action regarding Chinese Patent Application No. 201980025083.0, dated Dec. 1, 2023, 19 pages.
Chenna, et al., "Multiple sequence alignment with the Clustal series of programs," Nucleic Acids Research, 31(13): 3497-3500 (2003).
De Pater, et al., "The promoter of the rice gene GOS2 is active in various different monocot tissues and binds rice nuclear factor ASF-1," The Plant Journal, 2(6): 837- 844 (1992).
Elmore, et al., "In-Field Drydown Rates and Harvest," Iowa State University Extension and Outreach, retrieved from <https://crops.extension.iastate.edu/cropnews/2010/09/field-drydown-rates-and-harvest> (Sep. 28, 2010).
Guo, et al., "RNA Silencing in Plants: Mechanism, Technologies and Applications in Horticulture Crops," Current Genomics, 17(6):476-489 (2016).
Hanway, "How a corn plant develops," Special Report No. 48, Iowa State University, CES, Ames, IA, (1966).
Inada, "Quality controls induced by aberrant translation," Nucleic Acids Research, 48(3): 1084-1096 (2020).
Israelsen, "Harvesting Corn Silage by Plant Moisture" article adapted from Crop and Soils Magazine, Utah State University Agricultural Extension Agents, (2009). Retrieved from <https://digitalcommons.usu.edu/cgi/viewcontent.cgi?article=1145&context=extension_curall>.
Karamyshev, et al., "Lost in Translation: Ribosome-Associated mRNA and Protein Quality Controls," Frontiers in Genetics, 9:431 (2018).
Last, et al., "pEmu: an improved promoter for gene expression in cereal cells," Theoretical and Applied Genetics, 81:581-588 (1991).
Mcelroy, et al., "Construction of expression vectors based on the rice actin 1 (Actl) 5' region for use in monocot transformation," Molecular and General Genetics MGG, 231: 150-160 (1991).
Nickless, et al., "Control of gene expression through the nonsense-mediated RNA decay pathway," Cell & Bioscience, 7:26 (2017).
Ritchie, S.W. et al., "How a Corn Plant Develops," Special Report No. 48, Iowa State University, CES, Ames, IA, Reprinted 1986.
Spelhaug, "Predicting Your Corn Harvest Date," Peterson Farms Seed (2013).
Szadeczky-Kardoss, et al., "The nonstop decay and the RNA silencing systems operate cooperatively in plants," Nucleic Acids Research, 46(9): 4632-4648 (2018).
Thompson, et al., "Clustal W: Improving the sensitivity of progressive multiple sequence alignment through sequence weighting, position-specific gap penalties and weight matrix choice," Nucleic Acids Research, 22: 4673-4680 (1994).
Wilson, et al., "Molecular Mechanisms of RNA Interference," Annual Review of Biophysics, 42: 217-39 (2013).
Bolduc and Hake, The maize transcription factor Knotted1 directly regulates the gibberellin catabolism gene ga2ox1, Plant Cell 21:1647-1658, 2009.
R4038-sprayer by John Deere, available at https://kibbleeq.com/farmers/sprayers-&-applicators/self-propelled-sprayers/john-deere-sprayers/r4038-sprayer, accessed Apr. 29, 2024.
Sun et al., Identification and characterization of El (Elongated Internode) gene in tomato (Solanum lycopersicum), Int. J. Mol. Sci. 20(2204): 1-18, 2019.
Sehgal. "Inbred-Hybrid Method of Maize Improvement." Proceeding of the Caribbean Food Crops Society Fourth Annual Meeting, 1966.
Chen, et al. "Development of dwarfish and yield-effective GM maize through passivation of bioactive gibberellin." Transgenic Res, 28:589-599, (2019).
Köllner, et al. "Herbivore-Induced Sabath Methyltransferases of Maize that Methylate Anthranilic Acid Using S-Adenosyl-L-Methionine." Plant Physiology, vol. 153, pp. 1795-1807, (2010).
Search Report dated Jul. 21, 2022, in Chinese Application 2017800639820 including English translation of related Office Action.
Allen, et al., "Evolution of microRNA genes by inverted duplication of target gene sequences in *Arabidopsis thaliana*," Nature Genetics, 36:1282-1290 (2004).
Allen, et al., "microRNA-directed phasing during Trans-acting siRNA Biogenesis in plants," Cell, 121(2):207-221 (2005).
U.S. Appl. No. 19/425,440, filed Dec. 18, 2025, Cannon et al.
Bage, et al., "Genetic characterization of novel and CRISPR-Cas9 gene edited maize brachytic 2 alleles." Plant Gene, 21:100198 (2020).
Knöller, et al., "Brachytic2/ZmABCB1 functions in IAA export from intercalary meristems." J. Exp. Botany, 61:3689-3696 (2010).
Zhang, et al., "Maize brachytic2 (br2) suppresses the elongation of lower internodes for excessive auxin accumulation in the intercalary meristem region." BMC Plant Biology, 19:589 (2019).
Uniprot A0A2P1BTK0_MAIZE. Brachytic 2. Accessed on Dec. 27, 2024. Accessed from <https://www.uniprot.org/uniprotkb/A0A2P1BTK0/entry>.
U.S. Appl. No. 19/337,629, filed Sep. 23, 2025, Cannon et al.
International Search Report and Written Opinion for International Application No. PCT/US2023/66999 mailed Nov. 2, 2023.
Amandeep K. Dhaliwal et al., Comparative analysis of ABCB1 reveals novel structural and functional conservation between monocots and dicots, Frontiers in Plant Science, 2014, vol. 5, Article 657.
USPTO: Final Office Action regarding U.S. Appl. No. 17/530,873, mailed Jul. 31, 2025.
Altschul, et al., "Gapped BLAST and PSI-BLAST: a new generation of protein database search programs," Nucleic Acids Research, 25 (17) : 3389-3402 (1997).
Ashikari, et al., "Loss-of-function of a Rice Gibberellin Biosynthetic Gene, GA20 oxidase (GA20ox-2), Led to the Rice 'Green Revolution'," Breeding Science, 52:143-150 (2002).
Axtell, et al., "A Two-Hit Trigger for siRNA Biogenesis in Plants," Cell, 127:565-577 (2006).
Beurdeley, et al., "Compact designer TALENs for efficient genome engineering", Nature Communications, 4: 1762 (2013).
Cai, et al., "Molecular Cloning, Characterization, and Expression Analysis of Genes Encoding Gibberellin 20-Oxidase in Dasypyrum villosum Dwarf Mutant," Plant Molecular Biology Reporter, 30:1110-1116 (2012).
Carrera, et al.,"Changes in GA 20-oxidase gene expression strongly affect stem length, tuber induction and tuber yield of potato plants," The Plant Journal, 22(3):247-256 (2000).

(56) References Cited

OTHER PUBLICATIONS

Cermak, et al., "Efficient design and assembly of custom TALEN and other TAL effector-based constructs for DNA targeting," Nucleic Acids Research, 39(12):e82 (2011).
Chen, et al., "Identification and Functional Analysis of Flowering Related microRNAs in Common Wild Rice (*Oryza rufipogon* Griff.)," PLoS ONE, 8:e82844 (2013).
Chen, et al., "New insight in the Gibberellin biosynthesis and signal transduction," Plant Signaling & Behavior, 10(5):e1000140-1-e1000140-3:(2015).
Chen, et al., "The Maize DWARF1 Encodes a Gibberellin 3-Oxidase and Is Dual Localized to the Nucleus and Cytosol," Plant Physiology, 166:2028-2039 (2014).
Ciampitti, et al., "A comprehensive study of plant density consequences on nitrogen uptake dynamics of maize plants from vegetative to reproductive stages," Field Crops Research, 121(1):2-18 (2011).
Coles, et al., "Modification of gibberellin production and plant development in *Arabidopsis* by sense and antisense expression of gibberellin 20-oxidase genes," The Plant Journal, 17 (5):547-556 (1999).
Davis, et al., "Gibberellin Biosynthesis in Maize. Metabolic Studies with GA15, GA24, GA25, GA7, and 2,3-Dehydro-GA91," Plant Physiology, 121(3):1037-1045 (1999).
Doyle, et al., "TAL Effector-Nucleotide Targeter (TALE-NT) 2.0: tools for TAL effector design and target prediction," Nucleic Acids Research, 40:W117-122 (2012).
Du, et al., "Cloning and characterization of an up-regulated GA 20-oxidase gene in hybrid maize," Natural Science, 19 (2):161-166 (2009).
Eriksson, et al., "GA4 Is the Active Gibberellin in the Regulation of LEAFY Transcription and *Arabidopsis* Floral Initiation," The Plant Cell, 18(9):2172-2181 (2006).
Extended European Search Report dated Mar. 9, 2020, in European Patent Application No. 17842139.2.
Fagoaga, et al., "Engineering of gibberellin levels in citrus by sense and antisense overexpression of a GA 20-oxidase gene modifies plant architecture," Journal of Experimental Botany, 58(6):1407-1420 (2007).
Fambrini, et al., "The extreme dwarf phenotype of the GA-sensitive mutant of sunflower, dwarf2, is generated by a deletion in the ent-kaurenoic acid oxidase1 (HaKAO1) gene sequence," Plant Molecular Biology, 75:431-450 (2011).
Franco-Zorrilla, et al., "Target mimicry provides a new mechanism for regulation of microRNA activity," Nature Genetics, 39: 1033-1037 (2007).
Gabsalilow, et al., "Site- and strand-specific nicking of DNA by fusion proteins derived from MutH and I-SceI or TALE repeats," Nucleic Acids Research, 41(7):e83 (2013).
Gaj, et al.. "ZFN, TALEN, and CRISPR/Cas-based methods for genome engineering," Trends Biotechnology, 31 (7):397-405 (2013).
GenBank Accession No. AY105651.1, "*Zea mays* PC0130567 mRNA sequence," pp. 1-2, dated May 28, 2008.
GenBank Accession No. BT068785.2, "*Zea mays*full-length cDNA clone ZM_BFb0382B03 mRNA, complete cds," pp. 1-2, dated Jun. 15, 2012.
GenBank Accession No. EU963664.1, "*Zea mays* clone 265382 gibberellin 20 oxidase 2 mRNA, complete cds," pp. 1, dated Dec. 10, 2008.
Griffiths-Jones, et al., "Rfam: an RNA family database," Nucleic Acids Research, 31(1):439-441 (2003).
Gupta, et al., "Gibberellic acid in plant Still a mystery unresolved," Plant Signaling & Behavior, 8(9):e25504 (2013).
Han, et al., "Gibberellin-associated cisgenes modify growth, stature and wood properties in Populus," Plant Biotechnology Journal, 9(2):162-178 (2011).
Hedden, et al., "Gibberellin Biosynthesis: Enzymes, Genes and Their Regulation," Annu. Rev. Plant Physiol. Plant Mol. Biol., 48:431-60 (1997).
Hedden, "The genes of the Green Revolution," Trends in Genetics, 19(1):5-9 (2003).
Helliwell, et al "Constructs and Methods for Hairpin RNA-Mediated Gene Silencing in Plants," Methods in Enzymology, 392:24-35 (2003).
Huang, et al., "A Gibberellin-Mediated DELLA-NAC Signaling Cascade Regulates Cellulose Synthesis in Rice," The Plant Cell, 27(6):1681-1696 (2015).
International Search Report and Written Opinion mailed Dec. 28, 2017, in International Application No. PCT/US2017/047405.
Jia, et al., "GA-20 oxidase as a candidate for the semidwarf gene sdw1/denso in barley," Functional & Integrative Genomics, 9:255-262 (2009).
Jia, et al., "Molecular characterization and functional analysis of barley semi-dwarf mutant Riso No. 9265," BMC Genomics, 16(927):1-11 (2015).
Jones-Rhoades, et al., "Computational Identification of Plant MicroRNAs and Their Targets, Including a Stress-Induced miRNA," Molecular Cell, 14(6):787-799 (2004).
Kamthan, et al., "Small RNAs in plants: recent development and application for crop improvement" Frontiers in Plant Science, 6:1-17 (2015).
Katoh, et al., "Specific residues at every third position of siRNA shape its efficient RNAi activity," Nucleic Acids Research, 35(4): e27 (2007).
Khvorova, et al., "Functional siRNAs and miRNAs Exhibit Strand Bias," Cell, 115(2):209-216 (2003).
Kim, "MicroRNA Biogenesis: Coordinated Cropping and Dicing," Nature Reviews Molecular Cell Biology, 6:376-385 (2005).
King, et al., "Selective Deactivation of Gibberellins below the Shoot Apex is Critical to Flowering but Not to Stem Elongation of Lolium," Molecular Plant, 1(2):295-307 (2008).
Kobayashi, et al., "Gibberellin Metabolism in Maize (The Stepwise Conversion of Gibberellin A12-Aldehyde to Gibberellin A20)," Plant Physiology, 110(2):413-418 (1996).
Kusaba, et al., "Isolation and expression analysis of gibberellin 20-oxidase homologous gene in apple," Journal of Experimental Botany, 52(335):375-376 (2001).
Lange, et al., "Gibberellin Biosynthesis and the Regulation of Plant Development," Plant Biology, 8(3):281-290 (2006).
Larkin, et al., "Clustal W and Clustal X version 2.0," Bioinformatics, 23(21):2947-48 (2007).
Liu, et al., "Analysis of Complementarity Requirements for Plant MicroRNA Targeting Using a Nicotiana benthamiana Quantitative Transient Assay," The Plant Cell, 26(2):741-753 (2014).
Mitchum, et al., "Distinct and overlapping roles of two gibberellin 3-oxidases in *Arabidopsis* development," The Plant Journal, 45(5):804-818 (2006).
Molina, et al., "Transformation of a Dwarf *Arabidopsis* Mutant Illustrates Gibberellin Hormone Physiology and the Function of a Green Revolution Gene," Biochemistry and Molecular Biology Education, 37(3): 170-177 (2009).
Mutasa-Gottgens, et al., "Gibberellin as a factor in floral regulatory networks," Journal of Experimental Botany, 60 (7):1979-1989 (2009).
Offtype—Definition of Offtype by Merriam-Webster, pp. 1, retrieved Sep. 18, 2023 <https://www.merriam-webster.com/dictionary/offtype>.
Jayasundara et al., Energy and Greenhouse Gas Intensity of Corn (*Zea Mays* L. ) Production in Ontario: a Regional Assessment, Can J. Soil Sci. 94:77-95, 2014.
Lindsey & Zoller, Useful Tables: Adjustments and Conversions on Corn and Soybean Parameters, article on the Ohio State University Extension website https://ohioline.osu.edu/factsheet/agf-502, 2018.
Nielsen, Short Corn at Tasseling, article for Purdue Agronomy available at https://www.agry.purdue.edu/ext/corn/news/articles.01/short_corn-0712.html, 2001.
GenBank AJ132435. "*Arabidopsis thaliana* mRNA for GA 2-oxidase, gene ga20x1" Dated 1999. Retrieved from: <https://www.ncbi.nlm.nih.gov/nuccore/AJ132435>.
Xing, et al. "A rare SNP mutation in Brachytic2 moderately reduces plant height and increases yield potential in maize." Journal of Experimental Botany, vol. 66, Issue 13, pp. 3791-3802, (2015).

(56) References Cited

OTHER PUBLICATIONS

Thomas, et al. "Size constraints for targeting post-transcriptional gene silencing and for RNA-directed methylation in Nicotiana benthamiana using a potato virus X vector." The Plant Journal, vol. 25(4), pp. 417-425, (2001).
Macrobert, et al. "Maize Hybrid Seed Production Manual." International Maize and Wheat Improvement Center. (2014).
Haegele, et al. "Row Arrangement, Phosphorus Fertility, and Hybrid Contributions to Managing Increased Plant Density of Maize." Agronomy, vol. 106(5), pp. 1838-1846, (2014).
Guo, et al. "Protein tolerance to random amino acid change." Proc. Natl. Acad. Sci. U.S.A., vol. 101 (25), pp. 9205-9210, (2004).
Da Silva et al., Adaptability and Stability of Corn Hybrids Grown for Grain Yield, Maringa 36(2): 175-181, 2014.
Balzan, Sara et al, "Genetic and phenotypic characterization of a novel brachytic 2 allele of maize", Plant Growth Regulation Springer Netherlands, Dordrecht, vol. 86, No. 1, 19, pp. 81-92 (Year: 2018).
European Search Report regarding European App. No. 23808488.3, mailed Apr. 22, 2026.

* cited by examiner

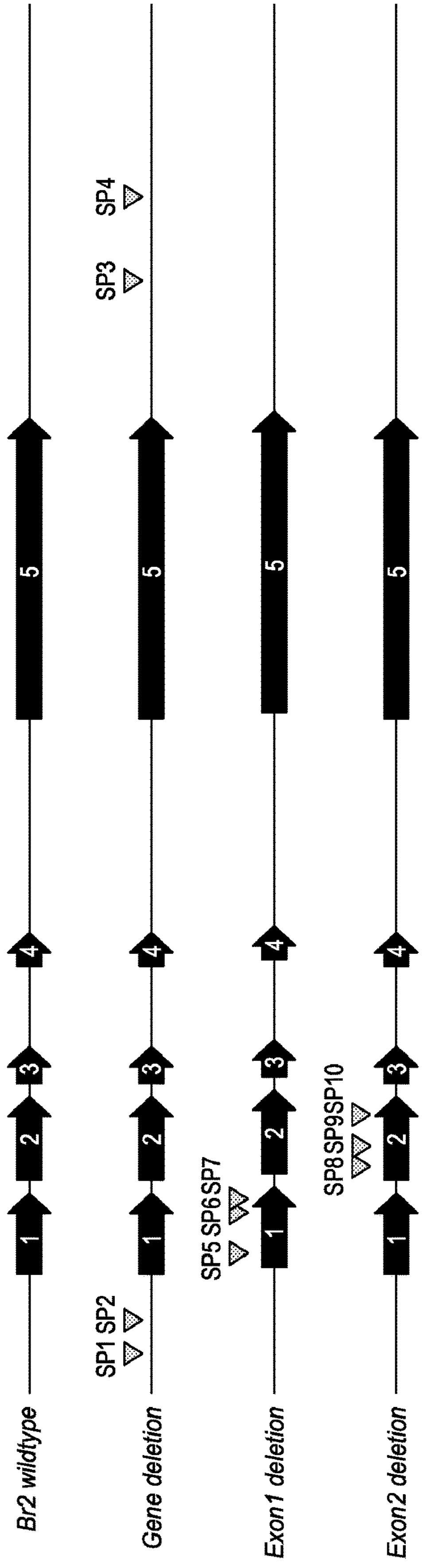
Br2 wildtype
Gene deletion
Exon1 deletion
Exon2 deletion
SP1
SP2
SP3
SP4
SP5
SP6
SP7
SP8
SP9
SP10
1
2
3
4
5

METHODS AND COMPOSITIONS FOR GENERATING DOMINANT BRACHYTIC ALLELES USING GENOME EDITING

CROSS-REFERENCE TO RELATED APPLICATIONS

This is a 371 National Phase Application from International Patent Application No. PCT/US2023/066999, filed May 15, 2023, which application claims the priority of U.S. Provisional Appl. Ser. No. 63/343,511, filed May 18, 2022, the entire disclosure of each of which is incorporated herein by reference.

INCORPORATION OF SEQUENCE LISTING

The instant application contains a Sequence Listing created on May 12, 2023, named "MONS563WO_ST26", which is 83.6 kilobytes in size, contains 64 sequences, and is submitted electronically herewith, and which is hereby incorporated herein by reference in its entirety.

FIELD

The present disclosure relates to dominant or semi-dominant alleles of the brachytic 2 gene generated via targeted genome editing in corn.

BACKGROUND

Sustained increases in crop yields have been achieved over the last century through the development of improved varieties and agronomic practices. Semi-dwarf varieties of certain crops, such as wheat and rice, were developed having reduced plant height and improved lodging tolerance have been developed. Moreover, dwarf and semi-dwarf traits or varieties have the potential for higher planting densities to help improve crop yields. Indeed, the development of dwarf and semi-dwarf varieties of wheat and rice served as a cornerstone of the so-called "Green revolution" of the late 20th century.

Maize (*Zea mays* L.), a member of the Poaceae (or Gramineae) family, provides cylindrical stalks similar to those from other grasses. Commercial hybrid maize can grow to a height of more than 2 meters with each plant having either one or two ears. As a result of its height and vertical structure, a maize plant can be subjected to significant mechanical forces, particularly during high-wind weather events, that can cause maize plants to lodge resulting in a loss of harvestable yield. However, a reduction in the height of a maize plant can improve its mechanical stability and lodging resistance under such conditions.

Many dwarfing mutants have been described in maize, but a majority of these mutants lead to reductions in grain yield and consequently have not been used to enhance crop yield in corn despite the potential lodging resistance benefit. Therefore, an important goal in commercial breeding is to identify novel dwarf or semi-dwarf mutations that confer a short stature phenotype without negatively impacting other plant organs, especially reproductive organs (e.g., ears), that could ultimately impact yield. In maize, brachytic mutants have been shown to have a short stature phenotype due to shortening of internode lengths without a corresponding reduction in the number of internodes or the number and size of other organs, including the leaves, ear and tassel.

Three brachytic mutants have been isolated in maize to date: brachytic1 (br1), brachytic2 (br2) and brachytic3 (br3). Br3 is also commonly referred to as *brevis* plant 1 (bvl). Both br1 and br3 mutations cause a reduction in corn plant height which has been thought too severe for commercial use due to potential impacts on yield. In contrast, br2 mutants have particular agronomic potential because of the shortening of the lower stalk internodes with no obvious negative impact on reproductive plant organs and yield. In addition, br2 lines exhibit an increased stalk strength and tolerance to wind lodging, while the leaves are often darker and persist longer as active green leaves than corresponding wild-type plants. See, e.g., PCT/US2016/029492, the entire content and disclosure of which are incorporated herein by reference. However, loss-of-function mutant alleles of the br2 gene that have been described are generally recessive and require the plants to be homozygous for the mutant allele.

There is a need for the development of dominant or semi-dominant traits that cause a dwarf or semi-dwarf phenotype in corn or maize plants that can be used to improve yield and/or lodging resistance and which do not need to be present in a homozygous state to provide a yield and/or lodging benefit, thus facilitating the production of hybrid corn plants and seeds carrying the trait. The present disclosure provides dominant or semi-dominant mutations or edits of the endogenous br2 locus that can produce a dwarf or semi-dwarf trait with improved yield and/or lodging resistance in corn or maize plants.

BRIEF DESCRIPTION OF THE DRAWINGS

FIG. 1 provides an illustration for a set of three different genome editing schemes to produce deletions of the entire coding region or edits or deletions in exon 1 or exon 2 of the endogenous Zm.br2 gene locus with guide RNAs SP1-SP4 targeting the deletion of the entire coding region, and guide RNAs SP5-SP7 and SP8-SP10 targeting edits or deletions in exon 1 and exon 2 of the Zm.br2 gene, respectively.

DETAILED DESCRIPTION

Unless defined otherwise herein, terms are to be understood according to conventional usage by those of ordinary skill in the relevant art. To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, a "plant" includes an explant, plant part, seedling, plantlet or whole plant at any stage of regeneration or development. The term "cereal plant" as used herein refers a monocotyledonous (monocot) crop plant that is in the Poaceae or Gramineae family of grasses and is typically harvested for its seed, including, for example, wheat, corn, rice, millet, barley, sorghum, oat and rye. As commonly understood, a "corn plant" or "maize plant" (or simply "corn" or "maize") refers to any plant of species *Zea mays* and includes all plant varieties that can be bred with corn, including wild maize species.

As used herein, a "plant part" refers to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure can be viable, nonviable, regenerable, and/or non-regenerable. A "propagule" can include any plant part that can grow into an entire plant.

As used herein, "locus" is a chromosomal locus or region where a polymorphic nucleic acid, trait determinant, gene, or marker is located. A "locus" can be shared by two homologous chromosomes to refer to their corresponding locus or region.

As used herein, "allele" refers to an alternative nucleic acid sequence of a gene or at a particular locus (e.g., a nucleic acid sequence of a gene or locus that is different than other alleles for the same gene or locus). Such an allele can be considered (i) wild-type or (ii) mutant if one or more mutations or edits are present in the nucleic acid sequence of the mutant allele relative to the wild-type allele. Thus, a "mutant allele" of an endogenous gene or locus is an allele of the gene or locus comprising one or more edit(s) and/or mutation(s). If a mutant allele comprises one or more edits, then the mutant allele can also be referred to as an "edited allele." A mutant allele for a gene may have a reduced or eliminated activity or expression level for the gene relative to the wild-type allele. A mutant allele may be dominant, semi-dominant or recessive. As commonly understood in the art, a dominant or semi-dominant mutant allele of a gene can impact the expression and/or function of the other copy of the gene on the homologous chromosome even if the other copy of the gene is a wild-type allele. For diploid organisms such as corn, a first allele can occur on one chromosome, and a second allele can occur at the same locus on a second homologous chromosome. If one allele at a locus on one chromosome of a plant is a mutant allele and the other corresponding allele on the homologous chromosome of the plant is wild-type, then the plant is described as being heterozygous for the mutant allele. However, if both alleles at a locus are mutant alleles, then the plant is described as being homozygous for the mutant alleles. A plant homozygous for mutant alleles at a locus may comprise the same mutant allele or different mutant alleles if heteroallelic or biallelic.

As used herein, an "endogenous locus" refers to a locus at its natural and original chromosomal location. As used herein, the "endogenous br2 locus" refers to the brachytic2 (br2) genic locus at its original chromosomal or genomic location in a corn or maize plant.

As used herein, a "gene" refers to a nucleic acid sequence forming a genetic and functional unit and coding for one or more sequence-related RNA and/or polypeptide molecules. A gene generally contains a coding region operably linked to appropriate regulatory sequences that regulate the expression of a gene product (e.g., a polypeptide or a functional RNA). A gene can have various sequence elements, including, but not limited to, a promoter, an untranslated region (UTR), exons, introns, and other upstream or downstream regulatory sequences.

As used herein, in the context of a protein-coding gene, an "exon" refers to a segment of a DNA or RNA molecule containing information coding for a protein or polypeptide sequence.

As used herein, an "intron" refers to a segment of a DNA or RNA molecule, which does not contain information coding for a protein or polypeptide, and which is first transcribed into a RNA sequence but then spliced out from a mature RNA molecule.

As used herein, an "untranslated region (UTR)" refers to a segment of a RNA molecule or sequence (e.g., a mRNA molecule) transcribed from a gene (or transgene) but excluding the exon and intron sequences of the mRNA molecule. An "untranslated region (UTR)" also refers a DNA segment or sequence encoding such a UTR segment of a mRNA molecule. An untranslated region can be a 5'-UTR or a 3'-UTR depending on whether it is located at the 5' or 3' end of a DNA or RNA molecule or sequence relative to a coding region of the DNA or RNA molecule or sequence (i.e., upstream or downstream of the exon and intron sequences, respectively).

As used herein, the term "expression" refers to the biosynthesis of a gene product, and typically includes transcription and/or translation of a nucleotide sequence, such as an endogenous gene, a heterologous gene, a transgene or a RNA and/or protein coding sequence, in a cell, tissue, organ, or organism, such as a plant, plant part or plant cell, tissue or organ.

As used herein, a "native sequence" refers to a nucleic acid sequence naturally present in its original or native chromosomal location.

As used herein, a "wild-type gene" or "wild-type allele" refers to a gene or allele having a sequence or genotype that is most common in a particular plant species, or another sequence or genotype with natural variations, polymorphisms, or other silent mutations relative to the most common sequence or genotype that do not significantly impact the expression and activity of the gene or allele. Indeed, a "wild-type" gene or allele contains no variation, polymorphism, or any other type of mutation that substantially affects the normal function, activity, expression, or phenotypic consequence of the gene or allele.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, an uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" may also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

For optimal alignment of sequences to calculate their percent identity, various pair-wise or multiple sequence alignment algorithms and programs are known in the art, such as ClustalW, or Basic Local Alignment Search Tool® (BLAST®), etc., that may be used to compare the sequence identity or similarity between two or more nucleotide or protein sequences. Although other alignment and comparison methods are known in the art, the alignment between two sequences (including the percent identity ranges described above) may be as determined by the ClustalW or BLAST® algorithm, see, e.g., Chenna R. et al., "Multiple sequence alignment with the Clustal series of programs," *Nucleic Acids Research* 31:3497-3500 (2003); Thompson J D et al., "Clustal W: Improving the sensitivity of progressive multiple sequence alignment through sequence weighting, position-specific gap penalties and weight matrix choice," *Nucleic Acids Research* 22:4673-4680 (1994); and Larkin M A et al., "Clustal W and Clustal X version 2.0," *Bioinformatics* 23:2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity may be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences may be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

As used herein, with respective to a given sequence, a "complement", a "complementary sequence" and a "reverse complement" are used interchangeably. All three terms refer to the inversely complementary sequence of a nucleotide sequence—i.e., to a sequence complementary to a given sequence in reverse order of the nucleotides. As an example, the reverse complement of a nucleotide sequence having the sequence 5'-atggttc-3' is 5'-gaaccat-3'.

As used herein, the term "antisense" refers to DNA or RNA sequences that are complementary to a specific DNA or RNA sequence. Antisense RNA molecules are single-stranded nucleic acids which can combine with a sense RNA strand or sequence or mRNA to form duplexes due to complementarity of the sequences. The term "antisense strand" refers to a nucleic acid strand that is complementary to the "sense" strand. The "sense strand" of a gene or locus is the strand of DNA or RNA that has the same sequence as a RNA molecule transcribed from the gene or locus (with the exception of Uracil in RNA and Thymine in DNA).

As used herein, an "inverted genomic fragment" refers to a genomic segment that is inverted in the genome such that the original sense strand and antisense strand sequences are reversed or switched in the opposite orientation for the entire genomic segment.

As used herein, unless specified otherwise, the relative location of two sequence elements of a genic locus, when expressed as "upstream," "downstream," "at the 5' end," or "at the 3' end," is determined based on the direction of the transcription activity associated with that genic locus. For example, for two genic DNA elements or sequences, their relative location is based on their sense strand where a first genomic DNA element or sequence is upstream or at the 5' end relative to a second genomic DNA element or sequence when the first genomic DNA element or sequence is located on the side of the second genomic DNA element or sequence that is opposite the direction of transcription. Likewise, a first genomic DNA element or sequence is downstream or at the 3' end relative to a second genomic DNA element or sequence when the first genomic DNA element or sequence is located on the side of the second genomic DNA element or sequence that is in the direction of transcription.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s). Two transcribable DNA sequences can also be "operably linked" to each other if their transcription is subject to the control of a common promoter or other regulatory element.

As used herein, an "encoding region" or "coding region" refers to a portion of a polynucleotide or gene that encodes a functional unit or molecule (e.g., without being limiting, a mRNA, protein, or non-coding RNA sequence or molecule). An "encoding region" or "coding region" can contain, for example, one or more exons or one or more exons and one or more introns.

As used herein, "adjacent" refers to a nucleic acid sequence, segment, segment or element that is in close proximity or next to another nucleic acid sequence, segment, segment or element. In one aspect, adjacent nucleic acid sequences, etc., are physically linked. In another aspect, adjacent nucleic acid sequences, etc., are immediately next to each other such that there are no intervening nucleotides between the end of a first nucleic acid sequence, etc., and the start of a second nucleic acid sequence, etc. In an aspect, a first gene, segment, sequence, or element and a second gene, segment, sequence, or element are adjacent to each other if they are separated by less than 50,000, less than 25,000, less than 10,000, less than 9000, less than 8000, less than 7000, less than 6000, less than 5000, less than 4000, less than 3000, less than 2500, less than 2000, less than 1750, less than 1500, less than 1250, less than 1000, less than 900, less than 800, less than 700, less than 600, less than 500, less than 400, less than 300, less than 200, less than 100, less than 75, less than 50, less than 25, less than 20, less than 10, less than 5, less than 4, less than 3, less than 2, or less than 1 nucleotide.

As used herein, a "targeted genome editing technique" or "targeted editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a transcription activator-like effector (TALE) nuclease (TALEN), a recombinase, or a transposase. As used herein, "editing" or "genome editing" refers to generating a targeted mutation, insertion, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides within the nucleic acid sequence of an endogenous plant genome, locus or gene. As used herein, "editing" or "genome editing" also encompasses the targeted insertion or site-directed insertion, integration or addition of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant. An "edit" or "genomic edit" in the singular refers to one such targeted mutation, deletion, inversion, substitution and/or insertion, whereas "edits" or "genomic edits" refers to two or more targeted mutation(s), deletion(s), inversion(s), substitution(s) and/or insertion(s), with each "edit" being introduced via a targeted genome editing technique. In an aspect, an edit can comprise any combination of a deletion, inversion, substitution and/or insertion.

As used herein, "modified" in the context of a plant, plant seed, plant part, plant cell, and/or plant genome, refers to a plant, plant seed, plant part, plant cell, and/or plant genome comprising an engineered change in one or more genes of interest relative to a wild-type or control plant, plant seed, plant part, plant cell, and/or plant genome that alters the expression level and/or coding sequence of the one or more genes of interest. The term "modified" may further refer to a plant, plant seed, plant part, plant cell, and/or plant genome having one or more inversions, deletions, insertions, or combinations thereof, affecting the expression or coding sequence of an endogenous br2 gene, and/or the function of an endogenous Br2 protein (encoded by a br2 gene or allele), introduced through chemical mutagenesis, radiation mutagenesis, transposon insertion or excision, or any other known mutagenesis technique, or introduced through genome editing. For clarity, therefore, a modified plant, plant seed, plant part, plant cell, and/or plant genome includes a mutated and/or edited plant, plant seed, plant part, plant cell, and/or plant genome having a modified expression level, expression pattern, and/or coding sequence of a br2 gene and/or Br2 protein relative to a wild-type or control plant, plant seed, plant part, plant cell, and/or plant genome. Modified plants can be homozygous or heterozygous for any given mutation or edit or mutant allele, and/or may be biallelic or heteroallelic for one or more mutations and/or edits at a br2 gene locus. A modified plant is bi-allelic or heteroallelic for a br2 gene if each copy of the br2 gene is a different mutant allele (i.e., comprises different mutation(s) and/or edit(s)), wherein each allele modifies the expression level, sequence and/or activity of the br2 gene and/or encoded Br2 protein. Modified plants, plant parts, seeds, etc., may have been subjected to or made using a mutagenesis, genome editing or site-directed integration (e.g., without being limiting, via methods using site-specific nucleases), or genetic transformation (e.g., without being limiting, via methods of *Agrobacterium* transformation or microprojectile bombardment) method or technique, or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change(s) (e.g., change in expression level, sequence and/or activity) to the br2 gene (i.e., retain a mutant allele(s) of the br2 gene). A modified seed provided herein may give rise to a modified plant provided herein. A modified plant, plant seed, plant part, plant cell, or plant genome provided herein may comprise a mutation or edit of a br2 gene as provided herein. A "modified plant product" may be any product, such as a commodity product, made from a modified plant, plant part, plant cell, or plant chromosome provided herein, or any portion or component thereof.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a mutation(s) and/or genome edit(s) (e.g., inversion, deletion, or insertion) in or affecting a br2 gene (i.e., except for a mutant allele(s) of the br2 gene). For example, a control plant may be an inbred line that is the same as the inbred line used to make the modified plant, or a control plant may be the product of the same hybrid cross of inbred parental lines as the modified plant, except for the absence in the control plant of any mutation(s) or genome edit(s) in or affecting a br2 gene (i.e., except for the absence in the control plant of a mutant allele(s) of the br2 gene). Similarly, an unmodified control plant refers to a plant that shares a substantially similar or essentially identical genetic background as a modified plant, but without the one or more engineered changes to the genome (e.g., transgene, mutation or edit) of the modified plant. For purposes of comparison to a modified plant, plant seed, plant part, plant cell and/or plant genome, a "wild-type plant" (or likewise a "wild-type" plant seed, plant part, plant cell and/or plant genome) refers to a non-transgenic and non-genome edited control plant, plant seed, plant part, plant cell and/or plant genome. As used herein, a "control" plant, plant seed, plant part, plant cell and/or plant genome may also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, a "target site" for genome editing refers to the polynucleotide sequence of a location within a plant genome that is bound and cleaved by a site-specific nuclease to introduce a double stranded break (or single-stranded nick) in the nucleic acid backbone of the polynucleotide sequence and/or its complementary DNA strand. A target site may comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. A "target site" for a RNA-guided nuclease may comprise the sequence of either complementary strand of a double-stranded nucleic acid (DNA) molecule or chromosome at the target site. A site-specific nuclease may bind to a target site, such as via a non-coding guide RNA (e.g., without being limiting, a CRISPR RNA (crRNA) or a single-guide RNA (sgRNA) as described further below). A non-coding guide RNA provided herein may be complementary to a target site (e.g., complementary to either strand of a double-stranded nucleic acid molecule or chromosome at the target site). It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA may be tolerated. A "target site" also refers to the polynucleotide sequence of a location within a plant genome that is bound and cleaved by a site-specific nuclease that has a specific targeting due to its molecular or protein structure and does not rely on a non-coding guide RNA molecule for site-specific targeting, such as a meganuclease, zinc finger nuclease (ZFN), or a TALEN, to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some embodiments a target region may be subjected to a mutation, deletion, insertion or inversion. The term "flanked" when used to describe a target region of a polynucleotide sequence or molecule, refers to two or more target sites of the polynucleotide sequence or molecule surrounding the target region, with one target site on each side of the target region.

As used herein, a "donor template", which may be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" may be used for site-directed integration of a DNA segment encoding an anti-sense sequence of interest, or as a template to introduce a mutation, such as an insertion, deletion, etc., into a target site within the genome of a plant. In an aspect, a donor template introduces a premature stop codon into a target site within the genome of a plant. A targeted genome editing technique provided herein may comprise the use of one or more, two or more, three or more, four or more, or five or more donor templates. A "donor template" may be a single-stranded or double-stranded DNA or RNA molecule or plasmid. An "insertion sequence" of a donor template is a sequence designed for targeted insertion into the genome of a plant cell, which may be of any suitable length. For example, the insertion sequence of a donor template may be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length. A donor template may also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site or region (e.g., flanking a target site or region) within the genome of the plant. When a donor template comprises homology arm(s) and an insertion sequence, the homology arm(s) will flank or surround the insertion sequence of the donor template. In an aspect, a donor template comprises a premature stop codon in a br2 nucleic acid sequence. In an aspect, a donor template comprises a mutation(s) or a missing exon, intron and/or coding sequence(s) of a br2 nucleic acid gene sequence to introduce a mutation or deletion into the br2 nucleic acid gene sequence. In an aspect, a donor template comprises at least one homology arm that targets an endogenous br2 locus.

A donor template may be linear or circular and may be single-stranded or double-stranded. A donor template may be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively. An insertion sequence of a donor template or insertion sequence provided herein may comprise a transcribable DNA sequence or segment that may be transcribed into all or a portion of an RNA molecule, such as a portion of a mRNA molecule. An insertion sequence of a donor template or insertion sequence provided herein may comprise a transcribable DNA sequence or segment that may be missing an exon, intron and/or coding sequence of a gene such that when the insertion sequence is integrated into the target site of the gene, all or part of a mRNA molecule transcribed from the mutant or edited gene will have the exon, intron and/or coding sequence missing or deleted.

As used herein, the terms "suppress," "suppression," "inhibit," "inhibition," "inhibiting", and "downregulation" with regard to expression of a target gene (e.g., an endogenous gene) refers to a lowering, reduction or elimination of the expression level and/or activity of a mRNA and/or protein encoded by the target gene in a plant, plant cell or plant tissue at one or more stage(s) of plant development, as compared to the expression level and/or activity of such target mRNA and/or protein in a wild-type or control plant, cell or tissue at the same stage(s) of plant development. A modified plant may have a br2 gene expression level and/or activity that is reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. A modified plant may have a br2 gene expression level and/or activity that is reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant. A modified plant may have a br2 mRNA level that is reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. A modified or transgenic plant may have a br2 mRNA expression level that is reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant. According to some embodiments, a modified plant may have a Br2 protein expression level and/or activity that is reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. According to some embodiments, a modified plant may have a Br2 protein expression level and/or activity that is reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

A wild-type genomic DNA sequence of the br2 locus from a reference genome of corn or maize is provided in SEQ ID NO: 1. A wild-type coding sequence (CDS) for the br2 locus from the reference genome is provided in SEQ ID NO: 2. A wild-type cDNA sequence for the br2 locus from the reference genome can be readily determined based on the CDS (SEQ ID NO: 2) along with the 5'UTR and 3'UTR identified below in reference to the br2 genomic locus (SEQ ID NO: 1). A wild-type amino acid sequence encoded by the br2 gene (for SEQ ID NO: 1 and 2) is provided in SEQ ID NO: 3. For the br2 genomic locus, nucleotides 1-954 of SEQ ID NO: 1 are upstream of the br2 5'-UTR; nucleotides 955-1000 of SEQ ID NO: 1 correspond to the 5'-UTR of the br2 gene; nucleotides 1001-1604 of SEQ ID NO: 1 correspond to the first exon of the br2 gene; nucleotides 1605-1747 of SEQ ID NO: 1 correspond to the first intron of the br2 gene; nucleotides 1748-2384 of SEQ ID NO: 1 correspond to the second exon of the br2 gene; nucleotides 2385-2473 of SEQ ID NO: 1 correspond to the second intron of the br2 gene; nucleotides 2474-2784 of SEQ ID NO: 1 correspond to the third exon of the br2 gene; nucleotides 2785-3410 of SEQ ID NO: 1 correspond to the third intron of the br2 gene; nucleotides 3411-3640 of SEQ ID NO: 1 correspond to the fourth exon of the br2 gene; nucleotides 3641-5309 of SEQ ID NO: 1 correspond to the fourth intron of the br2 gene; nucleotides 5310-7667 of SEQ ID NO: 1 correspond to the fifth exon of the br2 gene; and nucleotides 7668-8029 of SEQ ID NO: 1 correspond to the 3'-UTR of the br2 gene. SEQ ID NO: 1 also provides 638 nucleotides downstream of the 3'-UTR of the br2 gene (nucleotides 8030-8667 of SEQ ID NO: 1).

In an aspect, an endogenous or wild-type br2 locus or gene prior to being genetically modified comprises a nucleotide sequence that is at least 90% identical to SEQ ID NO: 1. In an aspect, an endogenous br2 locus or gene comprises a nucleotide sequence that is at least 91% identical to SEQ ID NO: 1. In an aspect, an endogenous br2 locus or gene comprises a nucleotide sequence that is at least 92% identical to SEQ ID NO: 1. In an aspect, an endogenous br2 locus or gene comprises a nucleotide sequence that is at least 93% identical to SEQ ID NO: 1. In an aspect, an endogenous br2 locus or gene comprises a nucleotide sequence that is at least 94% identical to SEQ ID NO: 1. In an aspect, an endogenous br2 locus or gene comprises a nucleotide sequence that is at least 95% identical to SEQ ID NO: 1. In an aspect, an endogenous br2 locus or gene comprises a nucleotide sequence that is at least 96% identical to SEQ ID NO: 1. In an aspect, an endogenous br2 locus or gene comprises a nucleotide sequence that is at least 97% identical to SEQ ID NO: 1. In an aspect, an endogenous br2 locus or gene comprises a nucleotide sequence that is at least 98% identical to SEQ ID NO: 1. In an aspect, an endogenous br2 locus or gene comprises a nucleotide sequence that is at least 99% identical to SEQ ID NO: 1. In an aspect, an endogenous br2 locus or gene comprises a nucleotide sequence that is 100% identical to SEQ ID NO: 1.

Brachytic2 (br2) is a homologue of the *Arabidopsis thaliana* gene ATP BINDING CASSETTE TYPE B1 (ABCB1) auxin transporter. See Knöller et al., *J. Exp. Botany,* 61:3689-3696 (2010). Br2 has been demonstrated to function in the export of auxin from intercalary meristems. See Knöller et al. Intercalary meristems form at the base of nodes and leaf blades in grasses such as corn. Without being limited by any theory, it has been hypothesized that auxin exported from intercalary meristems promotes the elongation of cells between nodes, allowing for rapid vertical growth of some grass species (e.g., corn). It has been shown that some recessive mutant alleles of br2 can be effective in achieving a short stature plant height in corn due to a shortening of the internode length without a corresponding reduction in the number of internodes or the number and size of other organs. See PCT Application No. PCT/US2016/029492, published as WO/2016/176286 and U.S. Pat. No. 10,472,684, respectively. However, these short stature phenotypes were observed with plants that were homozygous for a recessive br2 mutation. Thus, both parents must carry the recessive allele or mutation for the progeny or hybrid corn plant to have the short stature phenotype, although a small reduction in plant height has been observed in heterozygous plants depending on the mutant br2 allele. In contrast, the present disclosure describes br2 mutant alleles that can produce a short stature phenotype in corn or maize plants when present in a heterozygous state. These dominant or semi-dominant alleles of the br2 gene can be present in only one of the parent plants to produce the short stature phenotype in their progeny or hybrid plants, although such alleles may also be carried by both parents.

As understood in the art, a dominant allele of a gene is an allele that masks the contribution of a second allele of the gene (e.g., a wild-type allele or copy of the gene on the homologous chromosome) at the same locus. If the masking of the other allele is partial or incomplete, the dominant allele may be described as being semi-dominant. As used herein, a dominant allele(s) or trait(s) include(s) any semi-dominant allele(s) or trait(s) of a gene or locus. It is possible in some cases for a dominant allele at one locus to also have a dominant effect over a gene(s) or allele(s) at another locus/loci. Dominant negative alleles, or anti-morphs, are alleles that produce altered or modified gene products that act to oppose or reduce wild-type allelic function. For example, a dominant negative allele can reduce, abrogate or suppress the normal function of a wild-type allele or gene product in a heterozygous state.

A variety of mechanisms are possible for a dominant or semi-dominant allele (e.g., dominant negative allele) to exert its masking effect on another copy or allele for the same gene or locus. Without being limited by any theory, a mutant or edited allele of a br2 gene or locus may comprise a deletion of all or part of the br2 gene or locus and/or a premature stop codon in the coding sequence of the br2 gene or locus. Such deletion or premature stop codon may cause an altered or truncated Br2 protein or polypeptide fragment to be expressed, encoded and translated from the mutant or edited allele of a br2 gene or locus, which may not only have a loss-of-function but also interfere with the function and/or expression of a Br2 protein expressed from another copy or allele of the br2 gene or locus (e.g., a wild-type copy or allele of the br2 gene or locus) in a dominant or semi-dominant manner. Without being limited by theory, an altered or truncated Br2 protein expressed from a mutant or edited allele of a br2 gene or locus comprising a deletion of all or part of the br2 gene or locus and/or a premature stop codon in the coding sequence of the br2 gene or locus may interfere with the function and/or expression of a Br2 protein expressed from another copy or allele of the br2 gene or locus if the Br2 proteins bind to, or form complexes with, each other and/or other proteins, which can affect the function of the Br2 protein expressed from the other copy or allele of the br2 gene or locus.

The corn or maize full-length Br2 protein encoded by the wild-type Zm.br2 gene or locus has a bipartite structure and comprises two transmembrane domains (TMDs) and two nucleotide binding domains (NBDs) arranged (in the N-terminal to C-terminal direction) as TMD1-NBD1-TMD2-NBD2 with intracellular N-terminal and C-terminal regions and an intracellular linker sequence between the NBD1 and TMD2 domains. Each of the two transmembrane domains consists of six transmembrane segments or helices that traverse the plasma membrane including transmembrane segments 1-6 for TMD1 (SEQ ID Nos: 28-33) and transmembrane segments 7-12 for TMD2 (SEQ ID Nos: 40-45). Each of the two nucleotide binding domains consists of several functional motifs including (in the N-terminal to C-terminal direction) a Walker A, Q-Loop, ABC transport signature, Walker B, D-Loop, and H-Loop for NBD1 and NBD2 (SEQ ID Nos: 34-39 and 46-51, respectively), wherein the motifs of each NBD are separated by intervening sequences of different lengths. The coordinates of these domains, segments and motifs in reference to the wild-type Br2 protein sequence (SEQ ID NO: 3) and the corresponding nucleotide coordinates encoding these domains, segments and motifs in reference to the wild-type br2 coding sequence (SEQ ID NO: 2) are provided in Table 1 below. Sec, e.g., Dhaliwal, A. K. et al., *Frontiers in Plant Science,* 5 (657): 1-10 (2014). The full-length maize Br2 protein provided by SEQ ID NO: 3 is 1379 amino acids in length. Although the exon-intron junctions (and exon-exon junctions of the mature mRNA) can be determined from the description and annotation of the Zm.br2 genomic sequence above (SEQ ID NO: 1), these junctions in reference to the coding sequence (CDS) with introns removed (SEQ ID NO: 2) and the Zm.br2 protein sequence (SEQ ID NO: 3) are as follows: exon 1/exon 2 junction is between nucleotide positions 604 and 605 and at amino acid position 202; exon 2/exon 3 junction is between nucleotide positions 1241 and 1242 and at amino acid position 414; exon 3/exon 4 junction is between nucleotide positions 1552 and 1553 and at amino acid position 518; and exon 4/exon 5 junction is between nucleotide positions 1782 and 1783 and between amino acid positions 594 and 595. Indeed, a majority of the Zm.Br2 protein is encoded by exon 5 of the Zm.br2 gene. It is important to note, however, that the exact sequence definitions and boundaries for each of these domains, regions, segments and motifs may vary somewhat depending on the specific Br2 sequence, which may vary between different maize varieties or lines, and the particular criteria used to define these domains, regions, segments and motifs as understood in the art. See, e.g., uniprot.org (A0A2P1BTK0_MAIZE). It also worth noting that the Zm.br2 gene can produce two alternatively spliced transcripts including a main transcript that includes all five exons (T01) and encoding the full-length protein, and a second transcript lacking exon 5 (T02) and encoding only TMD1 and part of NBD1. See, e.g., Zhang, X. et al., *BMC Plant Biology,* 19:589 (2019).

TABLE 1

Amino Acid and Nucleotide Sequence Coordinates of Maize Br2 CDS and Protein.

| Structural Element | Protein Position Coordinates of SEQ ID NO: 3 | Protein Sequence (SEQ ID NO) | CDS Nucleotide Position Coordinates of SEQ ID NO: 2 |
|---|---|---|---|
| TMD1 | 137-421 | — | 409-1263 |
| TM Segment 1 | 137-159 | 28 | 409-477 |
| TM Segment 2 | 180-197 | 29 | 538-591 |
| TM Segment 3 | 264-283 | 30 | 790-849 |
| TM Segment 4 | 285-307 | 31 | 853-921 |
| TM Segment 5 | 370-392 | 32 | 1108-1176 |
| TM Segment 6 | 399-421 | 33 | 1195-1263 |
| NBD1 | 460-700 | — | 1378-2100 |
| Walker A | 496-503 | 34 | 1486-1509 |
| Q-Loop | 541-544 | 35 | 1621-1632 |
| ABC Transport | 602-611 | 36 | 1804-1833 |
| Walker B | 622-628 | 37 | 1864-1884 |
| D-Loop | 630-633 | 38 | 1888-1899 |

TABLE 1-continued

Amino Acid and Nucleotide Sequence Coordinates of Maize Br2 CDS and Protein.

| Structural Element | Protein Position Coordinates of SEQ ID NO: 3 | Protein Sequence (SEQ ID NO) | CDS Nucleotide Position Coordinates of SEQ ID NO: 2 |
|---|---|---|---|
| H-Loop | 655-660 | 39 | 1963-1980 |
| Linker | 701-797 | — | 2101-2391 |
| TMD2 | 805-1084 | — | 2413-3252 |
| TM Segment 7 | 805-827 | 40 | 2413-2481 |
| TM Segment 8 | 840-862 | 41 | 2518-2586 |
| TM Segment 9 | 918-940 | 42 | 2752-2820 |
| TM Segment 10 | 942-964 | 43 | 2824-2892 |
| TM Segment 11 | 1027-1049 | 44 | 3079-3147 |
| TM Segment 12 | 1062-1084 | 45 | 3184-3252 |
| NBD2 | 1120-1358 | — | 3357-4074 |
| Walker A | 1156-1163 | 46 | 3466-3489 |
| Q-Loop | 1201-1204 | 47 | 3600-3612 |
| ABC Transport | 1260-1269 | 48 | 3778-3807 |
| Walker B | 1280-1286 | 49 | 3838-3858 |
| D-Loop | 1288-1291 | 50 | 3862-3873 |
| H-Loop | 1313-1318 | 51 | 3937-3954 |

As provided herein, it has been surprisingly found that a novel mutant allele of the Zm.br2 gene having a premature stop codon and/or deletion that encodes a truncated Zm.Br2 protein comprising at least part of the TMD1 domain, but lacking the NBD1, TMD2 and NBD2 domains, produces a dominant or semi-dominant short stature phenotype in a heterozygous state with a wild-type Zm.br2 allele. Without being bound by theory, it is proposed that a truncated Zm.Br2 protein with all or part of TMD1 domain, but without the NBD1 and NBD2 domains (with likely deletion of the TMD2 domain), is able to become an integral protein with the plasma membrane of the plant cell and interact on a protein-protein level with a wild-type Br2 protein to interfere with its function and cause the dominant or semi-dominant short stature phenotype in a heterozygous plant. Without being bound by theory, it is further proposed that a truncated Zm.Br2 protein with all or part of TMD2 domain, but without the NBD1 and NBD2 domains (with possible inclusion or deletion of the TMD1 domain), may also be able to become an integral protein with the plasma membrane of the plant cell and interact on a protein-protein level with a wild-type Br2 protein to interfere with its function and cause the dominant or semi-dominant short stature phenotype in a heterozygous plant. Such a truncated Zm.Br2 protein may also comprise all or part of the N-terminal region, linker region, and/or C-terminal region as defined herein, or a truncated Zm.Br2 protein may not comprise all or part of the N-terminal region, linker region, and/or C-terminal region. Many of the Zm.br2 mutant alleles reported to date have generally been recessive mutations in intron 4 and exon 5 and include at least part of the NBD1 domain with perhaps only a small reduction in plant height in the heterozygous state. See PCT Application No. PCT/US2016/029492, published as WO/2016/176286, PCT/US2017/067888, published as WO2018/119225, and Bage, S. A. et al., *Plant Gene,* 21:100198 (2020).

According to embodiments of the present disclosure, an endogenous Zm.br2 gene can be edited or engineered in a corn or maize plant to express a truncated Zm.Br2 protein relative to a wild-type protein by the introduction of a premature stop codon into the coding sequence and the encoded mRNA transcript of the endogenous gene. Such mutation or edit in the endogenous Zm.br2 gene may comprise a substitution, deletion and/or insertion of one or more nucleotides. According to embodiments of the present disclosure, an endogenous Zm.br2 gene can be edited or engineered in a corn or maize plant to express a truncated Zm.Br2 protein relative to a wild-type protein by the introduction of a deletion into the coding sequence and the encoded mRNA transcript of the endogenous gene. Without being bound by theory, a truncated Br2 protein expressed from an edited endogenous br2 gene comprising a premature stop codon or deletion may not only be non-functional or have reduced function, but also interfere with the functioning of a wild-type Br2 protein encoded by the other copy of the Zm.br2 gene to act in a dominant or semi-dominant manner. In an aspect, a premature stop codon or deletion within an mRNA transcript results in translation of a truncated protein as compared to a control mRNA transcript that lacks the premature stop codon or deletion.

In an aspect, a premature stop codon can arise from a frameshift mutation. Frameshift mutations can be caused by the insertion and/or deletion of one or more nucleotides in a protein-coding sequence. In an aspect, a premature stop codon can arise from a nonsense mutation as a result of a substitution of one or more nucleotides to convert a codon encoding for an amino acid into a stop codon. A premature stop codon may be introduced by a frameshift mutation in the endogenous Zm.br2 gene that results in aberrant amino acid sequence being encoded downstream of the frameshift mutation until a stop codon is reached in the altered reading frame. As a result, a truncated Zm.Br2 protein resulting from a frameshift mutation may encode a truncated Zm.Br2 protein having a normal or in-frame amino acid sequence until the site or position of the frameshift mutation that causes an aberrant sequence of one or more amino acids starting at or immediately after the site of the frameshift mutation until a stop codon is reached in the altered reading frame. Alternatively, a premature stop codon may be introduced by a nonsense mutation in the endogenous Zm.br2 gene that results in a stop codon at the site of the nonsense mutation. As used herein, a “stop codon” refers to a nucleotide triplet within an mRNA transcript of a corn or maize plant cell that signals a termination of protein translation according to the genetic code of the corn or maize plant cell. A “premature stop codon” refers to a stop codon positioned earlier (e.g., on the 5'-side) than the normal stop codon position in an endogenous mRNA transcript. A stop codon is a nucleotide triplet in a mRNA that signals the termination of protein translation from the mRNA. Without being limiting, several stop codons are known in the art, including "UAG," "UAA," "UGA," "TAG," "TAA," and "TGA."

In an aspect, a nonsense or frameshift mutation provided herein is located in an exon of a br2 gene. In an aspect, a premature stop codon is positioned within the first exon of an endogenous br2 locus. In an aspect, a premature stop codon is positioned within the second exon of an endogenous br2 locus. In an aspect, a premature stop codon is positioned within the third exon of an endogenous br2 locus. In an aspect, a substitution, insertion or deletion provided herein, which may be a nonsense or frameshift mutation, comprises a deletion within or spanning one or more exon(s), one or more intron(s), and/or one or more intron/exon splice site(s). According to present embodiments, a premature stop codon or deletion may be introduced into the coding sequence of an endogenous br2 gene via a targeted editing technique and/or site-directed integration. The premature stop codon or deletion may be generated via imperfect DNA repair following a double strand break introduced into a br2 gene, or via template-assisted repair following introduction of the double strand break using a DNA donor template comprising the premature stop codon or deletion (i.e., lacking the sequence to be deleted). Such a DNA donor template may further comprise one or more flanking homologous arms or sequences that are identical, homologous or complementary to a corresponding sequence of the endogenous br2 gene to help promote recombination between the donor template and the target site in the endogenous br2 gene for insertion or recombination of a sequence comprising the premature stop codon or deletion at the desired target site.

According to embodiments of the present disclosure, a modified corn or maize plant or plant part is provided comprising a mutant allele of the endogenous br2 gene. Such mutant allele comprises a transmembrane sequence encoding at least one transmembrane segment of a transmembrane domain (TMD) of a Zm.Br2 protein but does not comprise and is lacking any sequence encoding a functional motif of a nucleotide binding domain (NBD) of a Zm.Br2 protein. The transmembrane sequence encoding at least one transmembrane segment of a transmembrane domain (TMD) of a Zm.Br2 protein is a polynucleotide or DNA sequence. In an aspect, a truncated Zm.Br2 protein encoded by a mutant allele of the endogenous br2 gene comprises at least one transmembrane segment of a transmembrane domain (TMD) of a Zm.Br2 protein but does not comprise and is lacking a functional motif of a nucleotide binding domain (NBD) of a Zm.Br2 protein. As used herein, the phrase "does not comprise" with respect to an element or feature means that the element or feature is not present and is absent (i.e., the subject lacks the element or feature). According to some embodiments, a mutant allele of the endogenous br2 gene comprises a transmembrane sequence encoding at least two transmembrane segments, at least three transmembrane segments, at least four transmembrane segments, at least five transmembrane segments, or at least six transmembrane segments of a transmembrane domain (TMD) of a Zm.Br2 protein. In an aspect, a truncated Zm.Br2 protein encoded by a mutant allele of the endogenous br2 gene comprises at least two transmembrane segments, at least three transmembrane segments, at least four transmembrane segments, at least five transmembrane segments, or at least six transmembrane segments of a transmembrane domain (TMD) of a Zm.Br2 protein.

According to some embodiments, a mutant allele of the endogenous br2 gene comprises a transmembrane sequence encoding one or more of transmembrane segments 1-6 of TMD1 of a Zm.Br2 protein or one or more of transmembrane segments 7-12 of TMD2 of a Zm.Br2 protein. In an aspect, a truncated Zm.Br2 protein encoded by a mutant allele of the endogenous br2 gene comprises one or more of transmembrane segments 1-6 of TMD1 of a Zm.Br2 protein or one or more of transmembrane segments 7-12 of TMD2 of a Zm.Br2 protein. According to some embodiments, such mutant allele of the endogenous br2 gene comprises a transmembrane sequence encoding a transmembrane domain that is at least 80%, at least 90%, at least 95%, or 100% identical to amino acids 137-421 of SEQ ID NO: 3 or at least 80%, at least 90%, at least 95%, or 100% identical to amino acids 805-1084 of SEQ ID NO: 3. In an aspect, a truncated Zm.Br2 protein encoded by a mutant allele of the endogenous br2 gene comprises a transmembrane domain that is at least 80%, at least 90%, at least 95%, or 100% identical to amino acids 137-421 of SEQ ID NO: 3 or at least 80%, at least 90%, at least 95%, or 100% identical to amino acids 805-1084 of SEQ ID NO: 3.

According to some embodiments, a mutant allele of the endogenous br2 gene comprises a transmembrane sequence encoding a first transmembrane segment that is at least 80%, at least 90%, at least 95%, or 100% identical to SEQ ID NO: 28 or 40, a second transmembrane segment that is at least 80%, at least 90%, at least 95%, or 100% identical to SEQ ID NO: 29 or 41, a third transmembrane segment that is at least 80%, at least 90%, at least 95%, or 100% identical to SEQ ID NO: 30 or 42, a fourth transmembrane segment that is at least 80%, at least 90%, at least 95%, or 100% identical to SEQ ID NO: 31 or 43, a fifth transmembrane segment that is at least 80%, at least 90%, at least 95%, or 100% identical to SEQ ID NO: 32 or 44, and/or a sixth transmembrane segment that is at least 80%, at least 90%, at least 95%, or 100% identical to SEQ ID NO: 33 or 45. In an aspect, a truncated Zm.Br2 protein encoded by a mutant allele of the endogenous br2 gene comprises a first transmembrane segment that is at least 80%, at least 90%, at least 95%, or 100% identical to SEQ ID NO: 28 or 40, a second transmembrane segment that is at least 80%, at least 90%, at least 95%, or 100% identical to SEQ ID NO: 29 or 41, a third transmembrane segment that is at least 80%, at least 90%, at least 95%, or 100% identical to SEQ ID NO: 30 or 42, a fourth transmembrane segment that is at least 80%, at least 90%, at least 95%, or 100% identical to SEQ ID NO: 31 or 43, a fifth transmembrane segment that is at least 80%, at least 90%, at least 95%, or 100% identical to SEQ ID NO: 32 or 44, and/or a sixth transmembrane segment that is at least 80%, at least 90%, at least 95%, or 100% identical to SEQ ID NO: 33 or 45.

According to some embodiments, a mutant allele of the endogenous br2 gene comprises (i) a first transmembrane sequence encoding a first transmembrane domain comprising a first transmembrane segment that is at least 80%, at least 90%, at least 95%, or 100% identical to SEQ ID NO: 28, a second transmembrane segment that is at least 80%, at least 90%, at least 95%, or 100% identical to SEQ ID NO: 29, a third transmembrane segment that is at least 80%, at least 90%, at least 95%, or 100% identical to SEQ ID NO: 30, a fourth transmembrane segment that is at least 80%, at least 90%, at least 95%, or 100% identical to SEQ ID NO: 31, a fifth transmembrane segment that is at least 80%, at least 90%, at least 95%, or 100% identical to SEQ ID NO: 32, and/or a sixth transmembrane segment that is at least 80%, at least 90%, at least 95%, or 100% identical to SEQ ID NO: 33, and (ii) a second transmembrane sequence encoding a second transmembrane domain comprising a seventh transmembrane segment that is at least 80%, at least 90%, at least 95%, or 100% identical to SEQ ID NO: 40, an eighth transmembrane segment that is at least 80%, at least 90%, at least 95%, or 100% identical to SEQ ID NO: 41, a ninth transmembrane segment that is at least 80%, at least 90%, at least 95%, or 100% identical to SEQ ID NO: 42, a tenth transmembrane segment that is at least 80%, at least 90%, at least 95%, or 100% identical to SEQ ID NO: 43, an eleventh transmembrane segment that is at least 80%, at least 90%, at least 95%, or 100% identical to SEQ ID NO: 44, and/or a twelfth transmembrane segment that is at least 80%, at least 90%, at least 95%, or 100% identical to SEQ ID NO: 45.

In an aspect, a truncated Zm.Br2 protein encoded by a mutant allele of the endogenous br2 gene comprises (i) a first transmembrane domain comprising a first transmembrane segment that is at least 80%, at least 90%, at least 95%, or 100% identical to SEQ ID NO: 28, a second transmembrane segment that is at least 80%, at least 90%, at least 95%, or 100% identical to SEQ ID NO: 29, a third transmembrane segment that is at least 80%, at least 90%, at least 95%, or 100% identical to SEQ ID NO: 30, a fourth transmembrane segment that is at least 80%, at least 90%, at least 95%, or 100% identical to SEQ ID NO: 31, a fifth transmembrane segment that is at least 80%, at least 90%, at least 95%, or 100% identical to SEQ ID NO: 32, and/or a sixth transmembrane segment that is at least 80%, at least 90%, at least 95%, or 100% identical to SEQ ID NO: 33, and (ii) a second transmembrane domain comprising a seventh transmembrane segment that is at least 80%, at least 90%, at least 95%, or 100% identical to SEQ ID NO: 40, an eighth transmembrane segment that is at least 80%, at least 90%, at least 95%, or 100% identical to SEQ ID NO: 41, a ninth transmembrane segment that is at least 80%, at least 90%, at least 95%, or 100% identical to SEQ ID NO: 42, a tenth transmembrane segment that is at least 80%, at least 90%, at least 95%, or 100% identical to SEQ ID NO: 43, an eleventh transmembrane segment that is at least 80%, at least 90%, at least 95%, or 100% identical to SEQ ID NO: 44, and/or a twelfth transmembrane segment that is at least 80%, at least 90%, at least 95%, or 100% identical to SEQ ID NO: 45.

According to some embodiments, a mutant allele of the endogenous br2 gene comprises a transmembrane sequence encoding a transmembrane domain that is at least 80%, at least 90%, at least 95%, or 100% identical to amino acids 137-197 of SEQ ID NO: 3, amino acids 137-283 of SEQ ID NO: 3, amino acids 137-307 of SEQ ID NO: 3, amino acids 137-392 of SEQ ID NO: 3, amino acids 137-421 of SEQ ID NO: 3, amino acids 180-283 of SEQ ID NO: 3, amino acids 180-307 of SEQ ID NO: 3, amino acids 180-392 of SEQ ID NO: 3, amino acids 180-421 of SEQ ID NO: 3, amino acids 264-307 of SEQ ID NO: 3, amino acids 264-392 of SEQ ID NO: 3, amino acids 264-421 of SEQ ID NO: 3, amino acids 285-392 of SEQ ID NO: 3, amino acids 285-421 of SEQ ID NO: 3, or amino acids 370-421 of SEQ ID NO: 3. According to some embodiments, a mutant allele of the endogenous br2 gene comprises a transmembrane sequence encoding a transmembrane domain that is at least 80%, at least 90%, at least 95%, or 100% identical to amino acids 805-862 of SEQ ID NO: 3, amino acids 805-940 of SEQ ID NO: 3, amino acids 805-964 of SEQ ID NO: 3, amino acids 805-1049 of SEQ ID NO: 3, amino acids 805-1084 of SEQ ID NO: 3, amino acids 840-940 of SEQ ID NO: 3, amino acids 840-964 of SEQ ID NO: 3, amino acids 840-1049 of SEQ ID NO: 3, amino acids 840-1084 of SEQ ID NO: 3, amino acids 918-964 of SEQ ID NO: 3, amino acids 918-1049 of SEQ ID NO: 3, amino acids 918-1084 of SEQ ID NO: 3, amino acids 942-1049 of SEQ ID NO: 3, amino acids 942-1084 of SEQ ID NO: 3, or amino acids 1027-1084 of SEQ ID NO: 3.

In an aspect, a truncated Zm.Br2 protein encoded by a mutant allele of the endogenous br2 gene comprises a transmembrane domain that is at least 80%, at least 90%, at least 95%, or 100% identical to amino acids 137-197 of SEQ ID NO: 3, amino acids 137-283 of SEQ ID NO: 3, amino acids 137-307 of SEQ ID NO: 3, amino acids 137-392 of SEQ ID NO: 3, amino acids 137-421 of SEQ ID NO: 3, amino acids 180-283 of SEQ ID NO: 3, amino acids 180-307 of SEQ ID NO: 3, amino acids 180-392 of SEQ ID NO: 3, amino acids 180-421 of SEQ ID NO: 3, amino acids 264-307 of SEQ ID NO: 3, amino acids 264-392 of SEQ ID NO: 3, amino acids 264-421 of SEQ ID NO: 3, amino acids 285-392 of SEQ ID NO: 3, amino acids 285-421 of SEQ ID NO: 3, or amino acids 370-421 of SEQ ID NO: 3. In an aspect, a truncated Zm.Br2 protein encoded by a mutant allele of the endogenous br2 gene comprises a transmembrane domain that is at least 80%, at least 90%, at least 95%, or 100% identical to amino acids 805-862 of SEQ ID NO: 3, amino acids 805-940 of SEQ ID NO: 3, amino acids 805-964 of SEQ ID NO: 3, amino acids 805-1049 of SEQ ID NO: 3, amino acids 805-1084 of SEQ ID NO: 3, amino acids 840-940 of SEQ ID NO: 3, amino acids 840-964 of SEQ ID NO: 3, amino acids 840-1049 of SEQ ID NO: 3, amino acids 840-1084 of SEQ ID NO: 3, amino acids 918-964 of SEQ ID NO: 3, amino acids 918-1049 of SEQ ID NO: 3, amino acids 918-1084 of SEQ ID NO: 3, amino acids 942-1049 of SEQ ID NO: 3, amino acids 942-1084 of SEQ ID NO: 3, or amino acids 1027-1084 of SEQ ID NO: 3.

According to some embodiments, a mutant allele of the endogenous br2 gene comprises (i) a first transmembrane sequence encoding a first transmembrane domain that is at least 80%, at least 90%, at least 95%, or 100% identical to amino acids 137-197 of SEQ ID NO: 3, amino acids 137-283 of SEQ ID NO: 3, amino acids 137-307 of SEQ ID NO: 3, amino acids 137-392 of SEQ ID NO: 3, amino acids 137-421 of SEQ ID NO: 3, amino acids 180-283 of SEQ ID NO: 3, amino acids 180-307 of SEQ ID NO: 3, amino acids 180-392 of SEQ ID NO: 3, amino acids 180-421 of SEQ ID NO: 3, amino acids 264-307 of SEQ ID NO: 3, amino acids 264-392 of SEQ ID NO: 3, amino acids 264-421 of SEQ ID NO: 3, amino acids 285-392 of SEQ ID NO: 3, amino acids 285-421 of SEQ ID NO: 3, or amino acids 370-421 of SEQ ID NO: 3, and (ii) a second transmembrane sequence encoding a second transmembrane domain that is at least 80%, at least 90%, at least 95%, or 100% identical to amino acids 805-862 of SEQ ID NO: 3, amino acids 805-940 of SEQ ID NO: 3, amino acids 805-964 of SEQ ID NO: 3, amino acids 805-1049 of SEQ ID NO: 3, amino acids 805-1084 of SEQ ID NO: 3, amino acids 840-940 of SEQ ID NO: 3, amino acids 840-964 of SEQ ID NO: 3, amino acids 840-1049 of SEQ ID NO: 3, amino acids 840-1084 of SEQ ID NO: 3, amino acids 918-964 of SEQ ID NO: 3, amino acids 918-1049 of SEQ ID NO: 3, amino acids 918-1084 of SEQ ID NO: 3, amino acids 942-1049 of SEQ ID NO: 3, amino acids 942-1084 of SEQ ID NO: 3, or amino acids 1027-1084 of SEQ ID NO: 3.

In an aspect, a truncated Zm.Br2 protein encoded by a mutant allele of the endogenous br2 gene comprises (i) a first transmembrane domain that is at least 80%, at least 90%, at least 95%, or 100% identical to amino acids 137-197 of SEQ ID NO: 3, amino acids 137-283 of SEQ ID NO: 3, amino acids 137-307 of SEQ ID NO: 3, amino acids 137-392 of SEQ ID NO: 3, amino acids 137-421 of SEQ ID NO: 3, amino acids 180-283 of SEQ ID NO: 3, amino acids 180-307 of SEQ ID NO: 3, amino acids 180-392 of SEQ ID NO: 3, amino acids 180-421 of SEQ ID NO: 3, amino acids 264-307 of SEQ ID NO: 3, amino acids 264-392 of SEQ ID NO: 3, amino acids 264-421 of SEQ ID NO: 3, amino acids 285-392 of SEQ ID NO: 3, amino acids 285-421 of SEQ ID NO: 3, or amino acids 370-421 of SEQ ID NO: 3, and (ii) a second transmembrane domain that is at least 80%, at least 90%, at least 95%, or 100% identical to amino acids 805-862 of SEQ ID NO: 3, amino acids 805-940 of SEQ ID NO: 3, amino acids 805-964 of SEQ ID NO: 3, amino acids 805-1049 of SEQ ID NO: 3, amino acids 805-1084 of SEQ ID NO: 3, amino acids 840-940 of SEQ ID NO: 3, amino acids 840-964 of SEQ ID NO: 3, amino acids 840-1049 of SEQ ID NO: 3, amino acids 840-1084 of SEQ ID NO: 3, amino acids 918-964 of SEQ ID NO: 3, amino acids 918-1049 of SEQ ID NO: 3, amino acids 918-1084 of SEQ ID NO: 3, amino acids 942-1049 of SEQ ID NO: 3, amino acids 942-1084 of SEQ ID NO: 3, or amino acids 1027-1084 of SEQ ID NO: 3.

According to embodiments of the present disclosure, a mutant allele of the endogenous br2 gene does not comprise a polynucleotide sequence encoding a nucleotide binding domain (NBD) or a nucleotide binding domain (NBD) motif or a polypeptide sequence that is at least 80%, at least 90%, at least 95%, or 100% identical to amino acids 460-700 or 496-660 of SEQ ID NO: 3 or at least 80%, at least 90%, at least 95%, or 100% identical to amino acids 1120-1358 or 1156-1318 of SEQ ID NO: 3. In an aspect, a truncated Br2 protein encoded by a mutant allele of the endogenous br2 gene does not comprise a nucleotide binding domain (NBD), a nucleotide binding domain (NBD) motif, or a polypeptide sequence that is at least 80%, at least 90%, at least 95%, or 100% identical to amino acids 460-700 or 496-660 of SEQ ID NO: 3 or at least 80%, at least 90%, at least 95%, or 100% identical to amino acids 1120-1358 or 1156-1318 of SEQ ID NO: 3.

According to embodiments of the present disclosure, a mutant allele of the endogenous br2 gene does not comprise and is lacking a polynucleotide sequence encoding a Walker A, a Q-Loop, an ABC Transport, a Walker B, a D-Loop, or a H-Loop motif of a nucleotide binding domain (NBD). In an aspect, a truncated Br2 protein encoded by a mutant allele of the endogenous br2 gene does not comprise and is lacking a Walker A, a Q-Loop, an ABC Transport, a Walker B, a D-Loop, or a H-Loop motif of a nucleotide binding domain (NBD). According to embodiments of the present disclosure, a mutant allele of the endogenous br2 gene does not comprise a polynucleotide sequence encoding a nucleotide binding domain (NBD) motif that is at least 80%, at least 90%, at least 95%, or 100% identical to any one of SEQ ID NOs: 34-39. In an aspect, a truncated Br2 protein encoded by a mutant allele of the endogenous br2 gene does not comprise a nucleotide binding domain (NBD) motif that is at least 80%, at least 90%, at least 95%, or 100% identical to any one of SEQ ID NOs: 34-39. According to embodiments of the present disclosure, a mutant allele of the endogenous br2 gene does not comprise a polynucleotide sequence encoding a nucleotide binding domain (NBD) motif that is at least 80%, at least 90%, at least 95%, or 100% identical to any one of SEQ ID NOs: 46-51. In an aspect, a truncated Br2 protein encoded by a mutant allele of the endogenous br2 gene does not comprise a nucleotide binding domain (NBD) motif that is at least 80%, at least 90%, at least 95%, or 100% identical to any one of SEQ ID NOS: 46-51.

According to embodiments of the present disclosure, a mutant allele of the endogenous br2 gene does not comprise and is lacking all or part of a polynucleotide sequence(s) encoding a N-terminal region, a Linker region, and/or a C-terminal region. In an aspect, a truncated Br2 protein encoded by a mutant allele of the endogenous br2 gene does not comprise and is lacking all or part of a N-terminal region, a Linker region, and/or a C-terminal region.

In an aspect, a mutant allele provided herein encodes a truncated protein as compared to SEQ ID NO: 3. As used herein, a "truncated" protein or polypeptide comprises at least one fewer amino acid(s) as compared to an endogenous or wild-type protein or polypeptide, which may result from the introduction of a premature stop codon and/or a deletion in the coding region of the gene. In general terms, if an endogenous a protein comprises 100 amino acids, a truncated version of the protein can comprise between 1 and 99 identical amino acids. However, a truncated Zm.Br2 protein as provided herein does not comprise most or all of a nucleotide binding domain (NBD) and does not comprise a nucleotide binding domain (NBD) motif as described herein. It is also possible that a truncated protein may comprise an additional amino acid sequence that is not identical to the amino acid sequence of a corresponding wild-type Zm.Br2 protein, which may be introduced by an insertion or frameshift mutation.

In an aspect, this disclosure provides a modified corn plant, or plant part thereof, comprising a premature stop codon or deletion within a nucleic acid sequence encoding a Brachytic2 protein as compared to a nucleic acid sequence of a control corn plant or plant part thereof. In an aspect, this disclosure provides a modified corn plant, or plant part thereof, comprising a premature stop codon or deletion within a nucleic acid sequence encoding a Brachytic2 protein. In an aspect, this disclosure provides a modified corn plant, or plant part thereof, comprising a truncated Brachytic2 protein encoded by a nucleic acid sequence comprising a premature stop codon or deletion as compared to a wildtype or control nucleic acid sequence. In an aspect, this disclosure provides a modified corn plant, or plant part thereof, comprising a premature stop codon or deletion in a nucleic acid sequence as compared to SEQ ID NO: 1 or 2. In an aspect, a premature stop codon is positioned within a region of a br2 mRNA transcript selected from the group consisting of the first exon, the second exon, and the third exon, or a combination thereof.

In an aspect, a truncated Br2 protein sequence comprises a length of fewer than 1378 amino acids. In an aspect, a truncated Br2 protein sequence comprises a length of fewer than 1375 amino acids. In an aspect, a truncated Br2 protein sequence comprises a length of fewer than 1350 amino acids. In an aspect, a truncated Br2 protein sequence comprises a length of fewer than 1300 amino acids. In an aspect, a truncated Br2 protein sequence comprises a length of fewer than 1250 amino acids. In an aspect, a truncated Br2 protein sequence comprises a length of fewer than 1200 amino acids. In an aspect, a truncated Br2 protein sequence comprises a length of fewer than 1150 amino acids. In an aspect, a truncated Br2 protein sequence comprises a length of fewer than 1100 amino acids. In an aspect, a truncated Br2 protein sequence comprises a length of fewer than 1050 amino acids. In an aspect, a truncated Br2 protein sequence comprises a length of fewer than 1000 amino acids. In an aspect, a truncated Br2 protein sequence comprises a length of fewer than 950 amino acids. In an aspect, a truncated Br2 protein sequence comprises a length of fewer than 900 amino acids. In an aspect, a truncated Br2 protein sequence comprises a length of fewer than 850 amino acids. In an aspect, a truncated Br2 protein sequence comprises a length of fewer than 800 amino acids. In an aspect, a truncated Br2 protein sequence comprises a length of fewer than 750 amino acids. In an aspect, a truncated Br2 protein sequence comprises a length of fewer than 700 amino acids. In an aspect, a truncated Br2 protein sequence comprises a length of fewer than 650 amino acids. In an aspect, a truncated Br2 protein sequence comprises a length of fewer than 600 amino acids. In an aspect, a truncated Br2 protein sequence comprises a length of fewer than 550 amino acids. In an aspect, a truncated Br2 protein sequence comprises a length of fewer than 500 amino acids, fewer than 499 amino acids, fewer than 498 amino acids, fewer than 497 amino acids, fewer than 496 amino acids, fewer than 495 amino acids, fewer than 490 amino acids, fewer than 485 amino acids, fewer than 480 amino acids, fewer than 475 amino acids, fewer than 470 amino acids, fewer than 465 amino acids, fewer than 460 amino acids, fewer than 455 amino acids, fewer than 450 amino acids, fewer than 445 amino acids, fewer than 440 amino acids, fewer than 435 amino acids, fewer than 430 amino acids, fewer than 425 amino acids, fewer than 420 amino acids, fewer than 415 amino acids, fewer than 410 amino acids, or fewer than 405 amino acids. In an aspect, a truncated Br2 protein sequence comprises a length of fewer than 400 amino acids, fewer than 395 amino acids, fewer than 390 amino acids, fewer than 385 amino acids, fewer than 380 amino acids, fewer than 375 amino acids, fewer than 370 amino acids, fewer than 365 amino acids, fewer than 360 amino acids, fewer than 355 amino acids, fewer than 350 amino acids, fewer than 345 amino acids, fewer than 340 amino acids, fewer than 335 amino acids, fewer than 330 amino acids, fewer than 325 amino acids, fewer than 320 amino acids, fewer than 315 amino acids, fewer than 310 amino acids, or fewer than 305 amino acids. In an aspect, a truncated Br2 protein sequence comprises a length of fewer than 300 amino acids, fewer than 295 amino acids, fewer than 290 amino acids, fewer than 285 amino acids, fewer than 280 amino acids, fewer than 275 amino acids, fewer than 270 amino acids, fewer than 265 amino acids, fewer than 260 amino acids, fewer than 255 amino acids, fewer than 250 amino acids, fewer than 245 amino acids, fewer than 240 amino acids, fewer than 235 amino acids, fewer than 230 amino acids, fewer than 225 amino acids, fewer than 220 amino acids, fewer than 215 amino acids, fewer than 210 amino acids, or fewer than 205 amino acids. In an aspect, a truncated Br2 protein sequence comprises a length of fewer than 200 amino acids, fewer than 195 amino acids, fewer than 190 amino acids, fewer than 185 amino acids, fewer than 180 amino acids, fewer than 175 amino acids, fewer than 170 amino acids, fewer than 165 amino acids, fewer than 160 amino acids, fewer than 155 amino acids, fewer than 150 amino acids, fewer than 145 amino acids, fewer than 140 amino acids, fewer than 135 amino acids, fewer than 130 amino acids, fewer than 125 amino acids, fewer than 120 amino acids, fewer than 115 amino acids, fewer than 110 amino acids, or fewer than 105 amino acids. In an aspect, a truncated Br2 protein sequence comprises a length of fewer than 100 amino acids. In an aspect, a truncated Br2 protein sequence comprises fewer than 75 amino acids. In an aspect, a truncated Br2 protein sequence comprises a length of fewer than 50 amino acids.

While a truncated Br2 protein as provided herein does not comprise most or all of a nucleotide binding domain (NBD) and does not comprise a nucleotide binding domain (NBD) motif as described herein, a truncated Br2 protein does comprise at least one transmembrane segment of a transmembrane domain. Therefore, a truncated Br2 protein must have at least a minimal number of amino acids. In an aspect, a truncated Br2 protein sequence comprises a length of more than 15 amino acids. In an aspect, a truncated Br2 protein sequence comprises a length of more than 20 amino acids. In an aspect, a truncated Br2 protein sequence comprises a length of more than 30 amino acids. In an aspect, a truncated Br2 protein sequence comprises a length of more than 40 amino acids. In an aspect, a truncated Br2 protein sequence comprises a length of more than 50 amino acids. In an aspect, a truncated Br2 protein sequence comprises a length of more than 60 amino acids. In an aspect, a truncated Br2 protein sequence comprises a length of more than 70 amino acids. In an aspect, a truncated Br2 protein sequence comprises a length of more than 80 amino acids. In an aspect, a truncated Br2 protein sequence comprises a length of more than 90 amino acids. In an aspect, a truncated Br2 protein sequence comprises a length of more than 100 amino acids. In an aspect, a truncated Br2 protein sequence comprises a length of more than 110 amino acids. In an aspect, a truncated Br2 protein sequence comprises a length of more than 120 amino acids. In an aspect, a truncated Br2 protein sequence comprises a length of more than 130 amino acids. In an aspect, a truncated Br2 protein sequence comprises a length of more than 140 amino acids. In an aspect, a truncated Br2 protein sequence comprises a length of more than 150 amino acids. In an aspect, a truncated Br2 protein sequence comprises a length of more than 160 amino acids. In an aspect, a truncated Br2 protein sequence comprises a length of more than 170 amino acids. In an aspect, a truncated Br2 protein sequence comprises a length of more than 180 amino acids. In an aspect, a truncated Br2 protein sequence comprises a length of more than 190 amino acids. In an aspect, a truncated Br2 protein sequence comprises a length of more than 200 amino acids, more than 210 amino acids, more than 220 amino acids, more than 230 amino acids, more than 240 amino acids, more than 250 amino acids, more than 260 amino acids, more than 270 amino acids, more than 280 amino acids, or more than 290 amino acids. In an aspect, a truncated Br2 protein sequence comprises a length of more than 300 amino acids, more than 310 amino acids, more than 320 amino acids, more than 330 amino acids, more than 340 amino acids, more than 350 amino acids, more than 360 amino acids, more than 370 amino acids, more than 380 amino acids, or more than 390 amino acids. In an aspect, a truncated Br2 protein sequence comprises a length of more than 400 amino acids, more than 410 amino acids, more than 420 amino acids, more than 430 amino acids, more than 440 amino acids, more than 450 amino acids, or more than 475 amino acids. In an aspect, a truncated Br2 protein sequence comprises a length of more than 500 amino acids, more than 550 amino acids, more than 600 amino acids, more than 650 amino acids, more than 700 amino acids, more than 750 amino acids, more than 800 amino acids, more than 850 amino acids, more than 900 amino acids, more than 950 amino acids, or more than 1000 amino acids.

In an aspect, a truncated Br2 protein sequence comprises between 15 amino acid and 1000 amino acids. In an aspect, a truncated Br2 protein sequence comprises between 25 amino acids and 750 amino acids. In an aspect, a truncated Br2 protein sequence comprises between 50 amino acids and 750 amino acids. In an aspect, a truncated Br2 protein sequence comprises between 100 amino acids and 750 amino acids. In an aspect, a truncated Br2 protein sequence comprises between 100 amino acids and 500 amino acids. In an aspect, a truncated Br2 protein sequence comprises between 125 amino acids and 500 amino acids. In an aspect, a truncated Br2 protein sequence comprises between 150 amino acids and 500 amino acids. In an aspect, a truncated Br2 protein sequence comprises between 175 amino acids and 500 amino acids. In an aspect, a truncated Br2 protein sequence comprises between 200 amino acids and 500 amino acids. In an aspect, a truncated Br2 protein sequence comprises between 100 amino acids and 495 amino acids. In an aspect, a truncated Br2 protein sequence comprises between 200 amino acids and 495 amino acids. In an aspect, a truncated Br2 protein sequence comprises between 15 amino acids and 300 amino acids. In an aspect, a truncated Br2 protein sequence comprises between 15 amino acids and 250 amino acids. In an aspect, a truncated Br2 protein sequence comprises between 15 amino acids and 200 amino acids. In an aspect, a truncated Br2 protein sequence comprises between 15 amino acids and 150 amino acids. In an aspect, a truncated Br2 protein sequence comprises between 15 amino acids and 100 amino acids. In an aspect, a truncated Br2 protein sequence comprises between 15 amino acids and 75 amino acids. In an aspect, a truncated Br2 protein sequence comprises between 15 amino acids and 50 amino acids. In an aspect, a truncated Br2 protein sequence comprises between 50 amino acids and 500 amino acids. In an aspect, a truncated Br2 protein sequence comprises between 50 amino acids and 450 amino acids. In an aspect, a truncated Br2 protein sequence comprises between 50 amino acids and 400 amino acids. In an aspect, a truncated Br2 protein sequence comprises between 50 amino acids and 350 amino acids. In an aspect, a truncated Br2 protein sequence comprises between 50 amino acids and 300 amino acids. In an aspect, a truncated Br2 protein sequence comprises an amino acid length between any combination of minimum and maximum numbers of amino acids as provided herein and above.

As provided herein, a truncated Br2 protein encoded by a mutant allele of an endogenous br2 gene comprises a transmembrane domain (TMD) comprising at least one transmembrane segment but does not comprise a functional nucleotide binding domain (NBD) or a nucleotide binding domain (NBD) motif of a Zm.Br2 protein, such as a Walker A, a Q-Loop, an ABC Transport, a Walker B, a D-Loop, or a H-Loop motif. Thus, a mutant allele of an endogenous Zm.br2 gene comprises a mutation or edit that removes any polynucleotide sequence(s) encoding a functional nucleotide binding domain (NBD) or a nucleotide binding domain (NBD) motif of a Zm.Br2 protein. Accordingly, a mutant allele of an endogenous Zm.br2 gene will either have (i) a deletion(s) removing the polynucleotide sequence(s) of the endogenous Zm.br2 gene encoding most or all of the nucleotide binding domains (NBDs) and all nucleotide binding domain (NBD) motifs, or (ii) a premature stop codon upstream of the nucleotide binding domains (NBDs) or at least all of the nucleotide binding domain (NBD) motifs (i.e., on the N-terminal and 5' side of the nucleotide binding domains (NBDs) or the nucleotide binding domain (NBD) motifs). The deletion or premature stop codon of the mutant allele of the endogenous Zm.br2 gene can be introduced by a mutagenesis or genome editing technique.

According to some embodiments, to introduce a premature stop codon upstream of a polynucleotide sequence of a Zm.br2 gene encoding all or part of a nucleotide binding domain of the Br2 protein, such as the first nucleotide binding domain of the Br2 protein, at least one target site for introducing a mutation or edit using a genome editing technique that can give rise to the premature stop codon is upstream of such polynucleotide sequence. According to some embodiments, to introduce a premature stop codon upstream of a polynucleotide sequence of a Zm.br2 gene encoding all or part of a nucleotide binding domain, a first target site for introducing the premature stop codon using a genome editing technique may be upstream of such polynucleotide sequence, and a second target site for introducing the premature stop codon using a genome editing technique may be upstream or downstream of such polynucleotide sequence. In an aspect, a premature stop codon may be introduced into a polynucleotide sequence of a Zm.br2 gene by a nonsense or frameshift mutation, which may comprise a deletion, insertion and/or substitution of one or more nucleotides. According to some embodiments, to introduce a deletion of a polynucleotide sequence of a Zm.br2 gene encoding all or part of a nucleotide binding domain, at least one target site for introducing the deletion using a genome editing technique may be upstream of such polynucleotide sequence. According to some embodiments, to introduce a deletion of a polynucleotide sequence encoding all or part of a nucleotide binding domain, a first target site for introducing the deletion using a genome editing technique may be upstream of such polynucleotide sequence, and a second target site for introducing the deletion using a genome editing technique may be downstream of such polynucleotide sequence. Indeed, a targeted polynucleotide deletion may be introduced into an endogenous Zm.br2 gene corresponding to a target region flanked by two target sites for guide RNA(s) and/or a site-specific nuclease(s) using a genome editing technique.

The nucleotide positions or coordinates of the exon-exon junctions of the coding sequence (CDS) of a Zm.br2 gene in reference to SEQ ID NO: 2 and the corresponding amino acid positions or coordinates of a Zm.Br2 protein in reference to SEQ ID NO: 3 are provided above. The amino acid positions, coordinates and ranges for the transmembrane and nucleotide binding domains and motifs of a Zm.Br2 protein are also provided in Table 1 above, and the nucleotide positions, coordinates and ranges of the polynucleotide sequences of a Zm.br2 gene encoding these transmembrane and nucleotide binding domains and motifs of the Zm.Br2 protein can be readily determined based on the number of corresponding triplet polynucleotide codons and are also provided in Table 1 above. By relating these nucleotide and amino acid positions and coordinates: exon 1 of the Zm.br2 gene encodes the N-terminal region of the Zm.Br2 protein and a first portion of the first transmembrane domain (TMD1) of the Zm.Br2 protein including the transmembrane segment 1 and transmembrane segment 2; exon 2 of the Zm.br2 gene encodes a second portion of the first transmembrane domain (TMD1) of the Zm.Br2 protein including the transmembrane segment 3, transmembrane segment 4, transmembrane segment 5, and part of transmembrane segment 6; exon 3 of the Zm.br2 gene encodes a third portion of the first transmembrane domain (TMD1) of the Zm.Br2 protein including the remaining part of transmembrane segment 6 and a first portion of the first nucleotide binding domain (NBD1) of the Zm.Br2 protein including the Walker A motif; exon 4 of the Zm.br2 gene encodes a second portion of the first nucleotide binding domain (NBD1) of the Zm.Br2 protein including the Q-Loop motif; and exon 5 of the Zm.br2 gene encodes the remainder of the Zm.Br2 protein including a third portion of the first nucleotide binding domain (NBD1) of the Zm.Br2 protein including the ABC Transport, Walker B, D-Loop, and H-Loop motifs, the second transmembrane domain (TMD2), and the second nucleotide binding domain (NBD2).

According to embodiments of the present disclosure, a dominant or semi-dominant mutant allele of an endogenous Zm.br2 gene in a corn or maize plant or plant cell comprising a premature stop codon or deletion can be made by targeted mutagenesis or editing at or near at least one target site within a region of the endogenous Zm.br2 gene downstream of the polynucleotide sequence encoding the first transmembrane segment (TM Segment 1) of the first transmembrane domain (TMD1) but upstream of the first nucleotide binding domain (NBD1) or the Walker A motif of the first nucleotide binding domain (NBD1) corresponding to nucleotide positions 1477-2717 or 1477-2609 of SEQ ID NO: 1, nucleotide positions 477-1486, 477-1378, 477-604, 605-1241, 1242-1378, or 1242-1486 of SEQ ID NO: 2, and amino acid positions 160-496 or 160-460 of SEQ ID NO: 3, which may be within exon 1, intron 1, exon 2, intron 2, and/or exon 3 of the Zm.br2 gene. According to some embodiments, a dominant or semi-dominant mutant allele of an endogenous Zm.br2 gene in a corn or maize plant or plant cell comprising a premature stop codon or deletion can be made by targeted mutagenesis or editing at or near at least one target site within a region of the endogenous Zm.br2 gene downstream of the polynucleotide sequence encoding the second transmembrane segment (TM Segment 2) of the first transmembrane domain (TMD1) but upstream of the first nucleotide binding domain (NBD1) or the Walker A motif of the first nucleotide binding domain (NBD1) corresponding to nucleotide positions 1591-2717 or 1591-2609 of SEQ ID NO: 1, nucleotide positions 591-1486, 591-1378, 591-604, 605-1241, 1242-1378, or 1242-1486 of SEQ ID NO: 2, and amino acid positions 197-496 or 197-460 of SEQ ID NO: 3, which may be within exon 1, intron 1, exon 2, intron 2, and/or exon 3 of the Zm.br2 gene. According to some embodiments, a dominant or semi-dominant mutant allele of an endogenous Zm.br2 gene in a corn or maize plant or plant cell comprising a premature stop codon or deletion can be made by targeted mutagenesis or editing at or near at least one target site within a region of the endogenous Zm.br2 gene downstream of the polynucleotide sequence encoding the third transmembrane segment (TM Segment 3) of the first transmembrane domain (TMD1) but upstream of the first nucleotide binding domain (NBD1) or the Walker A motif of the first nucleotide binding domain (NBD1) corresponding to nucleotide positions 1992-2717 or 1992-2609 of SEQ ID NO: 1, nucleotide positions 849-1486, 849-1378, 849-1241, 1242-1378, or 1242-1486 of SEQ ID NO: 2, and amino acid positions 283-496 or 283-460 of SEQ ID NO: 3, which may be within exon 2, intron 2, and/or exon 3 of the Zm.br2 gene. According to some embodiments, a dominant or semi-dominant mutant allele of an endogenous Zm.br2 gene in a corn or maize plant or plant cell comprising a premature stop codon or deletion can be made by targeted mutagenesis or editing at or near at least one target site within a region of the endogenous Zm.br2 gene downstream of the polynucleotide sequence encoding the fourth transmembrane segment (TM Segment 4) of the first transmembrane domain (TMD1) but upstream of the first nucleotide binding domain (NBD1) or the Walker A motif of the first nucleotide binding domain (NBD1) corresponding to nucleotide positions 2064-2717 or 2064-2609 of SEQ ID NO: 1, nucleotide positions 921-1486, 921-1378, 921-1241, 1242-1378, or 1242-1486 of SEQ ID NO: 2, and amino acid positions 307-496 or 307-460 of SEQ ID NO: 3, which may be within exon 2, intron 2, and/or exon 3 of the Zm.br2 gene. According to some embodiments, a dominant or semi-dominant mutant allele of an endogenous Zm.br2 gene in a corn or maize plant or plant cell comprising a premature stop codon or deletion can be made by targeted mutagenesis or editing at or near at least one target site within a region of the endogenous Zm.br2 gene downstream of the polynucleotide sequence encoding the fifth transmembrane segment (TM Segment 5) of the first transmembrane domain (TMD1) but upstream of the first nucleotide binding domain (NBD1) or the Walker A motif of the first nucleotide binding domain (NBD1) corresponding to nucleotide positions 2319-2717 or 2319-2609 of SEQ ID NO: 1, nucleotide positions 1176-1486, 1176-1378, 1176-1241, 1242-1378, or 1242-1486 of SEQ ID NO: 2, and amino acid positions 392-496 or 392-460 of SEQ ID NO: 3, which may be within exon 2, intron 2, and/or exon 3 of the Zm.br2 gene. According to some embodiments, a dominant or semi-dominant mutant allele of an endogenous Zm.br2 gene in a corn or maize plant or plant cell comprising a premature stop codon or deletion can be made by targeted mutagenesis or editing at or near at least one target site within a region of the endogenous Zm.br2 gene downstream of the polynucleotide sequence encoding the sixth transmembrane segment (TM Segment 6) of the first transmembrane domain (TMD1) but upstream of the first nucleotide binding domain (NBD1) or the Walker A motif of the first nucleotide binding domain (NBD1) corresponding to nucleotide positions 2495-2717 or 2495-2609 of SEQ ID NO: 1, nucleotide positions 1263-1486 or 1263-1378 of SEQ ID NO: 2, and amino acid positions 421-496 or 421-460 of SEQ ID NO: 3, which may be within exon 3 of the Zm.br2 gene.

According to some embodiments, a dominant or semi-dominant mutant allele of an endogenous Zm.br2 gene in a corn or maize plant or plant cell comprising a deletion can be made by targeted mutagenesis or editing (i.e., double stranded break or nick) (i) at or near a first target site within a region of the endogenous Zm.br2 gene downstream of the polynucleotide sequence encoding the first transmembrane segment (TM Segment 1) of the first transmembrane domain (TMD1) but upstream of the first nucleotide binding domain (NBD1) or the Walker A motif of the first nucleotide binding domain (NBD1) corresponding to nucleotide positions 1477-2717 or 1477-2609 of SEQ ID NO: 1, nucleotide positions 477-1486, 477-1378, 477-604, 605-1241, 1242-1378, or 1242-1486 of SEQ ID NO: 2, and amino acid positions 160-496 or 160-460 of SEQ ID NO: 3, which may be within exon 1, intron 1, exon 2, intron 2, and/or exon 3 of the Zm.br2 gene, and (ii) at or near a second target site within a region of the endogenous Zm.br2 gene downstream of the polynucleotide sequence encoding the first nucleotide binding domain (NBD1) or the H-Loop motif of the first nucleotide binding domain (NBD1), which may correspond to nucleotide positions 5507-8667 or 5627-8667 of SEQ ID NO: 1, nucleotide positions 1980-4140 or 2100-4140 of SEQ ID NO: 2, and amino acid positions 660-1379 or 700-1379 of SEQ ID NO: 3, and which may be within exon 5, 3'UTR and/or downstream of the Zm.br2 gene, such that a polynucleotide target region between the first and second target sites is deleted.

According to some embodiments, a dominant or semi-dominant mutant allele of an endogenous Zm.br2 gene in a corn or maize plant or plant cell comprising a deletion can be made by targeted mutagenesis or editing (i.e., double stranded break or nick) (i) at or near a first target site within a region of the endogenous Zm.br2 gene downstream of the polynucleotide sequence encoding the second transmembrane segment (TM Segment 2) of the first transmembrane domain (TMD1) but upstream of the first nucleotide binding domain (NBD1) or the Walker A motif of the first nucleotide binding domain (NBD1) corresponding to nucleotide positions 1591-2717 or 1591-2609 of SEQ ID NO: 1, nucleotide positions 591-1486, 591-1378, 591-604, 605-1241, 1242-1378, or 1242-1486 of SEQ ID NO: 2, and amino acid positions 197-496 or 197-460 of SEQ ID NO: 3, which may be within exon 1, intron 1, exon 2, intron 2, and/or exon 3 of the Zm.br2 gene, and (ii) at or near a second target site within a region of the endogenous Zm.br2 gene downstream of the polynucleotide sequence encoding the H-Loop motif of the first nucleotide binding domain (NBD1), which may correspond to nucleotide positions 5507-8667 or 5627-8667 of SEQ ID NO: 1, nucleotide positions 1980-4140 or 2100-4140 of SEQ ID NO: 2, and amino acid positions 660-1379 or 700-1379 of SEQ ID NO: 3, and which may be within exon 5, 3'UTR and/or downstream of the Zm.br2 gene, such that a polynucleotide target region between the first and second target sites is deleted.

According to some embodiments, a dominant or semi-dominant mutant allele of an endogenous Zm.br2 gene in a corn or maize plant or plant cell comprising a deletion can be made by targeted mutagenesis or editing (i.e., double stranded break or nick) (i) at or near at least one target site within a region of the endogenous Zm.br2 gene downstream of the polynucleotide sequence encoding the third transmembrane segment (TM Segment 3) of the first transmembrane domain (TMD1) but upstream of the first nucleotide binding domain (NBD1) or the Walker A motif of the first nucleotide binding domain (NBD1) corresponding to nucleotide positions 1992-2717 or 1992-2609 of SEQ ID NO: 1, nucleotide positions 849-1486, 849-1378, 849-1241, 1242-1378, or 1242-1486 of SEQ ID NO: 2, and amino acid positions 283-496 or 283-460 of SEQ ID NO: 3, which may be within exon 2, intron 2, and/or exon 3 of the Zm.br2 gene, and (ii) at or near a second target site within a region of the endogenous Zm.br2 gene downstream of the polynucleotide sequence encoding the H-Loop motif of the first nucleotide binding domain (NBD1), which may correspond to nucleotide positions 5507-8667 or 5627-8667 of SEQ ID NO: 1, nucleotide positions 1980-4140 or 2100-4140 of SEQ ID NO: 2, and amino acid positions 660-1379 or 700-1379 of SEQ ID NO: 3, and which may be within exon 5, 3'UTR and/or downstream of the Zm.br2 gene, such that a polynucleotide target region between the first and second target sites is deleted.

According to some embodiments, a dominant or semi-dominant mutant allele of an endogenous Zm.br2 gene in a corn or maize plant or plant cell comprising a deletion can be made by targeted mutagenesis or editing (i.e., double stranded break or nick) (i) at or near at least one target site within a region of the endogenous Zm.br2 gene downstream of the polynucleotide sequence encoding the fourth transmembrane segment (TM Segment 4) of the first transmembrane domain (TMD1) but upstream of the first nucleotide binding domain (NBD1) or the Walker A motif of the first nucleotide binding domain (NBD1) corresponding to nucleotide positions 2064-2717 or 2064-2609 of SEQ ID NO: 1, nucleotide positions 921-1486, 921-1378, 921-1241, 1242-1378, or 1242-1486 of SEQ ID NO: 2, and amino acid positions 307-496 or 307-460 of SEQ ID NO: 3, which may be within exon 2, intron 2, and/or exon 3 of the Zm.br2 gene, and (ii) at or near a second target site within a region of the endogenous Zm.br2 gene downstream of the polynucleotide sequence encoding the H-Loop motif of the first nucleotide binding domain (NBD1), which may correspond to nucleotide positions 5507-8667 or 5627-8667 of SEQ ID NO: 1, nucleotide positions 1980-4140 or 2100-4140 of SEQ ID NO: 2, and amino acid positions 660-1379 or 700-1379 of SEQ ID NO: 3, and which may be within exon 5, 3'UTR and/or downstream of the Zm.br2 gene, such that a polynucleotide target region between the first and second target sites is deleted.

According to some embodiments, a dominant or semi-dominant mutant allele of an endogenous Zm.br2 gene in a corn or maize plant or plant cell comprising a deletion can be made by targeted mutagenesis or editing (i.e., double stranded break or nick) (i) at or near at least one target site within a region of the endogenous Zm.br2 gene downstream of the polynucleotide sequence encoding the fifth transmembrane segment (TM Segment 5) of the first transmembrane domain (TMD1) but upstream of the first nucleotide binding domain (NBD1) or the Walker A motif of the first nucleotide binding domain (NBD1) corresponding to nucleotide positions 2319-2717 or 2319-2609 of SEQ ID NO: 1, nucleotide positions 1176-1486, 1176-1378, 1176-1241, 1242-1378, or 1242-1486 of SEQ ID NO: 2, and amino acid positions 392-496 or 392-460 of SEQ ID NO: 3, which may be within exon 2, intron 2, and/or exon 3 of the Zm.br2 gene, and (ii) at or near a second target site within a region of the endogenous Zm.br2 gene downstream of the polynucleotide sequence encoding the H-Loop motif of the first nucleotide binding domain (NBD1), which may correspond to nucleotide positions 5507-8667 or 5627-8667 of SEQ ID NO: 1, nucleotide positions 1980-4140 or 2100-4140 of SEQ ID NO: 2, and amino acid positions 660-1379 or 700-1379 of SEQ ID NO: 3, and which may be within exon 5, 3'UTR and/or downstream of the Zm.br2 gene, such that a polynucleotide target region between the first and second target sites is deleted.

According to some embodiments, a dominant or semi-dominant mutant allele of an endogenous Zm.br2 gene in a corn or maize plant or plant cell comprising a deletion can be made by targeted mutagenesis or editing (i.e., double stranded break or nick) (i) at or near at least one target site within a region of the endogenous Zm.br2 gene downstream of the polynucleotide sequence encoding the sixth transmembrane segment (TM Segment 6) of the first transmembrane domain (TMD1) but upstream of the first nucleotide binding domain (NBD1) or the Walker A motif of the first nucleotide binding domain (NBD1) corresponding to nucleotide positions 2495-2717 or 2495-2609 of SEQ ID NO: 1, nucleotide positions 1263-1486 or 1263-1378 of SEQ ID NO: 2, and amino acid positions 421-496 or 421-460 of SEQ ID NO: 3, which may be within exon 3 of the Zm.br2 gene, and (ii) at or near a second target site within a region of the endogenous Zm.br2 gene downstream of the polynucleotide sequence encoding the H-Loop motif of the first nucleotide binding domain (NBD1), which may correspond to nucleotide positions 5507-8667 or 5627-8667 of SEQ ID NO: 1, nucleotide positions 1980-4140 or 2100-4140 of SEQ ID NO: 2, and amino acid positions 660-1379 or 700-1379 of SEQ ID NO: 3, and which may be within exon 5, 3'UTR and/or downstream of the Zm.br2 gene, such that a polynucleotide target region between the first and second target sites is deleted.

According to some embodiments, a dominant or semi-dominant mutant allele of an endogenous Zm.br2 gene in a corn or maize plant or plant cell comprising a premature stop codon can be made by targeted mutagenesis or editing (i.e., double stranded break or nick) (i) at or near a first target site within a region of the endogenous Zm.br2 gene downstream of the polynucleotide sequence encoding the first transmembrane segment (TM Segment 1) of the first transmembrane domain (TMD1) but upstream of the first nucleotide binding domain (NBD1) or the Walker A motif of the first nucleotide binding domain (NBD1) corresponding to nucleotide positions 1477-2717 or 1477-2609 of SEQ ID NO: 1, nucleotide positions 477-1486, 477-1378, 477-604, 605-1241, 1242-1378, or 1242-1486 of SEQ ID NO: 2, and amino acid positions 160-496 or 160-460 of SEQ ID NO: 3, which may be within exon 1, intron 1, exon 2, intron 2, and/or exon 3 of the Zm.br2 gene, and (ii) at or near a second target site downstream of the first target site and within a region of the endogenous Zm.br2 gene downstream of the polynucleotide sequence encoding the first transmembrane segment (TM Segment 1) of the first transmembrane domain (TMD1) but upstream of the first nucleotide binding domain (NBD1) or the Walker A motif of the first nucleotide binding domain (NBD1) corresponding to nucleotide positions 1477-2717 or 1477-2609 of SEQ ID NO: 1, nucleotide positions 477-1486, 477-1378, 477-604, 605-1241, 1242-1378, or 1242-1486 of SEQ ID NO: 2, and amino acid positions 160-496 or 160-460 of SEQ ID NO: 3, which may be within exon 1, intron 1, exon 2, intron 2, and/or exon 3 of the Zm.br2 gene.

According to some embodiments, a dominant or semi-dominant mutant allele of an endogenous Zm.br2 gene in a corn or maize plant or plant cell comprising a premature stop codon can be made by targeted mutagenesis or editing (i.e., double stranded break or nick) (i) at or near a first target site within a region of the endogenous Zm.br2 gene downstream of the polynucleotide sequence encoding the second transmembrane segment (TM Segment 2) of the first transmembrane domain (TMD1) but upstream of the first nucleotide binding domain (NBD1) or the Walker A motif of the first nucleotide binding domain (NBD1) corresponding to nucleotide positions 1591-2717 or 1591-2609 of SEQ ID NO: 1, nucleotide positions 591-1486, 591-1378, 591-604, 605-1241, 1242-1378, or 1242-1486 of SEQ ID NO: 2, and amino acid positions 197-496 or 197-460 of SEQ ID NO: 3, which may be within exon 1, intron 1, exon 2, intron 2, and/or exon 3 of the Zm.br2 gene, and (ii) at or near a second target site downstream of the first target site and within a region of the endogenous Zm.br2 gene downstream of the polynucleotide sequence encoding the second transmembrane segment (TM Segment 2) of the first transmembrane domain (TMD1) but upstream of the first nucleotide binding domain (NBD1) or the Walker A motif of the first nucleotide binding domain (NBD1) corresponding to nucleotide positions 1591-2717 or 1591-2609 of SEQ ID NO: 1, nucleotide positions 591-1486, 591-1378, 591-604, 605-1241, 1242-1378, or 1242-1486 of SEQ ID NO: 2, and amino acid positions 197-496 or 197-460 of SEQ ID NO: 3, which may be within exon 1, intron 1, exon 2, intron 2, and/or exon 3 of the Zm.br2 gene.

According to some embodiments, a dominant or semi-dominant mutant allele of an endogenous Zm.br2 gene in a corn or maize plant or plant cell comprising a premature stop codon can be made by targeted mutagenesis or editing (i.e., double stranded break or nick) (i) at or near at least one target site within a region of the endogenous Zm.br2 gene downstream of the polynucleotide sequence encoding the third transmembrane segment (TM Segment 3) of the first transmembrane domain (TMD1) but upstream of the first nucleotide binding domain (NBD1) or the Walker A motif of the first nucleotide binding domain (NBD1) corresponding to nucleotide positions 1992-2717 or 1992-2609 of SEQ ID NO: 1, nucleotide positions 849-1486, 849-1378, 849-1241, 1242-1378, or 1242-1486 of SEQ ID NO: 2, and amino acid positions 283-496 or 283-460 of SEQ ID NO: 3, which may be within exon 2, intron 2, and/or exon 3 of the Zm.br2 gene, and (ii) at or near a second target site downstream of the first target site within a region of the endogenous Zm.br2 gene downstream of the polynucleotide sequence encoding the third transmembrane segment (TM Segment 3) of the first transmembrane domain (TMD1) but upstream of the first nucleotide binding domain (NBD1) or the Walker A motif of the first nucleotide binding domain (NBD1) corresponding to nucleotide positions 1992-2717 or 1992-2609 of SEQ ID NO: 1, nucleotide positions 849-1486, 849-1378, 849-1241, 1242-1378, or 1242-1486 of SEQ ID NO: 2, and amino acid positions 283-496 or 283-460 of SEQ ID NO: 3, which may be within exon 2, intron 2, and/or exon 3 of the Zm.br2 gene.

According to some embodiments, a dominant or semi-dominant mutant allele of an endogenous Zm.br2 gene in a corn or maize plant or plant cell comprising a premature stop codon can be made by targeted mutagenesis or editing (i.e., double stranded break or nick) (i) at or near at least one target site within a region of the endogenous Zm.br2 gene downstream of the polynucleotide sequence encoding the fourth transmembrane segment (TM Segment 4) of the first transmembrane domain (TMD1) but upstream of the first nucleotide binding domain (NBD1) or the Walker A motif of the first nucleotide binding domain (NBD1) corresponding to nucleotide positions 2064-2717 or 2064-2609 of SEQ ID NO: 1, nucleotide positions 921-1486, 921-1378, 921-1241, 1242-1378, or 1242-1486 of SEQ ID NO: 2, and amino acid positions 307-496 or 307-460 of SEQ ID NO: 3, which may be within exon 2, intron 2, and/or exon 3 of the Zm.br2 gene, and (ii) at or near a second target site downstream of the first target site and within a region of the endogenous Zm.br2 gene downstream of the polynucleotide sequence encoding the fourth transmembrane segment (TM Segment 4) of the first transmembrane domain (TMD1) but upstream of the first nucleotide binding domain (NBD1) or the Walker A motif of the first nucleotide binding domain (NBD1) corresponding to nucleotide positions 2064-2717 or 2064-2609 of SEQ ID NO: 1, nucleotide positions 921-1486, 921-1378, 921-1241, 1242-1378, or 1242-1486 of SEQ ID NO: 2, and amino acid positions 307-496 or 307-460 of SEQ ID NO: 3, which may be within exon 2, intron 2, and/or exon 3 of the Zm.br2 gene.

According to some embodiments, a dominant or semi-dominant mutant allele of an endogenous Zm.br2 gene in a corn or maize plant or plant cell comprising a premature stop codon can be made by targeted mutagenesis or editing (i.e., double stranded break or nick) (i) at or near at least one target site within a region of the endogenous Zm.br2 gene downstream of the polynucleotide sequence encoding the fifth transmembrane segment (TM Segment 5) of the first transmembrane domain (TMD1) but upstream of the first nucleotide binding domain (NBD1) or the Walker A motif of the first nucleotide binding domain (NBD1) corresponding to nucleotide positions 2319-2717 or 2319-2609 of SEQ ID NO: 1, nucleotide positions 1176-1486, 1176-1378, 1176-1241, 1242-1378, or 1242-1486 of SEQ ID NO: 2, and amino acid positions 392-496 or 392-460 of SEQ ID NO: 3, which may be within exon 2, intron 2, and/or exon 3 of the Zm.br2 gene, and (ii) at or near a second target site downstream of the first target site and within a region of the endogenous Zm.br2 gene downstream of the polynucleotide sequence encoding the fifth transmembrane segment (TM Segment 5) of the first transmembrane domain (TMD1) but upstream of the first nucleotide binding domain (NBD1) or the Walker A motif of the first nucleotide binding domain (NBD1) corresponding to nucleotide positions 2319-2717 or 2319-2609 of SEQ ID NO: 1, nucleotide positions 1176-1486, 1176-1378, 1176-1241, 1242-1378, or 1242-1486 of SEQ ID NO: 2, and amino acid positions 392-496 or 392-460 of SEQ ID NO: 3, which may be within exon 2, intron 2, and/or exon 3 of the Zm.br2 gene.

According to some embodiments, a dominant or semi-dominant mutant allele of an endogenous Zm.br2 gene in a corn or maize plant or plant cell comprising a premature stop codon can be made by targeted mutagenesis or editing (i.e., double stranded break or nick) (i) at or near at least one target site within a region of the endogenous Zm.br2 gene downstream of the polynucleotide sequence encoding the sixth transmembrane segment (TM Segment 6) of the first transmembrane domain (TMD1) but upstream of the first nucleotide binding domain (NBD1) or the Walker A motif of the first nucleotide binding domain (NBD1) corresponding to nucleotide positions 2495-2717 or 2495-2609 of SEQ ID NO: 1, nucleotide positions 1263-1486 or 1263-1378 of SEQ ID NO: 2, and amino acid positions 421-496 or 421-460 of SEQ ID NO: 3, which may be within exon 3 of the Zm.br2 gene, and (ii) at or near a second target site downstream of the first target site and within a region of the endogenous Zm.br2 gene downstream of the polynucleotide sequence encoding the sixth transmembrane segment (TM Segment 6) of the first transmembrane domain (TMD1) but upstream of the first nucleotide binding domain (NBD1) or the Walker A motif of the first nucleotide binding domain (NBD1) corresponding to nucleotide positions 2495-2717 or 2495-2609 of SEQ ID NO: 1, nucleotide positions 1263-1486 or 1263-1378 of SEQ ID NO: 2, and amino acid positions 421-496 or 421-460 of SEQ ID NO: 3, which may be within exon 3 of the Zm.br2 gene.

According to embodiments of the present disclosure, a dominant or semi-dominant mutant allele of an endogenous Zm.br2 gene in a corn or maize plant or plant cell comprising a premature stop codon or deletion may comprise a polynucleotide coding sequence that is at least 80%, at least 85%, at least 90%, at least 95% or 100% identical to nucleotides 1-2718 of SEQ ID NO: 1 and/or nucleotides 1-1486, 1-604, 605-1241, or 1242-1486 of SEQ ID NO: 2, and/or encodes a truncated Zm.Br2 protein that is at least 80%, at least 85%, at least 90%, at least 95% or 100% identical to amino acids 1-496 of SEQ ID NO: 3. According to embodiments of the present disclosure, a dominant or semi-dominant mutant allele of an endogenous Zm.br2 gene in a corn or maize plant or plant cell comprising a premature stop codon or deletion may comprise a polynucleotide coding sequence that is at least 80%, at least 85%, at least 90%, at least 95% or 100% identical to nucleotides 1-2495 of SEQ ID NO: 1 and/or nucleotides 1-1263, 1-604, 605-1241, or 1242-1263 of SEQ ID NO: 2, and/or encodes a truncated Zm.Br2 protein that is at least 80%, at least 85%, at least 90%, at least 95% or 100% identical to amino acids 1-421 of SEQ ID NO: 3. According to embodiments of the present disclosure, a dominant or semi-dominant mutant allele of an endogenous Zm.br2 gene in a corn or maize plant or plant cell comprising a premature stop codon or deletion may comprise a polynucleotide coding sequence that is at least 80%, at least 85%, at least 90%, at least 95% or 100% identical to nucleotides 1-2319 of SEQ ID NO: 1 and/or nucleotides 1-1176, 1-604, 605-1176 of SEQ ID NO: 2, and/or encodes a truncated Zm.Br2 protein that is at least 80%, at least 85%, at least 90%, at least 95% or 100% identical to amino acids 1-392 of SEQ ID NO: 3. According to embodiments of the present disclosure, a dominant or semi-dominant mutant allele of an endogenous Zm.br2 gene in a corn or maize plant or plant cell comprising a premature stop codon or deletion may comprise a polynucleotide coding sequence that is at least 80%, at least 85%, at least 90%, at least 95% or 100% identical to nucleotides 1-2064 of SEQ ID NO: 1 and/or nucleotides 1-921, 1-604, 605-921 of SEQ ID NO: 2, and/or encodes a truncated Zm.Br2 protein that is at least 80%, at least 85%, at least 90%, at least 95% or 100% identical to amino acids 1-307 of SEQ ID NO: 3. According to embodiments of the present disclosure, a dominant or semi-dominant mutant allele of an endogenous Zm.br2 gene in a corn or maize plant or plant cell comprising a premature stop codon or deletion may comprise a polynucleotide coding sequence that is at least 80%, at least 85%, at least 90%, at least 95% or 100% identical to nucleotides 1-1989 of SEQ ID NO: 1 and/or nucleotides 1-849, 1-604, 605-849 of SEQ ID NO: 2, and/or encodes a truncated Zm.Br2 protein that is at least 80%, at least 85%, at least 90%, at least 95% or 100% identical to amino acids 1-283 of SEQ ID NO: 3. According to embodiments of the present disclosure, a dominant or semi-dominant mutant allele of an endogenous Zm.br2 gene in a corn or maize plant or plant cell comprising a premature stop codon or deletion may comprise a polynucleotide coding sequence that is at least 80%, at least 85%, at least 90%, at least 95% or 100% identical to nucleotides 1-1591 of SEQ ID NO: 1 and/or nucleotides 1-591 of SEQ ID NO: 2, and/or encodes a truncated Zm.Br2 protein that is at least 80%, at least 85%, at least 90%, at least 95% or 100% identical to amino acids 1-197 of SEQ ID NO: 3. According to embodiments of the present disclosure, a dominant or semi-dominant mutant allele of an endogenous Zm.br2 gene in a corn or maize plant or plant cell comprising a premature stop codon or deletion may comprise a polynucleotide coding sequence that is at least 80%, at least 85%, at least 90%, at least 95% or 100% identical to nucleotides 1-1477 of SEQ ID NO: 1 and/or nucleotides 1-477 of SEQ ID NO: 2, and/or encodes a truncated Zm.Br2 protein that is at least 80%, at least 85%, at least 90%, at least 95% or 100% identical to amino acids 1-159 of SEQ ID NO: 3.

In an aspect, a premature stop codon or deletion is introduced to an endogenous br2 locus via a targeted editing technique. In an aspect, this disclosure provides a method for producing a mutant allele of an endogenous Brachytic2 (br2) locus, the method comprising: (a) generating at least a double-stranded break (DSB) in the endogenous br2 locus in at least one corn cell using a targeted editing technique; and (b) identifying at least one corn cell, corn seed or corn plant from the at least one corn cell in step (a) comprising a premature stop codon or deletion in the coding sequence of the endogenous br2 locus. In an aspect, the method further comprises regenerating at least one corn plant from the at least one corn cell identified in step (b).

Creation of dominant or semi-dominant alleles that work in a heterozygous state can speed up effective trait development, deployment, and launch of gene editing-derive products in hybrid crops such as corn or maize. Dominant or semi-dominant alleles have the potential advantage of providing a positive or beneficial plant trait in a heterozygous state—i.e., when present in a single copy. As a result, the dominant mutant allele can be introduced through crossing into a progeny plant from a single parent without having to introduce the mutant allele from both parent plants as required with a recessive trait or allele. The present disclosure provides methods and compositions to selectively mutate or edit a genome of a corn plant, or more particularly an endogenous Zm.br2 gene, to create a dominant or semi-dominant mutant allele that produces a beneficial trait, such as shorter plant height or stature, in a corn or maize plant.

In an aspect, this disclosure provides a modified corn plant or plant part, and a method for making or producing a modified corn plant or plant part, where the modified corn plant or plant part has a dominant or semi-dominant mutant allele at the endogenous br2 locus or gene that causes the modified corn plant to have a beneficial phenotype or trait, such as shorter plant height or stature, relative to a wild-type or control plant. Such dominant or semi-dominant mutant allele of the endogenous br2 locus or gene can modify, alter, reduce and/or mask a trait associated with a wild-type allele through one or more mechanisms as described herein.

In an aspect, this disclosure provides a modified corn plant or plant part, and a method for producing a modified corn plant or plant part, where the modified corn plant or plant part comprises a mutant or edited allele of an endogenous br2 gene or locus comprising a deletion of all or part of the br2 gene or locus and/or a premature stop codon in the coding sequence of the br2 gene or locus.

Further provided herein are methods of generating dominant or semi-dominant mutant alleles of a Zm.br2 gene using targeted editing techniques. Also provided herein are plant parts, tissues and cells generated by such methods and compositions used in such methods. The instant description further provides modified plants regenerated from cells subjected to the methods provided herein. In one aspect, a dominant or semi-dominant allele of a Zm.br2 gene provided herein not only encodes a truncated Br2 protein comprising at least one transmembrane segment and lacking any nucleotide binding motif, but also may further comprise one or more polynucleotide deletions, inversions, substitutions, and/or insertions.

In an aspect, a br2 mutant allele comprises a premature stop codon within a region selected from the group consisting of the first exon, second exon, and/or third exon of the endogenous br2 gene or locus introduced by a mutagenesis or targeted editing technique. In an aspect, this disclosure provides a modified corn plant, or plant part thereof, or a modified corn plant part, plant cell or tissue, comprising a premature stop codon within an endogenous br2 locus as compared to a control corn plant or plant part thereof.

In an aspect, a br2 mutant allele comprises a deletion of at least one portion of the endogenous br2 gene or locus. In an aspect, this disclosure provides a modified corn plant, or plant part thereof, or a modified corn plant part, plant cell or tissue, comprising a deletion within an endogenous br2 locus as compared to a control corn plant, plant part, etc. In an aspect, this disclosure provides a modified corn plant, or plant part thereof, or a modified corn plant part, plant cell or tissue, comprising a deletion of or within at least one exon of an endogenous br2 gene or locus, such as a first exon, a second exon, and/or a third exon, as compared to a control corn plant, plant part, etc. In an aspect, this disclosure provides a modified corn plant, or plant part thereof, or a modified corn plant part, plant cell or tissue, comprising a deletion of at least one nucleotide from at least one exon of an endogenous br2 gene or locus, such as a first exon, a second exon, and/or a third exon, as compared to a control corn plant, plant part, etc.

In an aspect, a deletion within the genomic sequence of an endogenous br2 gene or locus (SEQ ID NO: 1) may comprise between 450 nucleotides and 7500 nucleotides, between 450 nucleotides and 7000 nucleotides, between 450 nucleotides and 6000 nucleotides, between 450 nucleotides and 5000 nucleotides, between 450 nucleotides and 4000 nucleotides, between 450 nucleotides and 3000 nucleotides, between 450 nucleotides and 2000 nucleotides, between 450 nucleotides and 1000 nucleotides, between 500 nucleotides and 7500 nucleotides, between 500 nucleotides and 7000 nucleotides, between 500 nucleotides and 6000 nucleotides, between 500 nucleotides and 5000 nucleotides, between 500 nucleotides and 4000 nucleotides, between 500 nucleotides and 3000 nucleotides, between 500 nucleotides and 2500 nucleotides, between 500 nucleotides and 2000 nucleotides, between 500 nucleotides and 1000 nucleotides, between 750 nucleotides and 7500 nucleotides, between 750 nucleotides and 7000 nucleotides, between 750 nucleotides and 6000 nucleotides, between 750 nucleotide and 5000 nucleotides, between 750 nucleotides and 4000 nucleotides, between 750 nucleotides and 3000 nucleotides, between 750 nucleotides and 2500 nucleotides, between 750 nucleotides and 2000 nucleotides, between 750 nucleotides and 1000 nucleotides, between 1000 nucleotides and 7500 nucleotides, between 1000 nucleotides and 7000 nucleotides, between 1000 nucleotides and 6000 nucleotides, between 1000 nucleotides and 5000 nucleotides, between 1000 nucleotides and 4000 nucleotides, between 1000 nucleotides and 3000 nucleotides, between 1000 nucleotides and 2500 nucleotides, or between 1000 nucleotides and 2000 nucleotides, or between 1000 nucleotides and 1500 nucleotides. In an aspect, a deletion within the genomic sequence an endogenous br2 gene or locus (SEQ ID NO: 1) comprises at least 400 nucleotides, at least 450 nucleotides, at least 500 nucleotides, at least 600 nucleotides, at least 700 nucleotides, at least 800 nucleotides, at least 900 nucleotides, at least 1000 nucleotides, at least 1250 nucleotides, at least 1500 nucleotides, at least 1750 nucleotides, at least 2000 nucleotides, at least 3000 nucleotides, at least 4000 nucleotides, at least 5000 nucleotides, at least 6000 nucleotides, or at least 7000 nucleotides.

In an aspect, a deletion comprises deletion of all or at least part of the first exon of an endogenous br2 gene or locus. In an aspect, a deletion comprises deletion of all or at least part of the first intron of an endogenous br2 gene or locus. In an aspect, a deletion comprises deletion of all or at least part of the second exon of an endogenous br2 gene or locus. In an aspect, a deletion comprises deletion of all or at least part of the second intron of an endogenous br2 gene or locus. In an aspect, a deletion comprises deletion of all or at least part of the third exon of an endogenous br2 gene or locus. In an aspect, a deletion comprises deletion of all or at least part of the third intron of an endogenous br2 gene or locus. In an aspect, a deletion comprises deletion of all or at least part of the fourth exon of an endogenous br2 gene or locus. In an aspect, a deletion comprises deletion of all or at least part of the fourth intron of an endogenous br2 gene or locus. In an aspect, a deletion comprises deletion of all or at least part of the fifth exon of an endogenous br2 gene or locus.

In an aspect, a deletion comprises a deletion of all or at least part of at least two exons, at least three exons, at least four exons, at least one intron, at least two introns, or at least three introns of an endogenous br2 gene or locus, or any combination thereof.

In an aspect, a deletion comprises deletion of at least one nucleotide from a first exon and at least one nucleotide from a second exon of an endogenous br2 locus. In an aspect, a deletion comprises deletion of at least one nucleotide from a first exon, at least one nucleotide from a second exon, and at least one nucleotide from a third exon of an endogenous br2 locus. In an aspect, a deletion comprises deletion of at least one nucleotide from a first exon, at least one nucleotide from a second exon, at least one nucleotide from a third exon, and at least one nucleotide from a fourth exon of an endogenous br2 locus. In an aspect, a deletion comprises deletion of at least one nucleotide from a first exon, at least one nucleotide from a second exon, at least one nucleotide from a third exon, at least one nucleotide from a fourth exon, and at least one nucleotide from a fifth exon of an endogenous br2 locus.

In an aspect, this disclosure provides a method for producing a mutant allele of an endogenous Brachytic2 (br2) locus, the method comprising (a) generating at least a first double-stranded break (DSB) and/or a second DSB in the endogenous br2 locus in at least one corn cell using a targeted editing technique; and (b) identifying at least one corn cell from step (a) comprising a deletion of the endogenous br2 locus at or near the first DSB or the second DSB or between the first DSB and the second DSB.

In an aspect, a modified corn plant, or plant part thereof, or a modified corn plant part, plant cell or tissue, is homozygous for a mutant allele at the endogenous br2 locus. In another aspect, a modified corn plant, or plant part thereof, or a modified corn plant part, plant cell or plant tissue, is heterozygous for a mutant allele at the endogenous br2 locus. In another aspect, a modified corn plant, or plant part thereof, or a modified corn plant part, plant cell or plant tissue, is homozygous and heteroallelic or biallelic at the endogenous br2 locus. Such mutant allele(s) may comprise a deletion and/or a premature stop codon as provided herein. In an aspect, a modified corn plant, or plant part thereof, or a modified corn plant part, plant cell or plant tissue, homozygous for a mutant allele of an endogenous br2 gene or locus, is biallelic or heteroallelic for a first mutant allele and a second mutant allele, each within the endogenous br2 gene or locus.

In an aspect, the present disclosure provides a method for producing a mutant allele of the endogenous br2 gene or locus, the method comprising: (a) generating a first double-stranded break (DSB) or nick in the endogenous br2 gene or locus in a corn or maize cell using a targeted editing technique; and (b) producing a deletion and/or premature stop codon in the coding region of the endogenous br2 gene or locus in the corn or maize cell as described herein. In another aspect, a method further comprises regenerating or developing a modified corn plant from the corn cell.

In an aspect, a targeted editing technique used here comprises the use of at least one site-specific nuclease. In an aspect, a site-specific nuclease is selected from the group consisting of a zinc-finger nuclease, a meganuclease, an RNA-guided nuclease, a TALEN, a recombinase, a transposase, and any combination thereof. In another aspect, a site-specific nuclease is a RNA-guided nuclease selected from the group consisting of a Cas9 nuclease or a variant thereof, and a Cpf1 nuclease or a variant thereof.

According to further embodiments, methods are provided for transforming a plant cell, tissue or explant with a recombinant DNA molecule or construct encoding one or more molecules required for targeted genome editing (e.g., guide RNAs or site-directed nucleases). Numerous methods for transforming chromosomes or plastids in a plant cell with a recombinant DNA molecule or construct are known in the art, which may be used according to method embodiments of the present invention to produce a transgenic plant cell and plant. Any suitable method or technique for transformation of a plant cell known in the art may be used according to present methods. Effective methods for transformation of plants include bacterially mediated transformation, such as *Agrobacterium*-mediated or *Rhizobium*-mediated transformation, and microprojectile or particle bombardment-mediated transformation. A variety of methods are known in the art for transforming explants with a transformation vector via bacterially mediated transformation or microprojectile or particle bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art.

Methods of transforming plant cells and explants are well known by persons of ordinary skill in the art. Methods for transforming plant cells by microprojectile bombardment with particles coated with recombinant DNA are provided, for example, in U.S. Pat. Nos. 5,550,318; 5,538,880 6,160,208; 6,399,861; and 6,153,812, and *Agrobacterium*-mediated transformation is described, for example, in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any suitable method of plant transformation known or later developed in the art can be used to transform a plant cell or explant with any of the nucleic acid molecules, constructs or vectors provided herein.

Recipient cell(s) or explant or cellular targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, a callus cell, a chloroplast, a stomatal cell, a trichome cell, a root hair cell, a storage root cell, or a vascular tissue cell, a seed, embryo, meristem, cotyledon, hypocotyl, endosperm, root, shoot, stem, node, callus, cell suspension, protoplast, flower, leaf, pollen, anther, ovary, ovule, pericarp, bud, and/or vascular tissue, or any transformable portion of any of the foregoing. For plant transformation, any target cell(s), tissue(s), explant(s), etc., that may be used to receive a recombinant DNA transformation vector or molecule of the present disclosure may be collectively referred to as an "explant" for transformation. Preferably, a transformable or transformed explant cell or tissue may be further developed or regenerated into a plant. Any cell or explant from which a fertile plant can be grown or regenerated is contemplated as a useful recipient cell or explant for practice of this disclosure (i.e., as a target explant for transformation). Callus can be initiated or created from various tissue sources, including, but not limited to, embryos or parts of embryos, non-embryonic seed tissues, seedling apical meristems, microspores, and the like. Any cells that are capable of proliferating as callus may serve as recipient cells for transformation. Transformation methods and materials for making transgenic plants (e.g., various media and recipient target cells or explants and methods of transformation and subsequent regeneration of into transgenic plants) are known in the art.

Transformation or editing of a target plant material or explant may be practiced in tissue culture on nutrient media, for example a mixture of nutrients that allow cells to grow in vitro or cell culture. Modified explants, cells or tissues may be subjected to additional culturing steps, such as callus induction, selection, regeneration, etc., as known in the art. Transformation or editing may also be carried out without creation or use of a callus tissue. Transformed or edited cells, tissues or explants containing a DNA sequence insertion or edit may be grown, developed or regenerated into transgenic plants in culture, plugs, or soil according to methods known in the art. Modified plants may be further crossed to themselves or other plants to produce modified plant seeds and progeny. A modified plant may also be prepared by crossing a first plant comprising a DNA sequence or construct or an edit (e.g., an antisense sequence, deletion, or inversion) with a second plant lacking the insertion. For example, a DNA sequence, deletion, antisense sequence or inversion may be introduced into a first plant line that is amenable to transformation or editing, which may then be crossed with a second plant line to introgress the DNA sequence or edit (e.g., a deletion or frameshift) into the second plant line. Progeny of these crosses can be further back crossed into the desirable line multiple times, such as through 6 to 8 generations or back crosses, to produce a progeny plant with substantially the same genotype as the original parental line, but for the introduction of the DNA sequence or edit.

A transgenic or modified plant, plant part, cell, or explant provided herein may be of an elite variety or an elite line. An elite variety or an elite line refers to a variety that has resulted from breeding and selection for superior agronomic performance. A transgenic or edited plant, plant part, plant cell, or explant provided herein may be an inbred plant, plant part, plant cell, or explant or a hybrid plant, plant part, plant cell, or explant. As used herein, a "inbred" is a self-propagating line or variety by crossing with itself. As used herein, a "hybrid" is created by crossing two plants of different varieties, lines, inbreds, or species, such as two different corn or maize varieties, lines, or inbreds, such that the progeny comprises genetic material from each parent. Skilled artisans recognize that higher order hybrids can be generated as well. For example, a first hybrid can be made by crossing Variety A with Variety B to create an A×B hybrid, and a second hybrid can be made by crossing Variety C with Variety D to create a C×D hybrid. The first and second hybrids can be further crossed to create the higher order hybrid (A×B)×(C×D) comprising genetic information from all four parent varieties.

In an aspect, this disclosure provides a method for generating a corn plant comprising: (a) fertilizing at least one female corn plant with pollen from a male corn plant, where the female corn plant comprises a mutant allele of an endogenous Brachytic2 (br2) locus as provided herein; and (b) obtaining at least one seed produced by said fertilizing of step (a). In another aspect, the method further comprises (c) growing the at least one seed obtained in step (b) to generate at least one progeny corn plant comprising said mutant allele. In an aspect, the at least one progeny corn plant obtained in step (c) is heterozygous for the mutant allele. In an aspect, the at least one progeny corn plant obtained in step (c) is homozygous or biallelic or heteroallelic for the mutant allele(s).

In an aspect, this disclosure provides a method for generating a corn plant comprising: (a) fertilizing at least one female corn plant with pollen from a male corn plant, where the male corn plant comprises a mutant allele of an endogenous Brachytic2 (br2) locus as provided herein; and (b) obtaining at least one seed produced by said fertilizing of step (a). In another aspect, the method further comprises (c) growing the at least one seed obtained in step (b) to generate at least one progeny corn plant comprising said mutant allele. In an aspect, the at least one progeny corn plant obtained in step (c) is heterozygous for the mutant allele. In an aspect, the at least one progeny corn plant obtained in step (c) is homozygous or biallelic or heteroallelic for the mutant allele(s).

In an aspect, the female corn plant is homozygous for a mutant allele. In another aspect, the female corn plant is heterozygous for the mutant allele. In another aspect, the female corn plant is biallelic or heteroallelic for a first mutant allele and a second mutant allele. In an aspect, the male corn plant lacks the mutant allele. In an aspect, the male corn plant is heterozygous for the mutant allele. In an aspect, the male corn plant is homozygous for the mutant allele. In an aspect, the male corn plant is biallelic or heteroallelic for a first mutant allele and a second mutant allele. In an aspect, the female corn plant lacks the mutant allele. In an aspect, the at least one progeny corn plant has a shorter plant height and/or improved lodging resistance relative to a control plant lacking the mutant allele. In an aspect, the at least one progeny corn plant has a shorter plant height and/or improved lodging resistance relative to the male corn plant. In an aspect, the female corn plant is an inbred corn plant. In an aspect, the female corn plant is a hybrid corn plant. In an aspect, the male corn plant is an inbred corn plant. In an aspect, the male corn plant is a hybrid corn plant. In an aspect, the female corn plant is an elite corn plant. In an aspect, the male corn plant is an elite corn plant. In an aspect, the female corn plant is of a first inbred corn line or variety, and the male corn plant is of a different, second inbred corn line or variety. In an aspect, the female corn plant and the male corn plant are grown in a greenhouse or growth chamber. In an aspect, the female corn plant and the male corn plant are grown outdoors. In an aspect, the female corn plant has been detasseled. In an aspect, the female corn plant is a cytoplasmically male sterile corn plant.

As used herein, "detasseled" corn refers to corn where the pollen-producing flowers, or tassels, have been removed. Detasseling is typically performed before the tassel can shed pollen. Detasseling can be accomplished via machine detasseling, manual detasseling, or a combination of both machine and manual detasseling. Detasseling often removes the uppermost leaves of the corn plant along with the developing tassel. Detasseled corn plants retain their female flowers, which eventually produce kernels on the car. In an aspect, a corn plant provided herein is a detasseled corn plant. As an alternative to chemical treatment, corn plants (or female corn plants) can be made male sterile through genetic crosses and inheritance causing cytoplasmic male sterility. As used herein, the term "cytoplasmic male sterility" or "CMS" refers to a condition where a corn plant is partially or fully incapable of producing functional pollen. As known in the art, cytoplasmic male sterility is a maternally inherited trait that is commonly associated with unusual open reading frames within the mitochondrial genome which cause cytoplasmic dysfunction. In an aspect, a corn plant or female corn plant provided herein is a cytoplasmic male sterile corn plant.

A plant selectable marker transgene in a transformation vector or construct of the present disclosure may be used to assist in the selection of transformed cells or tissue due to the presence of a selection agent, such as an antibiotic or herbicide, wherein the plant selectable marker transgene provides tolerance or resistance to the selection agent. Thus, the selection agent may bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes may also be used, which provide an ability to visually screen for transformants, such as luciferase or green fluorescent protein (GFP), or a gene expressing a beta glucuronidase or uidA gene (GUS) for which various chromogenic substrates are known. In some embodiments, a vector or polynucleotide provided herein comprises at least one selectable marker gene selected from the group consisting of nptII, aph IV, aadA, aac3, aacC4, bar, pat, DMO, EPSPS, aroA, GFP, and GUS. Plant transformation may also be carried out in the absence of selection during one or more steps or stages of culturing, developing or regenerating transformed explants, tissues, plants and/or plant parts.

According to present embodiments, methods for transforming a plant cell, tissue or explant with a recombinant DNA molecule or construct may further include site-directed or targeted integration. According to these methods, a portion of a recombinant DNA donor template molecule (i.e., an insertion sequence) may be recombined, inserted or integrated at a desired site or locus within the plant genome. The insertion sequence of the donor template may comprise a polynucleotide sequence designed to introduce a deletion and/or premature stop codon into an endogenous br2 gene sequence of a corn or maize plant. The donor template may also have one or two homology arms flanking the insertion sequence to promote the targeted insertion event through homologous recombination and/or homology-directed repair. Each homology arm may be at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence within the genome of a corn or maize plant), such as SEQ ID NO: 1 or 2. Thus, a recombinant DNA molecule of the present disclosure may comprise a donor template for site-directed or targeted integration of a deletion and/or premature stop codon into an endogenous br2 gene sequence of a corn or maize plant.

Any site or locus within the genome of a plant may potentially be chosen for site-directed integration of a transgene, construct or transcribable DNA sequence provided herein. For site-directed integration, a double-strand break (DSB) or nick may first be made at a selected genomic locus with a site-specific nuclease, such as, for example, a zinc-finger nuclease (ZFN), an engineered or native meganuclease, a TALE-endonuclease (TALEN), or an RNA-guided endonuclease (e.g., Cas9 or Cpf1). Any method known in the art for site-directed integration may be used. In the presence of a donor template molecule with an insertion sequence, the DSB or nick may then be repaired by homologous recombination between homology arm(s) of the donor template and the plant genome, or by non-homologous end joining (NHEJ), resulting in site-directed integration of the insertion sequence into the plant genome to create the targeted insertion event at the site of the DSB or nick. Thus, site-specific insertion or integration of a transgene, construct or sequence may be achieved.

A site-specific nuclease provided herein may be selected from the group consisting of a zinc-finger nuclease (ZFN), a meganuclease, an RNA-guided endonuclease, a TALEN, a recombinase, a transposase, or any combination thereof. Sec, e.g., Khandagale, K. et al., "Genome editing for targeted improvement in plants," *Plant Biotechnol Rep* 10:327-343 (2016); and Gaj, T. et al., "ZFN, TALEN and CRISPR/Cas-based methods for genome engineering," *Trends Biotechnol.* 31(7): 397-405 (2013), the contents and disclosures of which are incorporated herein by reference. A recombinase may be a serine recombinase attached to a DNA recognition motif, a tyrosine recombinase attached to a DNA recognition motif or other recombinase enzyme known in the art. A recombinase or transposase may be a DNA transposase or recombinase attached to a DNA binding domain. A tyrosine recombinase attached to a DNA recognition motif may be selected from the group consisting of a Cre recombinase, a Flp recombinase, and a Tnp1 recombinase. According to some embodiments, a Cre recombinase or a Gin recombinase provided herein is tethered to a zinc-finger DNA binding domain. In another embodiment, a serine recombinase attached to a DNA recognition motif provided herein is selected from the group consisting of a PhiC31 integrase, an R4 integrase, and a TP-901 integrase. In another embodiment, a DNA transposase attached to a DNA binding domain provided herein is selected from the group consisting of a TALE-piggyBac and TALE-Mutator.

According to embodiments of the present disclosure, an RNA-guided endonuclease may be selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Csc2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, and homologs or modified versions thereof, Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo) and homologs or modified versions thereof. According to some embodiments, an RNA-guided endonuclease may be a Cas9 or Cpf1 (or Cas12a) enzyme.

In an aspect, a site-specific nuclease provided herein is selected from the group consisting of a zinc-finger nuclease, a meganuclease, an RNA-guided nuclease, a TALEN, a recombinase, a transposase, or any combination thereof. In another aspect, a site-specific nuclease provided herein is selected from the group consisting of a Cas9 or a Cpf1 (or Cas12a). In another aspect, a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, an RNA-guided nuclease provided herein is selected from the group consisting of a Cas9 or a Cpf1 (or Cas12a). In another aspect, an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

For RNA-guided endonucleases, a guide RNA (gRNA) molecule is further provided to direct the endonuclease to a target site in the genome of the plant via base-pairing or hybridization to cause a DSB or nick at or near the target site. The gRNA may be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. As understood in the art, a "guide RNA" may comprise, for example, a CRISPR RNA (crRNA), a single-chain guide RNA (sgRNA), or any other RNA molecule that may guide or direct an endonuclease to a specific target site in the genome. A "single-chain guide RNA" (or "sgRNA") is a RNA molecule comprising a crRNA covalently linked a tracrRNA by a linker sequence, which may be expressed as a single RNA transcript or molecule. The guide RNA comprises a guide or targeting sequence that is identical or complementary to a target site within the plant genome, such as at or near a br2 gene. A protospacer-adjacent motif (PAM) may be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. Sec, e.g., Wu, X. et al., "Target specificity of the CRISPR-Cas9 system," *Quant Biol.* 2 (2): 59-70 (2014), the content and disclosure of which is incorporated herein by reference. The genomic PAM sequence on the sense (+) strand adjacent to the target site (relative to the targeting sequence of the guide RNA) may comprise 5'-NGG-3'. However, the corresponding sequence of the guide RNA (i.e., immediately downstream (3') to the targeting sequence of the guide RNA) may generally not be complementary to the genomic PAM sequence. The guide RNA may typically be a non-coding RNA molecule that does not encode a protein. The guide sequence of the guide RNA may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

According to some embodiments, a recombinant DNA construct or vector may comprise a first polynucleotide sequence encoding a site-specific nuclease and a second polynucleotide sequence encoding a guide RNA that may be introduced into a plant cell together via plant transformation techniques. Alternatively, two recombinant DNA constructs or vectors may be provided including a first recombinant DNA construct or vector and a second DNA construct or vector that may be introduced into a plant cell together or sequentially via plant transformation techniques, wherein the first recombinant DNA construct or vector comprises a polynucleotide sequence encoding a site-specific nuclease and the second recombinant DNA construct or vector comprises a polynucleotide sequence encoding a guide RNA. According to some embodiments, a recombinant DNA construct or vector comprising a polynucleotide sequence encoding a site-specific nuclease may be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA may be introduced via plant transformation techniques into a plant cell that already comprises (or is transformed with) a recombinant DNA construct or vector comprising a polynucleotide sequence encoding a site-specific nuclease. According to yet further embodiments, a first plant comprising (or transformed with) a recombinant DNA construct or vector comprising a polynucleotide sequence encoding a site-specific nuclease may be crossed with a second plant comprising (or transformed with) a recombinant DNA construct or vector comprising a polynucleotide sequence encoding a guide RNA. Such recombinant DNA constructs or vectors may be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif. The protein structure of the site-specific nuclease (or the fused/attached/tethered DNA binding domain) may target the site-specific nuclease to the target site. According to many of these embodiments, non-RNA-guided site-specific nucleases, such as recombinases, zinc finger nucleases (ZFNs), meganucleases, and TALENs, may be designed, engineered and constructed according to known methods to target and bind to a target site at or near the genomic locus of an endogenous br2 gene of a corn plant to create a DSB or nick at such genomic locus to knockout or knockdown expression of the br2 gene via repair of the DSB or nick. For example, an engineered site-specific nuclease, such as a recombinase, zinc finger nuclease (ZFN), meganuclease, or TALEN, may be designed to target and bind to a target site within the genome of a plant corresponding to a sequence within SEQ ID NO: 1 or 2, or its complementary sequence, to create a DSB or nick at the genomic locus for the br2 gene, which may then lead to the creation of a mutation or deletion of a sequence at the site of the DSB or nick, through cellular repair mechanisms, which may be guided by a donor molecule or template.

In an aspect, a targeted genome editing technique described herein may comprise the use of a recombinase. In some embodiments, a tyrosine recombinase attached, etc., to a DNA recognition domain or motif may be selected from the group consisting of a Cre recombinase, a Flp recombinase, and a Tnp1 recombinase. In an aspect, a Cre recombinase or a Gin recombinase provided herein may be tethered to a zinc-finger DNA binding domain. The Flp-FRT site-directed recombination system may come from the 2μ plasmid from the baker's yeast *Saccharomyces cerevisiae*. In this system, Flp recombinase (flippase) may recombine sequences between flippase recognition target (FRT) sites. FRT sites comprise 34 nucleotides. Flp may bind to the "arms" of the FRT sites (one arm is in reverse orientation) and cleaves the FRT site at either end of an intervening nucleic acid sequence. After cleavage, Flp may recombine nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase may recombine a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated), and recombination is complete. In another aspect, a lox site provided herein is a loxP, lox 2272, loxN, lox 511, lox 5171, lox71, lox66, M2, M3, M7, or M11 site.

ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions −1, +2, +3, and +6 relative to the start of the zinc finger α-helix, which contribute to site-specific binding to the target site, can be changed and customized to fit specific target sequences. The other amino acids may form a consensus backbone to generate ZFNs with different sequence specificities. Methods and rules for designing ZFNs for targeting and binding to specific target sequences are known in the art. Sec, e.g., US Patent App. Nos. 2005/0064474, 2009/0117617, and 2012/0142062, the contents and disclosures of which are incorporated herein by reference. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a br2 gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs may be introduced as ZFN proteins, as polynucleotides encoding ZFN proteins, and/or as combinations of proteins and protein-encoding polynucleotides.

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant, such as at or near the genomic locus of a br2 gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs are artificial restriction enzymes generated by fusing the transcription activator-like effector (TALE) DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN also refers to one or both members of a pair of TALENs that work together to cleave DNA at the same site.

Transcription activator-like effectors (TALEs) can be engineered to bind practically any DNA sequence, such as at or near the genomic locus of a br2 gene in a plant. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLOS One*. 8: c82539). MutH is capable of introducing strand-specific nicks in DNA (see Gabsalilow et al. 2013. *Nucleic Acids Research*. 41: c83). TevI introduces double-stranded breaks in DNA at targeted sites (see Beurdeley et al., 2013. *Nature Communications*. 4:1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39: e82; and tale-nt.cac.cornell.edu/about. In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation). See, e.g., US Patent App. Nos. 2011/0145940, 2011/0301073, and 2013/0117869, the contents and disclosures of which are incorporated herein by reference.

For purposes of the present disclosure, a "plant" includes an explant, plant part, seedling, plantlet or whole plant at any stage of regeneration or development. As used herein, a "plant part" may refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure may be viable, nonviable, regenerable, and/or non-regenerable. A "propagule" may include any plant part that can grow into an entire plant.

Embodiments of the present disclosure further include methods for making or producing transgenic or modified plants described here, such as by transformation, genome editing, mutating, crossing, etc., wherein the method comprises introducing a recombinant DNA molecule, construct or sequence of interest into a plant cell, or editing or mutating the genomic locus of an endogenous br2 gene, and then regenerating or developing the transgenic or modified plant from the transformed or edited plant cell, which may be performed under selection pressure. Such methods may comprise transforming a plant cell with a recombinant DNA molecule, construct or sequence of interest, and selecting for a plant having a desired mutation or edit and/or one or more altered phenotypes or traits, such as one or more of the following traits at one or more stages of development: shorter or semi-dwarf stature or plant height, shorter internode length in one or more internode(s), increased stalk/stem diameter, improved lodging resistance, reduced green snap, deeper roots, increased leaf area, earlier canopy closure, increased foliar water content and/or higher stomatal conductance under water limiting conditions, reduced anthocyanin content and/or area in leaves under normal or nitrogen or water limiting stress conditions, improved yield-related traits including a larger female reproductive organ or ear, an increase in ear weight, harvest index, yield, seed or kernel number, and/or seed or kernel weight, increased stress tolerance, such as increased drought tolerance, increased nitrogen utilization, and/or increased tolerance to high density planting, as compared to a wild type or control plant.

According to another aspect of the present disclosure, methods are provided for planting a modified plant(s) provided herein at a normal/standard or high density in field. According to some embodiments, the yield of a crop plant per acre (or per land area) may be increased by planting a modified or transgenic plant(s) of the present disclosure at a higher density in the field. As described herein, modified plants having a genome-edited br2 gene, may have reduced plant height, shorter internode(s), increased stalk/stem diameter, and/or increased lodging resistance. It is proposed that modified or transgenic plants may tolerate high density planting conditions since an increase in stem diameter may resist lodging and the shorter plant height may allow for increased light penetrance to the lower leaves under high density planting conditions. Thus, modified plants provided herein may be planted at a higher density to increase the yield per acre (or land area) in the field. For row crops, higher density may be achieved by planting a greater number of seeds/plants per row length and/or by decreasing the spacing between rows.

According to some embodiments, a modified crop plant may be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified crop plant may be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre. As an example, corn plants may be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

Corn leaves consist of four main anatomical parts: a proximal sheath, a ligule, an auricle, and a distal blade. The sheath wraps around the stem and younger leaves, while the blade is flattened in the mediolateral axis (midrib to margin). The ligule and auricle are found at the blade/sheath boundary; the ligule is an adaxial (upper) membranous structure that acts as a collar around the stem, and the auricle is a projection on the lower surface of the blade base that connects the blade to the sheath. Stages of corn plant growth are divided into vegetative (V) stages and reproductive (R) stages. Upon germination, a corn plant is in the VE stage (emergence). Once the first leaf collar (e.g., the ligule) is visible, the corn plant is in the V1 stage. The emergence of the second leaf collar signifies V2 stage; the emergence of the third leaf collar signifies the V3 stage; and so on until the tassel emerges. For example, if twelve leaf collars are visible, the plant is a V12 stage plant. Once the bottom-most branch of the tassel emerges the plant is in VT stage, which is the final vegetative stage. The reproductive stage of growth occurs after the vegetative stage. The number of vegetative stages prior to VT stage can vary by environment and corn line. The first reproductive stage (R1; silking stage) occurs when silk is visible outside the husk leaves surrounding an ear of corn. R2 (blistering stage) occurs when corn kernels are white on the outside and are filled with a clear liquid inside. R3 (milk stage) occurs when the kernels are yellow on the outside and are filled with a milky white fluid inside. R4 (dough stage) occurs when the kernels are filled with a thick, or pasty, fluid. In some corn lines the cob will also turn pink or red at this stage. R5 (dent stage) occurs when a majority of the kernels are at least partially dented. The final reproductive stage, R6 (physiological maturity), occurs when the kernels have attained their maximum dry weight.

The height of a corn plant can be measured using a variety of methods known in the art. The height of a corn plant can also be determined based on a variety of anatomical locations on a corn plant. In an aspect, the height of a corn plant is measured as the distance between the soil or ground and the ligule of the uppermost fully-expanded leaf of the corn plant. As used herein, a “fully-expanded leaf” is a leaf where the leaf blade is exposed and both the ligule and auricle are visible at the blade/sheath boundary. In another aspect, the height of a corn plant is measured as the distance between the soil or ground and the upper leaf surface of the leaf farthest from the soil. In another aspect, the height of a corn plant is measured as the distance between the soil or ground and the arch of the highest corn leaf that is at least 50% developed. As used herein, an “arch of the highest corn leaf” is the highest point of the arch of the uppermost leaf of the corn plant that is curving downward. In another aspect, the height of a corn plant is measured at the first reproductive (R1) stage. Exemplary, non-limiting methods of measuring plant height include comparing photographs of corn plants to a height reference, or physically measuring individual corn plants with a suitable ruler. Unless otherwise specified, corn plant heights are measured at R1 stage. Those in the art recognize that, when comparing a modified corn plant to a control corn plant, the measurements must be made at the same stage of growth. It would be improper, as a non-limiting example, to compare the height of a modified corn plant at R3 stage to the height of a control corn plant at V6 stage, even if both plants had been growing for the same amount of time.

As used herein, the term “ground” or “ground level” used in relation to a corn plant, such as to measure plant height, refers to the top or uppermost surface of the growth medium or soil (e.g., earth) from which the corn plant grows.

Corn plant height varies depending on the line or variety grown, whether the plant is a hybrid or inbred, and environmental conditions. Although hybrid corn plants can reach a height of over 2.5 meters, 3.0 meters, or even 3.5 or 3.6 meters tall by maturity, a height of around 2.0-2.5 meters by maturity for hybrid plants is more common.

According to embodiments of the present disclosure, a modified corn plant(s) is/are provided that comprise (i) a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or (ii) an ear height of at least 500 mm, at least 600 mm, at least 700 mm, at least 800 mm, at least 900 mm, at least 1000 mm, at least 1100 mm, at least 1200 mm, at least 1300 mm, at least 1400 mm, or at least 1500 mm. Any such plant height trait or range that is expressed in millimeters (mm) may be converted into a different unit of measurement based on known conversions (e.g., one inch is equal to 2.54 cm or 25.4 millimeters, and millimeters (mm), centimeters (cm) and meters (m) only differ by one or more powers of ten). Thus, any measurement provided herein is further described in terms of any other comparable units of measurement according to known and established conversions. However, the exact plant height and/or ear height of a modified corn plant may depend on the environment and genetic background. Thus, the change in plant height and/or car height of a modified corn plant may instead be described in terms of a minimum difference or percent change relative to a control plant. A modified corn plant may further comprise at least one ear that is substantially free of male reproductive tissues or structures or other off-types.

According to embodiments of the present disclosure, modified corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an ear height of between 500 mm and 1500 mm, between 600 mm and 1500 mm, between 700 and 1500 mm, between 800 mm and 1500 mm, between 900 mm and 1500 mm, between 1000 mm and 1500 mm, between 1100 mm and 1500 mm, between 1200 mm and 1500 mm, between 1300 mm and 1500 mm, between 1400 mm and 1500 mm, between 500 mm and 1200 mm, between 500 mm and 1000 mm, between 500 mm and 800 mm, between 500 mm and 600 mm, between 600 mm and 1200 mm, between 600 mm and 1000 mm, or between 600 mm and 800 mm. A modified corn plant may be substantially free of off-types, such as male reproductive tissues or structures in one or more cars of the modified corn plant.

According to embodiments of the present disclosure, modified corn plants are provided that have (i) a plant height that is at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a wild-type or control plant, and/or (ii) an ear height that is within at least 5%, at least 10%, at least 15%, at least 20%, at least 25%, at least 30%, at least 35%, at least 40%, at least 45%, at least 50% of the ear height of the wild-type or control plant. According to embodiments of the present disclosure, a modified corn plant may have a reduced plant height that is no more than 20%, 25%, 30%, 35%, 40%, 45%, 50%, 55%, or 60% shorter than the height of a wild-type or control plant, and/or an ear height that is within 10%, 15%, 20%, 25%, 30%, 35%, 40%, 45%, or 50% of the ear height of a wild-type or control plant. For example, a modified plant may have (i) a plant height that is at least 10%, at least 15%, or at least 20% less or shorter (i.e., greater than or equal to 10%, 15%, or 20% shorter), but not greater or more than 50% shorter, than a wild type or control plant, and/or (ii) an car height that is within 5%, 10%, or 15% than a wild type or control plant. For clarity, the phrases "at least 20% shorter" and "greater than or equal to 20% shorter" would exclude, for example, 10% shorter. For clarity, the phrases "not greater than 50% shorter", "no more than 50% shorter" and "not more than 50% shorter" would exclude 60% shorter; the phrase "at least 5% greater" would exclude 2% greater; and the phrases "not more than 30% greater" and "no more than 30% greater" would exclude 40% greater.

According to embodiments of the present disclosure, modified corn plants are provided that comprise a height between 2.5% and 75%, between 2.5% and 50%, between 2.5% and 40%, between 2.5% and 30%, between 2.5% and 25%, between 2.5% and 20%, between 2.5% and 15%, between 2.5% and 12.5%, between 2.5% and 10%, between 2.5% and 7.5%, between 2.5% and 5%, between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the height of a wild-type or control plant, and/or an ear height that is within between 5% and 50%, between 5% and 45%, between 5% and 40%, between 5% and 35%, between 5% and 30%, between 5% and 25%, between 5% and 20%, between 5% and 15%, between 5% and 10%, between 10% and 50%, between 10% and 45%, between 40% and 35%, between 10% and 30%, between 10% and 25%, between 10% and 20%, between 10% and 15%, between 25% and 45%, between 25% and 40%, between 20% and 50%, between 8% and 20%, or between 8% and 15% of the ear height of the wild-type or control plant.

As used herein, "internode length" refers to the distance between two consecutive internodes on the stem of a plant. According to embodiments of the present disclosure, modified corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a wild-type or control plant. The "minus-2 internode" of a corn plant refers to the second internode below the ear of the plant, and the "minus-4 internode" of a corn plant refers to the fourth internode below the ear of the plant According to many embodiments, modified corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a wild-type or control plant.

According to embodiments of the present disclosure, modified corn plants are provided that comprise an ear weight (individually or on average) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% greater than the ear weight of a wild-type or control plant. A modified corn plant provided herein may comprise an ear weight that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% greater than the ear weight of a wild-type or control plant.

According to embodiments of the present disclosure, modified corn plants are provided that have a harvest index of at least 0.57, at least 0.58, at least 0.59, at least 0.60, at least 0.61, at least 0.62, at least 0.63, at least 0.64, or at least 0.65 (or greater). A modified corn plant may comprise a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. A modified corn plant may have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant may have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a wild-type or control plant.

According to embodiments of the present disclosure, modified corn plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant may have an increase in harvestable yield between 1 and 10, between 1 and 8, between 2 and 8, between 2 and 6, between 2 and 5, between 2.5 and 4.5, or between 3 and 4 bushels per acre. A modified corn plant may have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant may have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a wild-type or control plant.

According to embodiments of the present disclosure, a modified corn plant is provided that has a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a wild-type or control plant. A modified corn plant may have a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a wild-type or control plant. Further provided are populations of corn plants having increased lodging resistance and a reduced lodging frequency. Populations of modified corn plants are provided having a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a population of wild-type or control plants. A population of modified corn plants may comprise a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a population of wild-type or control plants, which may be expressed as an average over a specified number of plants or crop area of equal density.

According to embodiments of the present disclosure, modified corn plants are provided having a significantly reduced or decreased plant height (e.g., 2000 mm or less) and a similar ear height, relative to a wild-type or control plant. According to these embodiments, the decrease or reduction in plant height may be within any of the height or percentage ranges recited herein. Such modified corn plants having a reduced plant height relative to a wild-type or control plant may be transformed with a transcribable DNA sequence encoding a non-coding RNA molecule that targets at least one br2 gene for suppression. Modified corn plants having a significantly reduced plant height relative to a wild-type or control plant may further have at least one ear that is substantially free of male reproductive tissues or structures and/or other off-types. According to many embodiments, modified corn plants comprise a mutant allele of an endogenous br2 gene as provided herein. According to some embodiments, modified corn plants having a significantly reduced plant height relative to a wild-type or control plant may further have an increased harvest index and/or increased lodging resistance relative to the wild-type or control plant.

According to embodiments of the present invention, modified corn plants are provided having a reduced gibberellin content (in active form) in at least the stem and internode tissue(s), such as the stem, internode, leaf and/or vascular tissue(s), as compared to the same tissue(s) of wild-type or control plants. According to many embodiments, modified corn plants are provided having a significantly reduced plant height and/or a significantly increased stem diameter relative to wild-type or control plants, wherein the modified corn plants further have significantly reduced or decreased level(s) of one or more auxin or indole-3-acetic acid (IAA) hormones in one or more of the stem, node, internode, leaf and/or vascular tissue(s), relative to the same tissue(s) of the wild-type or control plants. For example, the level of one or more auxins or IAAs in the stem, internode or one or more internodes, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than in the same tissue(s) of a wild-type or control corn plant.

According to some embodiments, a modified corn plant may comprise levels of one or more auxin or indole-3-acetic acid (IAA) hormones in one or more of the stem, node(s), internode(s), leaf and/or vascular tissue(s) that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or (or lower) than in the same tissue(s) of a wild-type or control corn plant. A modified corn plant having a reduced one or more auxin or indole-3-acetic acid (IAA) hormones in one or more of the stem, node(s), internode(s), leaf and/or vascular tissue(s), or any portion thereof, may further be substantially free of off-types, such as male reproductive tissues or structures and/or other off-types in at least one ear of a modified corn plant.

According to many embodiments, a modified corn plant is provided comprising a significantly reduced plant height relative to wild-type or control plants, wherein the modified corn plant has a mutant allele of an endogenous br2 gene, wherein the mutant allele of the br2 gene encodes a truncated Br2 protein as provided herein, such truncated Br2 protein having a reduced and/or altered activity relative to a wild-type Br2 protein. Such mutant allele of the br2 gene may be dominant or semi-dominant and/or may interact and interfere with the function of a wild-type Br2 protein.

A modified corn plant having a mutant allele of an endogenous br2 gene as provided herein may also be substantially free of off-types, such as male reproductive tissues or structures and/or other off-types in at least one ear of the modified corn plant.

Methods and techniques are provided for screening for, and/or identifying, cells or plants, etc., for the presence of targeted edits or transgenes, and selecting cells or plants comprising targeted edits or transgenes, which may be based on one or more phenotypes or traits, or on the presence or absence of a molecular marker or polynucleotide or protein sequence in the cells or plants. Nucleic acids can be isolated and detected using techniques known in the art. For example, nucleic acids can be isolated and detected using, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis. Any method known in the art may be used to screen for, and/or identify, cells, plants, etc., having a transgene or genome edit in its genome, which may be based on any suitable form of visual observation, selection, molecular technique, etc.

In some embodiments, methods are provided for detecting recombinant nucleic acids and/or polypeptides in plant cells. For example, nucleic acids may be detected using hybridization probes or through production of amplicons using PCR with primers as known in the art. Hybridization between nucleic acids is discussed in Sambrook et al. (1989, Molecular Cloning: A Laboratory Manual, 2nd Ed., Cold Spring Harbor Laboratory Press, Cold Spring Harbor, NY). Polypeptides can be detected using antibodies. Techniques for detecting polypeptides using antibodies include enzyme linked immunosorbent assays (ELISAs), Western blots, immunoprecipitations, immunofluorescence, and the like. An antibody provided herein may be a polyclonal antibody or a monoclonal antibody. An antibody having specific binding affinity for a polypeptide provided herein can be generated using methods known in the art. An antibody or hybridization probe may be attached to a solid support, such as a tube, plate or well, using methods known in the art.

Detection (e.g., of an amplification product, of a hybridization complex, of a polypeptide) can be accomplished using detectable labels that may be attached or associated with a hybridization probe or antibody. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified plants, plant parts or plant cells can be through any methodologies known to those skilled in the art of molecular biology. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina®, PacBio®, Ion Torrent™, etc.) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known in the art.

According to embodiments of the present disclosure, a modified corn plant or plant part, one or more modified corn plants or plant parts, or a plurality modified corn plants or plant parts as provided herein, or an agricultural field or soil in which a modified corn plant or plant part, one or more modified corn plants or plant parts or a plurality modified corn plants or plant parts as provided herein are planted or grown, can be treated with an agricultural composition comprising one or more active ingredients or other agents, such as, for example and without limitation, a pesticide or one or more pesticides, an herbicide or one or more herbicides, a fungicide or one or more fungicides, an insecticide or one or more insecticides, a plant growth regulator or plant stimulant or one or more plant growth regulators and/or plant stimulants, and/or a safener or one or more safeners. Agricultural compositions may comprise one or any combination or multiplicity of these actives, agents or compounds. Such an agricultural composition may be applied, for example, as a foliar, soil or in-furrow treatment, as a pre-emergent, pre-sowing and/or post-emergent treatment, and/or in some cases, may be applied to modified or transgenic plant part or seed provided herein.

An agricultural composition may be formulated according to its intended use and application. The appropriate formulation of the agricultural composition may be chosen to have different physicochemical parameters, components and stabilities of the respective compound(s). Possible types of formulations for an agricultural composition can include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes. If appropriate, some agricultural compositions of a pesticidal compound or one or more pesticidal compounds might be formulated and used as a seed coating applied to a plant part or seed as provided herein.

A modified corn plant or plant part, one or more modified corn plants or plant parts, or plurality of modified corn plants or plant parts, which may be further planted or grown in a greenhouse or an agricultural field or soil, that comprise(s) a mutant allele of a brachytic2 (br2) locus or gene as described herein, which may be homozygous, bi-allelic or heteroallelic, or heterozygous for one or more mutant allele(s) of the brachytic2 (br2) gene or locus, may further comprise one or more additional transgenic event(s) conferring an additional beneficial trait(s) to the modified or transgenic corn plant, including but not limited to, pest resistance, water use efficiency, yield performance, drought tolerance, seed quality, improved nutritional quality, hybrid seed production, and herbicide tolerance, in which the trait is measured with respect to a plant lacking such trait. Examples of such advantageous and/or useful traits may include better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products, increased resistance against animal and/or microbial pests, such as against insects, arachnids, nematodes, mites, slugs and snails, and increased resistance against phytopathogenic fungi, bacteria and/or viruses.

Examples of transgenic or other events providing an additional beneficial trait may include any of the transgenic events provided by the United States Department of Agriculture's (USDA) Animal and Plant Health Inspection Service (APHIS), which can be found at aphis.usda.gov, and/or the ISAAA (International Service for the Acquisition of Agri-Biotech Applications), which can be found at www.isaaa.org/gmapprovaldatabase.

The aforementioned additional beneficial trait(s) may be introduced into a modified corn plant or plant part by crossing or breeding a modified or transgenic corn plant comprising a mutant allele of the brachytic2 (br2) gene or locus with a transgenic corn plant comprising the transgenic event that conveys the additional beneficial trait(s) of interest, and selecting progeny plants comprising both the mutant allele of the brachytic2 (br2) gene or locus and the additional transgenic event conveying the additional beneficial trait. Such progeny can be identified with or without the help of molecular markers. The aforementioned additional beneficial trait(s) may also be introduced into a modified corn plant or plant part comprising a mutant allele of the brachytic2 (br2) gene or locus using any suitable transformation, genome editing or molecular technology or technique known in the art, including but not limited to, any particle bombardment, bacteria-mediated or *Agrobacterium*-mediated transformation, or other known plant transformation technique, Targeting Induced Local Lesions in Genomes (TILLING), and genome editing tool, such as a zinc-finger nucleases (ZFN), transcription activator-like effector nucleases (TALEN), meganucleases and CRISPR associated systems with Cas9, Cpf1 or other site-specific nuclease.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples.

EXAMPLES

Example 1. Creating Dominant Alleles by Genome Editing to Completely Delete or Truncate the Native Zm.Br2 Transcript FIG. 1 provides an illustrative set of examples for the production, through targeted genome editing, of a genetic modification of the Zm.br2 locus (see also SEQ ID NO. 1 as described herein), to encode a RNA transcript with a truncated coding region, or with the coding region completely absent, to produce a mutant allele of the endogenous Zm.br2 gene. The 5-exon Zm.Br2 gene is shown in FIG. 1 with its exons numbered in black arrows. The guide RNAs used in these examples are shown as SP1 through SP10 with their approximate targeting location in FIG. 1 according to three distinct editing schemes through the design of three different editing constructs. Targeted whole deletions of the coding sequence of the br2 gene were made using the SP1-4 guide RNAs, edits within exon 1 were made using the SP5-7 guide RNAs, and edits within exon 2 were made using the SP8-10 guide RNAs. The DNA sequences encoding these guide RNAs (spacers) and their intended target sites are listed in Table 2.

Three plant transformation constructs were designed for the three editing schemes above to create double stranded breaks (DSB) in the Zm.br2 gene to allow for cutting and imperfect repair of the DNA sequence and the spontaneous creation of insertions, deletions, and/or substitutions at or near the targeted DNA sequence or region. In this example, the constructs generally contain two functional cassettes encoding gene editing machinery for creation of targeted mutations in the Zm.br2 gene: (i) a first cassette for expression of a Cpf1 or Cas 12a variant protein, and (ii) a second cassette for expression of the three relevant guide RNAs targeting the Zm.Br2 gene locus for each editing scheme. Each guide RNA contains a common scaffold compatible with the Cpf1 mutant, and a unique spacer/targeting sequence complementary to its intended target site. The Cpf1 expression cassette comprises a maize ubiquitin promoter (SEQ ID NO: 9) operably linked to a sequence encoding a Lachnospiraceae bacterium Cpf1 RNA-guided endonuclease enzyme (SEQ ID NO: 10) fused to a nuclear localization signal at both the 5' and 3' ends of the transcript (SEQ ID NO: 11).

For whole deletions of the entire coding sequence of the Zm.br2 gene, the expression cassette for the guide RNAs comprised a sequence encoding four guide RNAs (sequences encoded by SP1, SP2, SP3, and SP4 are provided in Table 2 below; see also FIG. 1) that target four sites at the Zm.Br2 gene locus. The coding sequence for these guide RNAs was operably linked to a maize RNA polymerase III (Pol3) promoter (SEQ ID NO: 22). Two of the target sites for these guide RNAs are upstream of the start codon (SP1 and SP2), and the two other target sites for these guide RNAs are downstream of the stop codon (SP3 and SP4).

The expression cassette encoding guide RNAs targeting the first exon of the Zm.br2 gene comprised a sequence encoding three guide RNAs (sequences encoded by the SP5, SP6, and SP7 DNA sequences in Table 2 below; see also FIG. 1) that target three sites in exon 1 of the Zm.Br2 gene. The coding sequence for these guide RNAs was operably linked to a maize RNA polymerase III (Pol3) promoter (SEQ ID NO: 22).

The expression cassette encoding guide RNAs targeting the second exon of the Zm.br2 gene comprised a sequence encoding three guide RNAs (sequences encoded by the SP8, SP9, and SP10 DNA sequences in Table 2 below; see also FIG. 1) that target three sites in exon 2 of the Zm.Br2 gene. The coding sequence for these guide RNAs was operably linked to a maize RNA polymerase III (Pol3) promoter (SEQ ID NO: 22).

TABLE 2

Example guide RNAs used for editing the Zm.Br2 locus

| SEQ ID | Guide RNA spacer | Deletion target | Sequence |
|---|---|---|---|
| 12 | SP1 | Gene | GATCTCTATATACTGTCACTCGC |
| 13 | SP2 | Gene | GTCTCTTCTTAATATAAATACCG |
| 14 | SP3 | Gene | GGATGATGTAAACCTTCACTCGC |
| 15 | SP4 | Gene | GCCGCTGCCAATCCACCGATCCC |
| 16 | SP5 | Exon1 | CTAGCCGGGCAACCGGAAGCAGC |
| 17 | SP6 | Exon1 | CTCGTCGTCGGAGCGGCAATCTG |
| 18 | SP7 | Exon1 | CCGCTCCGACGACGAGGAAGTAG |
| 19 | SP8 | Exon2 | GGTACCGGATCCGCATCCGCGTC |
| 20 | SP9 | Exon2 | CGTTGATGGCGTAGATCACGTCC |
| 21 | SP10 | Exon2 | TCATGATCGGCGGACTGTAAGGC |

Example 2. Creation and Identification of Edits at R0 Generation

An inbred corn plant line was transformed via *Agrobacterium*-mediated transformation with one of the transformation vectors described above in Example 1. The transformed plant tissues were grown to mature R0 plants. R0 plants were selfed to produce R1 seed. To determine the size and sequence of edits in the endogenous Zm.br2 gene of the R0 and R1 plants, a PCR assay was performed, and resulting amplicons were either analyzed by gel electrophoresis or sequencing. One approach to identify deletions between spacers SP1 or SP2 and SP3 or SP4 used a PCR primer pair including one primer (SEQ ID NO: 23) hybridizing to a sequence upstream of spacer SP1, and another primer (SEQ ID NO: 24) hybridizing to a sequence downstream of spacer SP4. Wildtype amplicons would be over 9 kbp in length, which would be unlikely to amplify with standard PCR conditions. Amplicons including editing-induced deletions between spacers SP1 or SP2 and SP3 or SP4 would be about 1 kb to 3 kb in length. An approach to identify sequences that did not have a complete gene deletion used a PCR primer pair including one primer (SEQ ID NO: 23) hybridizing upstream of spacer SP1, and another primer (SEQ ID NO: 25) hybridizing to a sequence downstream of spacer SP2. Amplicons with this primer pair that did not have an editing-induced deletion between spacers SP1 or SP2 and SP3 or SP4 would be approximately 789 bp in length. Sequencing can be used in any case to determine the exact sequence changes for a given edited mutation.

One approach to identify deletions between spacers SP5, SP6, and SP7 in exon 1, or SP8, SP9, and SP10 for exon 2, used a PCR primer pair including one primer (SEQ ID NO: 26) hybridizing upstream of spacer SP5 and another primer (SEQ ID NO: 27) hybridizing to downstream of spacer SP10.

Thus, the presence and size of the PCR fragments using these approaches would show whether a deletion occurred between target sites. The genomic DNA or PCR product of the edited mutant allele can also be sequenced to identify smaller deletions or other mutations not easily visualized on an electrophoresis gel to determine specific edited mutations and/or sequence junctions. Based on these sequencing results, gene models of the edited sequences were created. All edits retrieved in this experiment are described in Table 3 with junction sequences for each of the deletions. Edit IDs 1 and 2 would not produce a Zm.Br2 protein because the entire coding sequence is deleted, but the predicted amino acid sequences of the truncated Zm.Br2 proteins encoded by the mutant alleles of the Zm.br2 locus or gene with Edit ID 3, 4 or 5 are provided as SEQ ID NOs: 52, 53, and 54, respectively. R0 plants were selfed to produce R1 seed. R1 plants were assayed in a similar fashion by PCR and sequencing to confirm the results.

TABLE 3

Deletions identified at R0 and confirmed by sequencing at R1

| R0 plant ID | Edit ID | Edit description | SEQ ID of edit junction | SEQ ID of predicted protein from edit junction |
|---|---|---|---|---|
| 1 | 1 | 8366 bp deletion of gene | SEQ ID NO: 4 | |
| 2 | 2 | 8358 bp deletion of gene | SEQ ID NO: 5 | |
| 3 | 3 | 6 bp deletion in exon1 | SEQ ID NO: 6 | SEQ ID NO: 52 |
| 4 | 4 | 621 bp deletion in exon2 | SEQ ID NO: 7 | SEQ ID NO: 53 |
| 5 | 5 | 507 bp deletion in exon2 | SEQ ID NO: 8 | SEQ ID NO: 54 |

Example 3. Description of R1 Plants and Related Phenotypic Data

As mentioned in Example 2, R0 plants were selfed to produce R1 plants. R1 plants were first screened by PCR to identify nuclease-null and edit-positive plants. Sequencing of PCR products (as described in Example 2) was used to determine zygosity of plants, whether homozygous (HOM) or heterozygous (HET) for the edit. Wildtype (WT) plants were devoid of the edit. R1 plants that were transplanted and kept to maturity are summarized in Table 4. All of these R1 plants in Table 4 were nuclease-null, so no new edits in R1 plants or subsequent generations should be observed. Edited R1 plants were phenotyped for plant height (PHT, as measured from the soil line to the base of the highest collared leaf) at 7 weeks after planting. Averages and statistical analysis of these PHT results in Table 4 for each edit (Edit ID 1-5) for a number of plants (N) are summarized in Table 5.

TABLE 4

Nuclease-negative, edit positive R1 plants kept to maturity with PHT at 7 weeks.

| Plant ID | Edit ID | Inbred ID | Edit Zygosity | Female Parent Plant ID | 7-week plant height (in inches) |
|---|---|---|---|---|---|
| 6 | 1 | 1 | HOM | 1 | 11 |
| 7 | 1 | 1 | HOM | 1 | 11 |
| 8 | 1 | 1 | HOM | 1 | 11 |
| 9 | 1 | 1 | HOM | 1 | 11 |
| 10 | 1 | 1 | HOM | 1 | 12 |
| 11 | 1 | 1 | HOM | 1 | 12 |
| 12 | 1 | 1 | HOM | 1 | 12 |
| 13 | 1 | 1 | HOM | 1 | 11 |
| 14 | 2 | 1 | HET | 2 | 46.5 |
| 15 | 3 | 1 | HET | 3 | 38 |
| 16 | 3 | 1 | HET | 3 | 42 |
| 17 | 3 | 1 | HET | 3 | 42 |
| 18 | 4 | 1 | HET | 4 | 39 |
| 19 | 4 | 1 | HET | 4 | 38 |
| 20 | 4 | 1 | HET | 4 | 40 |
| 21 | 4 | 1 | HET | 4 | 37 |
| 22 | 4 | 1 | HET | 4 | 39 |
| 23 | 4 | 1 | HOM | 4 | 12 |
| 24 | 4 | 1 | HOM | 4 | 11 |
| 25 | 4 | 1 | HOM | 4 | 11 |
| 26 | 5 | 1 | HOM | 5 | 9 |
| 27 | 5 | 1 | HOM | 5 | 11 |
| 28 | 5 | 1 | HOM | 5 | 10 |
| 29 | 5 | 1 | HOM | 5 | 12 |
| 30 | 5 | 1 | HOM | 5 | 10 |
| 31 | 5 | 1 | HOM | 5 | 11 |
| 32 | 5 | 1 | HOM | 5 | 11 |
| 33 | WT | 1 | WT | | 41 |
| 34 | WT | 1 | WT | | 49 |
| 35 | WT | 1 | WT | | 43 |
| 36 | WT | 1 | WT | | 46 |
| 37 | WT | 1 | WT | | 40 |
| 38 | WT | 2 | WT | | 32 |
| 39 | WT | 2 | WT | | 34 |
| 40 | WT | 2 | WT | | 33 |
| 41 | WT | 2 | WT | | 35 |
| 42 | WT | 2 | WT | | 34 |
| 43 | WT | 2 | WT | | 36 |
| 44 | WT | 2 | WT | | 33 |
| 45 | WT | 2 | WT | | 32 |
| 46 | WT | 2 | WT | | 34 |
| 47 | WT | 2 | WT | | 33 |
| 48 | WT | 2 | WT | | 31 |
| 49 | WT | 2 | WT | | 31 |
| 50 | WT | 2 | WT | | 32 |
| 51 | WT | 2 | WT | | 31 |
| 52 | WT | 2 | WT | | 36 |
| 53 | WT | 2 | WT | | 32 |

TABLE 5

Statistical analysis of 7-week plant height data for nuclease-negative, edit positive R1 plants kept to maturity.

| Edit ID | Inbred ID | Edit zygosity | Average 7-week PHT | N | Standard deviation | p-value compared to WT |
|---|---|---|---|---|---|---|
| 1 | 1 | HOM | 11.375 | 8 | 0.518 | 0.000 |
| 2 | 1 | HET | 46.500 | 1 | — | — |
| 3 | 1 | HET | 40.667 | 3 | 2.309 | 0.081 |
| 4 | 1 | HET | 38.600 | 5 | 1.140 | 0.124 |
| 4 | 1 | HOM | 11.333 | 3 | 0.577 | 0.000 |
| 5 | 1 | HOM | 10.571 | 7 | 0.976 | 0.000 |
| WT | 1 | WT | 35.619 | 5 | 3.701 | — |
| WT | 2 | WT | 35.619 | 16 | 1.652 | — |

Example 4. Description of F1 Plants and Related Data

R1 edited plants of inbred 1 were (i) selfed to produce R2 seed and (ii) crossed with wildtype plants of inbred 2 to produce hybrid seed. Hybrid F1 seed was planted, and leaves were sampled one week after planting and sequenced as in Example 2 to confirm presence and zygosity of the edits. Heterozygous-edited F1 plants were advanced to maturity, and plant height was taken 6 weeks after planting and at maturity. Individual plants are described in Table 6, and statistics are summarized for a number of plants (N) in Table 7.

TABLE 6

Heterozygous-edited F1 hybrid plants with PHT at 6-weeks and maturity.

| Plant ID | Edit ID | Hybrid Cross | Edit Zygosity | Female Parent Plant ID | Male Parent Plant ID | 6-week PHT (in inches) | Mature PHT (in inches) |
|---|---|---|---|---|---|---|---|
| 54 | 1 | 1 × 2 | HET | 39 | 10 | 44 | 89 |
| 55 | 1 | 1 × 2 | HET | 39 | 10 | 43 | 88 |
| 56 | 2 | 1 × 2 | HET | 40 | 14 | 53 | 93 |
| 57 | 2 | 1 × 2 | HET | 40 | 14 | 51 | 100 |
| 58 | 2 | 1 × 2 | HET | 40 | 14 | 53 | 97 |
| 59 | 3 | 1 × 2 | HET | 41 | 17 | 32 | 77 |
| 60 | 3 | 1 × 2 | HET | 41 | 17 | 44 | 87 |
| 61 | 4 | 1 × 2 | HET | 42 | 25 | 32 | 80 |
| 62 | 5 | 1 × 2 | HET | 43 | 32 | 37 | 86 |
| 63 | 5 | 1 × 2 | HET | 43 | 32 | 34 | 78 |
| 64 | 5 | 1 × 2 | HET | 43 | 32 | 37 | 76 |
| 65 | WT | 1 × 2 | WT | 38 | 33 | 27 | 56 |
| 66 | WT | 1 × 2 | WT | 38 | 33 | 44 | 98 |

TABLE 6-continued

Heterozygous-edited F1 hybrid plants with PHT at 6-weeks and maturity.

| Plant ID | Edit ID | Hybrid Cross | Edit Zygosity | Female Parent Plant ID | Male Parent Plant ID | 6-week PHT (in inches) | Mature PHT (in inches) |
|---|---|---|---|---|---|---|---|
| 67 | WT | 1 × 2 | WT | 38 | 33 | 46 | 95 |
| 68 | WT | 1 × 2 | WT | 38 | 33 | 49 | 101 |
| 69 | WT | 1 × 2 | WT | 38 | 33 | 52 | 112 |
| 70 | WT | 1 × 2 | WT | 38 | 33 | 53 | 112 |
| 71 | WT | 1 × 2 | WT | 38 | 33 | 51 | 104 |

TABLE 7

Statistical analysis of plant height data at 7-weeks and maturity for heterozygous-edited F1 plants.

| Edit ID | Hybrid Cross | N | Average 7-week plant height | Standard deviation | p-value compared to WT | Average maturity plant height | Standard deviation | p-value compared to WT |
|---|---|---|---|---|---|---|---|---|
| 1 | 1 × 2 | 2 | 43.500 | 0.707 | 0.07656 | 88.500 | 0.707 | 0.00001 |
| 2 | 1 × 2 | 3 | 52.333 | 1.155 | 0.18660 | 96.667 | 3.512 | 0.00000 |
| 3 | 1 × 2 | 2 | 38.000 | 8.485 | 0.02787 | 82.000 | 7.071 | 0.00009 |
| 4 | 1 × 2 | 1 | 32.000 | — | — | 80.000 | — | — |
| 5 | 1 × 2 | 3 | 36.000 | 1.732 | 0.00058 | 80.000 | 5.292 | 0.00001 |
| WT | 1 × 2 | 6 | 49.167 | 3.545 | — | 103.667 | 7.118 | — |

Example 5. Hybrid Field Experiment

TABLE 8

R3 seed inventory as sources of hybrid plants.

| R2 parent plant ID | Edit ID | R2 parent Inbred ID |
|---|---|---|
| 74 | 1 | 1 |
| 77 | 3 | 1 |
| 83 | 4 | 1 |

R2 edited plants from Example 4 were selfed to produce R3 homozygous edited plants, which are described in Table 8. These R3 plants of Inbred 1 were crossed with wildtype plants of Inbred 2 to produce hybrid seeds. Hybrid control seeds were also produced by crossing wildtype plants of Inbred 1 with wildtype plants of Inbred 2 in the same nursery. Plants of three of the Zm.Br2 heterozygous-edited hybrids and one control hybrid were planted in the field in a Group Unbalanced Block Design. The entries were grouped by plant height to account for potential height differences between the hybrids, with 11 to 15 replicates per entry. Plant height for each entry was measured at maturity (Table 9).

The mature plant height of the heterozygous-edited hybrids was comparable to or taller than their wildtype (WT) hybrid counterparts. This difference between observed phenotype in the controlled environment versus field environment could be due in part to environmental factors during the field growing season. The growing season experienced non-ideal temperature and precipitation, resulting in the deactivation of some plots due to low germination. Also, as Zm.Br2 is an auxin transporter, and auxin is known to play a central role in plant environmental response, different conditions in the controlled and field environments could influence gene expression and thus final plant height.

TABLE 9

Hybrid plant height at maturity in field experiment.

| Edit ID | Edited inbred parent 1 ID | Inbred parent 2 ID | Number of plots (N) | Average hybrid plant height in inches | Standard deviation | p-value compared to WT |
|---|---|---|---|---|---|---|
| 1 | 1 | 2 | 12 | 85.75 | 0.428 | 0.72 |
| 3 | 1 | 2 | 15 | 91.76 | 0.382 | 1E−15 |
| 4 | 1 | 2 | 15 | 88.22 | 0.382 | 2.21E−05 |
| WT | 1 | 2 | 11 | 85.53 | 0.447 | — |

Example 6. Characterization of Additional Edited Plants

Five additional edited alleles were created and identified by editing the second exon of Zm.Br2 using guide RNA spacers SP8, SP9, and SP10 as in Example 1. The edit junction sequences of these edited variants are described in SEQ ID NOs: 55 to 59 and are listed in Table 10. The edited variants of SEQ ID NOs: 55, 56, 57, 58, and 59 produce truncated Zm.Br2 proteins and the predicted amino acid sequences correspond to SEQ ID NOs: 60, 61, 62, 63, and 64, respectively. Though the guide RNAs were targeted to exon 2, Edit IDs 6 and 8 had deletions that extended into exon 1. As in Example 2, R0 plants were grown to maturity, selfed to produce R1 seed, and the edited junction sequences were characterized by PCR amplicon sequencing. The homozygous-edited, nuclease-null R1 plants were identified and were either crossed with wildtype plants of Inbred 2 to produce hybrid seed, or selfed to produce R2 seed.

TABLE 10

Additional deletions identified at R0 and confirmed by sequencing at R1

| R0 plant ID | Edit ID | Edit description | SEQ ID of edit junction | SEQ ID of predicted protein from edit junction |
|---|---|---|---|---|
| 92 | 6 | 931 bp deletion in exons 1 & 2 | SEQ ID NO: 55 | SEQ ID NO: 60 |
| 93 | 7 | 187 and 156 bp deletions in exon2 | SEQ ID NO: 56 | SEQ ID NO: 61 |
| 94 | 8 | 511 bp deletion in exons 1 & 2 | SEQ ID NO: 57 | SEQ ID NO: 62 |
| 95 | 9 | 4 bp deletion in exon2 | SEQ ID NO: 58 | SEQ ID NO: 63 |
| 96 | 10 | 12, 188, and 11 bp deletions in exon2 | SEQ ID NO: 59 | SEQ ID NO: 64 |

Example 7. Hybrid Controlled Environment Experiment of Additional Edited Plants R1 plants were first screened by PCR to identify nuclease-null and edit-positive plants. Sequencing of PCR products, as described in Example 2, was used to determine if the plants were either homozygous (HOM) or heterozygous (HET) for the edit. Wildtype (WT) plants were devoid of the edit. Hybrid $F_1$ seeds were produced from homozygous-edited R1 plants of Inbred 1 crossed to wildtype plants of Inbred 2. Hybrid control seeds were also produced from wildtype plants of Inbred 1 crossed to wildtype plants of Inbred 2 in the same nursery. R1 and wildtype plants from this nursery are described in Table 11.

TABLE 11

R1 and WT plants from nursery to produce hybrid seeds

| Plant ID | Edit ID | Inbred ID | Edit Zygosity | Female Parent Plant ID |
|---|---|---|---|---|
| 97 | 6 | 1 | HOMO | 92 |
| 98 | 7 | 1 | HOMO | 93 |
| 99 | 8 | 1 | HOMO | 94 |
| 100 | 9 | 1 | HOMO | 95 |
| 101 | 10 | 1 | HOMO | 96 |
| 102 | WT | 1 | WT | |
| 103 | WT | 2 | WT | |
| 104 | WT | 2 | WT | |
| 105 | WT | 2 | WT | |
| 106 | WT | 2 | WT | |
| 107 | WT | 2 | WT | |
| 108 | WT | 2 | WT | |

The five Zm.Br2 homozygous plants and the wildtype control plants from Table 11 were crossed with wildtype plants of Inbred 2, and from these crosses 12 heterozygous-edited hybrids or 12 wildtype control hybrids from each hybrid variety were planted in the greenhouse and grown to maturity. One plant from each of Edit IDs 7, 8, and 9 did not survive to maturity, and 7 seeds of Edit ID 10 did not germinate. The data for plant height (PHT) and ear height (EHT) at maturity for individual plants are shown in Table 12. Statistical results of plant height and ear height for plants of different Edit IDs are shown in Table 13. The average plant height for plants of Edit IDs 6, 8, and 10 was significantly shorter than wildtype at p=0.05. The average ear height for plants of Edit IDs 6 and 10 was also significantly shorter than wildtype at p=0.05.

TABLE 12

Heterozygous-edited F1 hybrid plants with plant and ear height at maturity.

| Plant ID | Edit ID | Edit Zygosity | Female Parent Plant ID | Male Parent Plant ID | Mature PHT (in inches) | Mature EHT (in inches) |
|---|---|---|---|---|---|---|
| 109 | 6 | HET | 103 | 97 | 95.0 | 48.4 |
| 110 | 6 | HET | 103 | 97 | 108.5 | 49.5 |
| 111 | 6 | HET | 103 | 97 | 105.0 | 57.6 |
| 112 | 6 | HET | 103 | 97 | 107.7 | 59.4 |
| 113 | 6 | HET | 103 | 97 | 100.2 | 49.6 |
| 114 | 6 | HET | 103 | 97 | 108.5 | 53.0 |

TABLE 12-continued

Heterozygous-edited F1 hybrid plants with plant and ear height at maturity.

| Plant ID | Edit ID | Edit Zygosity | Female Parent Plant ID | Male Parent Plant ID | Mature PHT (in inches) | Mature EHT (in inches) |
|---|---|---|---|---|---|---|
| 115 | 6 | HET | 103 | 97 | 105.9 | 49.4 |
| 116 | 6 | HET | 103 | 97 | 101.1 | 53.2 |
| 117 | 6 | HET | 103 | 97 | 103.4 | 51.5 |
| 118 | 6 | HET | 103 | 97 | 109.1 | 53.0 |
| 119 | 6 | HET | 103 | 97 | 99.9 | 51.8 |
| 120 | 6 | HET | 103 | 97 | 98.0 | 56.0 |
| 121 | 7 | HET | 104 | 98 | 109.3 | 55.4 |
| 122 | 7 | HET | 104 | 98 | 115.4 | 59.1 |
| 123 | 7 | HET | 104 | 98 | 114.8 | 56.4 |
| 124 | 7 | HET | 104 | 98 | 117.6 | 62.7 |
| 125 | 7 | HET | 104 | 98 | 119.4 | 63.0 |
| 126 | 7 | HET | 104 | 98 | 115.9 | 61.2 |
| 127 | 7 | HET | 104 | 98 | 122.5 | 65.3 |
| 128 | 7 | HET | 104 | 98 | 116.3 | 59.6 |
| 129 | 7 | HET | 104 | 98 | 113.3 | 55.7 |
| 130 | 7 | HET | 104 | 98 | 108.3 | 60.5 |
| 131 | 7 | HET | 104 | 98 | 105.0 | 59.4 |
| 132 | 8 | HET | 105 | 99 | 101.7 | 53.5 |
| 133 | 8 | HET | 105 | 99 | 109.7 | 60.4 |
| 134 | 8 | HET | 105 | 99 | 109.8 | 61.3 |
| 135 | 8 | HET | 105 | 99 | 114.5 | 59.7 |
| 136 | 8 | HET | 105 | 99 | 110.1 | 62.4 |
| 137 | 8 | HET | 105 | 99 | 111.4 | 62.6 |
| 138 | 8 | HET | 105 | 99 | 112.6 | 62.6 |
| 139 | 8 | HET | 105 | 99 | 110.6 | 61.4 |
| 140 | 8 | HET | 105 | 99 | 107.2 | 59.9 |
| 141 | 8 | HET | 105 | 99 | 104.0 | 60.4 |
| 142 | 8 | HET | 105 | 99 | 101.1 | 55.9 |
| 143 | 9 | HET | 106 | 100 | 115.0 | 58.5 |
| 144 | 9 | HET | 106 | 100 | 113.3 | 60.1 |
| 145 | 9 | HET | 106 | 100 | 116.9 | 61.1 |
| 146 | 9 | HET | 106 | 100 | 120.9 | 63.3 |
| 147 | 9 | HET | 106 | 100 | 118.2 | 61.8 |
| 148 | 9 | HET | 106 | 100 | 106.7 | 58.9 |
| 149 | 9 | HET | 106 | 100 | 116.8 | 62.1 |
| 150 | 9 | HET | 106 | 100 | 118.9 | 61.0 |
| 151 | 9 | HET | 106 | 100 | 117.6 | 61.9 |

TABLE 12-continued

Heterozygous-edited F1 hybrid plants with plant and ear height at maturity.

| Plant ID | Edit ID | Edit Zygosity | Female Parent Plant ID | Male Parent Plant ID | Mature PHT (in inches) | Mature EHT (in inches) |
|---|---|---|---|---|---|---|
| 152 | 9 | HET | 106 | 100 | 118.2 | 63.9 |
| 153 | 9 | HET | 106 | 100 | 105.1 | 60.9 |
| 154 | 10 | HET | 107 | 101 | 104.2 | 52.6 |
| 155 | 10 | HET | 107 | 101 | 109.9 | 56.1 |
| 156 | 10 | HET | 107 | 101 | 101.1 | 53.4 |
| 157 | 10 | HET | 107 | 101 | 100.5 | 56.1 |
| 158 | 10 | HET | 107 | 101 | 97.4 | 47.2 |
| 159 | WT | WT | 108 | 102 | 110.6 | 56.0 |
| 160 | WT | WT | 108 | 102 | 120.4 | 60.4 |
| 161 | WT | WT | 108 | 102 | 122.9 | 62.0 |
| 162 | WT | WT | 108 | 102 | 123.7 | 63.4 |
| 163 | WT | WT | 108 | 102 | 115.6 | 55.7 |
| 164 | WT | WT | 108 | 102 | 125.0 | 64.9 |
| 165 | WT | WT | 108 | 102 | 125.3 | 66.0 |
| 166 | WT | WT | 108 | 102 | 122.6 | 64.5 |
| 167 | WT | WT | 108 | 102 | 122.5 | 70.5 |
| 168 | WT | WT | 108 | 102 | 120.9 | 66.4 |
| 169 | WT | WT | 108 | 102 | 120.4 | 62.7 |
| 170 | WT | WT | 108 | 102 | 103.0 | 55.3 |

TABLE 13

Statistical analysis of plant and ear height data (in inches) for heterozygous-edited F1 plants in the controlled environment

| Edit ID | N | Average PHT | STDEV PHT | p value of PHT | Average EHT | STDEV EHT | p value of EHT |
|---|---|---|---|---|---|---|---|
| WT | 12 | 119.409 | 6.628 | | 62.316 | 4.729 | |
| 6 | 12 | 103.520 | 4.673 | 8.07E−07 | 52.697 | 3.452 | 1.01E−05 |
| 7 | 11 | 114.345 | 10.620 | 0.1805 | 59.846 | 3.158 | 0.1595 |
| 8 | 11 | 108.418 | 4.409 | 0.0001 | 60.000 | 2.862 | 0.1749 |
| 9 | 11 | 115.240 | 9.899 | 0.2448 | 61.238 | 1.659 | 0.4822 |
| 10 | 5 | 102.614 | 4.728 | 0.0001 | 53.079 | 3.646 | 0.0015 |

The invention claimed is:

1. A modified corn plant, plant part or plant cell comprising a mutant allele of an endogenous brachytic2 (br2) gene encoding a truncated Br2 protein, wherein the truncated Br2 protein encoded by the mutant allele of the endogenous brachytic2 (br2) gene comprises a first transmembrane segment that comprises an amino acid sequence having at least 95% sequence identity to the sequence of SEQ ID NO: 28 and a second transmembrane segment that comprises an amino acid sequence having at least 95% sequence identity to the sequence of SEQ ID NO: 29 and does not comprise a Walker A, Q-Loop, ABC Transport, Walker B, D-Loop, or H-Loop motif of a nucleotide binding domain, and wherein the truncated Br2 protein encoded by the mutant allele of the endogenous Zm.br2 gene disrupts the function of a wild-type Br2 protein expressed from an endogenous wild-type Zm.br2 locus, and wherein the mutant allele of the endogenous brachytic2 (br2) gene is dominant or semi-dominant for a shorter plant height and/or improved lodging resistance phenotype or trait relative to an unmodified control plant.

2. The modified corn plant, plant part or plant cell of claim 1, wherein:

a) the transmembrane domain of the truncated Br2 protein comprises three transmembrane segments, four transmembrane segments, five transmembrane segments, or six transmembrane segments of the first transmembrane domain;

b) the truncated Br2 protein comprises 3-6 of the first transmembrane domain of a wild-type Zm.Br2 protein or one or more of transmembrane segments 7-12 of a second transmembrane domain of a wild-type Zm.Br2 protein;

c) the truncated Br2 protein comprises a transmembrane domain that comprises amino acids 137-421 of SEQ ID NO: 3;

d) the truncated Br2 protein further comprises a transmembrane domain comprising:

a third transmembrane region that comprises the sequence of SEQ ID NO: 30 a fourth transmembrane region that comprises the sequence of SEQ ID NO:31, a fifth transmembrane region that comprises the sequence of SEQ ID NO: 32, or a sixth transmembrane region that comprises the sequence of SEQ ID NO: 33, or any combination thereof;

e) the truncated Br2 protein encoded by the mutant allele of the endogenous brachytic2 (br2) gene further comprises a N-terminal region;

f) the mutant allele of the endogenous Zm.br2 gene comprises a premature stop codon;

g) the mutant allele of the endogenous Zm.br2 gene is made using a mutagenesis or targeted editing technique;

h) the modified corn plant has a shorter plant height and/or an improved lodging resistance phenotype relative to an unmodified control plant;

i) the modified corn plant does not have any significant off-types in at least one female organ or ear;

j) the modified corn plant exhibits essentially no reproductive abnormality;

k) the modified corn plant, plant part or plant cell is homozygous for the mutant allele of the endogenous Zm.br2 gene; or l) the modified corn plant, plant part or plant cell is heterozygous for the mutant allele of the endogenous Zm.br2 gene.

3. The modified corn plant, plant part or plant cell of claim 2, wherein:

a) the transmembrane domain of the truncated Br2 protein comprises a polypeptide sequence that comprises the sequence of amino acids 137-197 of SEQ ID NO: 3, amino acids 137-283 of SEQ ID NO: 3, amino acids 137-307 of SEQ ID NO: 3, amino acids 137-392 of SEQ ID NO: 3, amino acids 137-421 of SEQ ID NO: 3, amino acids 180-283 of SEQ ID NO: 3, amino acids 180-307 of SEQ ID NO: 3, amino acids 180-392 of SEQ ID NO: 3, amino acids 180-421 of SEQ ID NO: 3, amino acids 264-307 of SEQ ID NO: 3, amino acids 264-392 of SEQ ID NO: 3, amino acids 264-421 of SEQ ID NO: 3, amino acids 285-392 of SEQ ID NO: 3, amino acids 285-421 of SEQ ID NO: 3, or amino acids 370-421 of SEQ ID NO: 3;

b) the premature stop codon is present in exon 2 or exon 3 of the mutant allele of the endogenous Zm.br2 gene; or c) the premature stop codon is present within a genomic sequence of the mutant allele of the endogenous Zm.br2 gene corresponding to nucleotides 1477-2717 or 1477-2609 of SEQ ID NO: 1, nucleotides 1591-2717 or 1591-2609 of SEQ ID NO: 1, nucleotides 1591-2717 or 1591-2609 of SEQ ID NO: 1, nucleotides 1992-2717 or 1992-2609 of SEQ ID NO: 1, nucleotides 2064-2717 or 2064-2609 of SEQ ID NO: 1, 2319-2717 or 2319-2609 of SEQ ID NO: 1, or nucleotides 2495-2717 or 2495-2609 of SEQ ID NO: 1.

4. The modified corn plant, plant part or plant cell of claim 3, wherein the truncated Br2 protein comprises a polypeptide sequence that comprises the sequence of amino acids 137-197, 137-283, 137-307, 137-392, or 137-421 of SEQ ID NO: 3.

5. The modified corn plant, plant part or plant cell of claim 2, wherein:

a) the mutant allele of the endogenous Zm.br2 gene comprises a deletion of most or all of the genomic sequence of the endogenous Zm.br2 gene encoding a nucleotide binding domain or a deletion of all genomic sequences of the endogenous Zm.br2 gene encoding nucleotide binding domain motifs of the nucleotide binding domain;

b) the mutant allele of the endogenous Zm.br2 gene comprises a deletion of (i) most or all of the genomic sequence of the endogenous Zm.br2 gene encoding a first nucleotide binding domain or all genomic sequences of the endogenous Zm.br2 gene encoding nucleotide binding domain motifs of the first nucleotide binding domain, and (ii) most or all of the genomic sequence of the endogenous Zm.br2 gene encoding a second nucleotide binding domain or all genomic sequences of the endogenous Zm.br2 gene encoding nucleotide binding domain motifs of the second nucleotide binding domain;

c) the mutant allele of the endogenous Zm.br2 gene further comprises a deletion of all or part of the one or more genomic sequences of the endogenous Zm.br2 gene encoding the second transmembrane domain, and/or the C-terminal region of the Zm.Br2 protein;

d) the mutant allele of the endogenous Zm.br2 gene comprises a deletion of all or part of exon 2, intron 2, exon 3, intron 3, exon 4, intron 4, and/or exon 5 of the endogenous Zm.br2 gene; or e) the truncated Br2 protein has an amino acid length within a range of 175 amino acids and 495 amino acids.

6. A method for producing a mutant allele of an endogenous brachytic2 (Zm.br2) gene, the method comprising:

(a) generating a double-stranded break (DSB) or nick in the endogenous Zm.br2 gene in a corn cell of an explant using a targeted editing technique; and (b) selecting a modified corn plant or plant part developed or regenerated from the cell of the explant comprising the mutant allele of the endogenous Zm.br2 gene, wherein the mutant allele of the endogenous brachytic2 (br2) gene encodes a truncated Br2 protein that comprises a first transmembrane segment that comprises an amino acid sequence having at least 95% sequence identity to the sequence of SEQ ID NO: 28 and a second transmembrane segment that comprises an amino acid sequence having at least 95% sequence identity to the sequence of SEQ ID NO: 29 and does not comprise a Walker A, Q-Loop, ABC Transport, Walker B, D-Loop, or H-Loop motif of a nucleotide binding domain, and wherein the truncated Br2 protein encoded by the mutant allele of the endogenous Zm.br2 gene disrupts the function of a wild-type Br2 protein expressed from an endogenous wild-type Zm.br2 locus, and wherein the mutant allele of the endogenous brachytic2 (br2) gene is dominant or semi-dominant for a shorter plant height and/or improved lodging resistance phenotype or trait relative to an unmodified control plant.

7. The method of claim 6, wherein:

a) the targeted editing technique comprises the use of at least one site-specific nuclease;

b) the mutant allele of the endogenous Zm.br2 gene comprises a premature stop codon;

c) the mutant allele of the endogenous Zm.br2 gene comprises a deletion of one or more nucleotides within the coding region of the endogenous Zm.br2 gene; or d) the target site for introducing the double-stranded break (DSB) or nick in the endogenous br2 gene in a corn cell is downstream of a genomic sequence encoding the first transmembrane segment and the second transmembrane segment of a Zm.Br2 protein encoded by the endogenous br2 gene and upstream of a genomic sequence encoding a first nucleotide binding domain or a Walker A motif of the first nucleotide binding domain of the Zm.Br2 protein.

8. The method of claim 7, wherein:

a) the at least one site-specific nuclease is selected from the group consisting of a zinc-finger nuclease, a meganuclease, an RNA-guided nuclease, a TALE-nuclease, a recombinase, a transposase, and any combination thereof; or b) the at least one site-specific nuclease is a RNA-guided nuclease selected from the group consisting of a Cas9 nuclease or a variant thereof and a Cpf1 nuclease or a variant thereof.

9. The method of claim 6, further comprising:

(c) regenerating or developing a corn plant or plant part from the corn cell.

10. The method of claim 6, wherein the selecting step (b) comprises selecting a modified corn plant having a shorter plant height and/or an improved lodging resistance phenotype or trait relative to an unmodified control plant.

11. A method for generating a corn plant comprising:

(a) fertilizing at least one female corn plant with pollen from a male corn plant, wherein said female corn plant or said male corn plant comprises a mutant allele of an endogenous brachytic2 (br2) gene; and (b) obtaining at least one plant part or seed comprising the mutant allele of the endogenous brachytic2 (br2) gene produced by said fertilizing step (a), wherein the mutant allele of the endogenous brachytic2 (br2) gene encodes a truncated Br2 protein that comprises a first transmembrane segment that comprises an amino acid sequence having at least 95% sequence identity to the sequence of SEQ ID NO: 28 and a second transmembrane segment that comprises an amino acid sequence having at least 95% sequence identity to the sequence of SEQ ID NO: 29 and does not comprise a Walker A, Q-Loop, ABC Transport, Walker B, D-Loop, or H-Loop motif of a nucleotide binding domain, and wherein the truncated Br2 protein encoded by the mutant allele of the endogenous Zm.br2 gene disrupts the function of a wild-type Br2 protein expressed from an endogenous wild-type Zm.br2 locus, and wherein the mutant allele of the endogenous brachytic2 (br2) gene is dominant or semi-dominant for a shorter plant height and/or improved lodging resistance phenotype or trait relative to an unmodified control plant.

12. The method of claim 11, wherein said method further comprises:

(c) growing or developing at least one progeny corn plant comprising the mutant allele from said at least one seed obtained in step (b).

13. The method of claim 12, wherein:

a) said at least one progeny corn plant is heterozygous for said mutant allele;

b) said at least one progeny corn plant has a shorter plant height and/or improved lodging resistance relative to a control plant that does not comprise said mutant allele; or c) said at least one progeny corn plant has a shorter plant height and/or improved lodging resistance relative to said male corn plant and/or said female corn plant.

14. The method of claim 11, wherein:

a) said female corn plant does not comprise said mutant allele;

b) said female corn plant is homozygous for said mutant allele;

c) said female corn plant is heterozygous for said mutant allele;

d) said male corn plant does not comprise said mutant allele;

e) said male corn plant is homozygous for said mutant allele;

f) said male corn plant is heterozygous for said mutant allele;

g) said female corn plant is an inbred corn plant or a hybrid corn plant;

h) said male corn plant is an inbred corn plant or a hybrid corn plant;

i) said female corn plant and/or said male corn plant is an elite corn plant;

j) said female corn plant and said male corn plant are grown in a greenhouse or growth chamber;

k) said female corn plant and said male corn plant are grown outdoors or in the field;

l) said female corn plant is a first inbred corn line or variety and said male corn plant is a second inbred corn line or variety, and wherein said first inbred corn line or variety and said second inbred corn line or variety are different and genetically distinct; or m) said female corn plant has been detasseled or is a cytoplasmically male sterile corn plant.

15. A method for producing a mutant allele of an endogenous brachytic2 (br2) locus or gene, the method comprising:

(a) generating at least a first double-stranded break (DSB) or nick at or near a first target site and a second DSB or nick at or near a second target site in the endogenous br2 locus or gene in a corn cell using a targeted editing technique; and (b) identifying at least one corn plant, plant part, plant seed or plant cell developed or regenerated from said corn cell comprising a deletion in the endogenous br2 locus or gene between the first target site and the second target site, wherein the mutant allele of the endogenous brachytic2 (br2) locus or gene encodes a truncated Br2 protein that comprises a first transmembrane segment that comprises an amino acid sequence having at least 95% sequence identity to the sequence of SEQ ID NO: 28 and a second transmembrane segment that comprises an amino acid sequence having at least 95% sequence identity to the sequence of SEQ ID NO: 29 and does not comprise a Walker A, Q-Loop, ABC Transport, Walker B, D-Loop, or H-Loop motif of a nucleotide binding domain, and wherein the truncated Br2 protein encoded by the mutant allele of the endogenous Zm.br2 gene disrupts the function of a wild-type Br2 protein expressed from an endogenous wild-type Zm.br2 locus, and wherein the mutant allele of the endogenous brachytic2 (br2) gene is dominant or semi-dominant for a shorter plant height and/or improved lodging resistance phenotype or trait relative to an unmodified control plant.

16. A method for producing a mutant allele of an endogenous brachytic2 (br2) locus or gene, the method comprising:

(a) generating a double-stranded break (DSB) or nick at or near a target site in the endogenous br2 locus or gene in a corn cell using a targeted editing technique; and (b) identifying at least one corn plant, plant part, plant seed or plant cell developed or regenerated from said corn cell comprising a premature stop codon in the coding sequence of the endogenous br2 locus or gene, wherein the premature stop codon in the coding sequence of the endogenous br2 locus or gene results in a truncated Br2 protein that comprises a first transmembrane segment that comprises an amino acid sequence having at least 95% sequence identity to the sequence of SEQ ID NO: 28 and a second transmembrane segment that comprises an amino acid sequence having at least 95% sequence identity to the sequence of SEQ ID NO: 29 and does not comprise a Walker A, Q-Loop, ABC Transport, Walker B, D-Loop, or H-Loop motif of a nucleotide binding domain, and wherein the truncated Br2 protein encoded by the mutant allele of the endogenous Zm.br2 gene disrupts the function of a wild-type Br2 protein expressed from an endogenous wild-type Zm.br2 locus, and wherein the mutant allele of the endogenous brachytic2 (br2) gene is dominant or semi-dominant for a shorter plant height and/or improved lodging resistance phenotype or trait relative to an unmodified control plant.

17. The method of claim 16, wherein the method further comprises providing to the at least one corn cell a donor template comprising the premature stop codon.

18. The method of claim 17, wherein the donor template further comprises at least one homology arm to direct the integration of a mutation at or near the target site in the endogenous br2 locus.

19. The method of claim 15, wherein the method further comprises developing or regenerating at least one corn plant or plant part from the at least one corn cell identified in step (b).

20. The method of claim 16, wherein the method further comprises developing or regenerating at least one corn plant or plant part from the at least one corn cell identified in step (b).

* * * * *

SEQUENCE LISTING

```
Sequence total quantity: 64
SEQ ID NO: 1           moltype = DNA  length = 8667
FEATURE                Location/Qualifiers
source                 1..8667
                       mol_type = genomic DNA
                       organism = Zea mays
SEQUENCE: 1
aataagttga gtcggggtag atctcaaggc tacataaaat agttttttttt ctagaatgga  60
tgcatttgtt ttaagagaaa aatgatgcac ttggaatgca tcaagcgaag ggatgcaaga  120
atgttggaaa aacacatgaa cccgtatcgc gagatgctta tttagccatt cttttatcac  180
agtggatgca tatgcaacaa aaccaaaaca gatggttagc gagtgacagt atatagagat  240
ctaaagattc cgacacttca tcggtaaaaa aagcagcatt aaccgagtga atggaagaaa  300
aacgaatttc tcatattaca caacaggttt tcttaaaaaa aaaaacgtta cctcggtatt  360
tatattaaga agagactaaa atatggtccc gtcgagaaaa tttctaaaca ctagtcttca  420
tcactagtga gccgtcacca tctagtttgc aacggtccag tcagagtgca ggacataact  480
caggactcaa gagcagacgg agcacggtga gagaattttt tttaatcaag cctaaaattc  540
acctccggac aaattgaacc tggaacgggt gctactcata aatattaacc atgagacctt  600
ttcgccgcag caggttttct atcggcagtt agattttagt gacgatgaaa atgatagaac  660
gcaacgtgcc gcatgcatcc attcccattc gttttccaca gtacatgtag gagtactgtg  720
caagtagggt ccgtacattc agtctctctc accagttgga ctcttctact gctacaaaga  780
catgagctgc ctggaatggg aaccggagga gcgagcgagc ctgacggtct cacacacaca  840
cagtcacact cccaagccaa ttattataag aggcgagatg agcaactcca gctcttaacc  900
aatccactcc tcctccctct ccacctcctc tgctttgctc tgccactctg ctgaggtggg  960
gggcagagga gctccccctc cctcctctcc cctcctcgcc atgtctagca gcgacccgga  1020
ggagatcagg gcgcgcgtcg tcgttctcgg ttcgccccat gccgacggcg gcgacgagtg  1080
ggcccggccc gagctcgagg ccttccatct gccgtctccc gcccaccagc ctcctggctt  1140
cctagccggg caaccggaag cagcagagca acccacgctc cctgctcctg ctggccgcag  1200
cagcagcagc agcaacacgc ctactacatc tgccggtggc ggcgctgctc ctcctcctcc  1260
ttcttcgcct ccccctccgc cggcttctct ggagaccgag cagccgccca atgccaggcc  1320
```

-continued

```
agcctccgcc ggcgccaatg acagcaagaa gcccaccccg cccgccgccc tgcgcgacct  1380
cttccgcttc gccgacggcc tcgactgcgc gctcatgctc atcggcaccc tcggcgcgct  1440
cgtccacggc tgctcgctcc ccgtcttcct ccgcttcttc gccgacctcg tcgactcctt  1500
cggctcccac gccgacgacc cggacaccat ggtccgcctc gtcgtcaagt acgccttcta  1560
cttcctcgtc gtcggagcgg caatctgggc atcctcgtgg gcaggtacgc tatccctcct  1620
cctcctgccg ccccagcttg tgtgcgtcgc gaattggcgg tcaatttgga ttggatgaca  1680
aatcacgtcg gtcagccaat cgccgtggct acaaacgaga tgttcaaatc gttcgccccg  1740
ctcgcagaga tctcttgctg gatgtggacc ggcgagcggc agtcgacgcg gatgcggatc  1800
cggtacctgg acgcggcgct gcggcaggac gtgtccttct tcgacaccga cgtgcgggcc  1860
tcggacgtga tctacgccat caacgcggac gcagtggtgg tgcaggacgc catcagcgag  1920
aagctgggca acctcatcca ctacatggcc accttcgtgg ccggcttcgt cgtggggttc  1980
acggccgcgt ggcagctggc gctggtcacg ctggccgtgg tgccgctcat cgccgtcatc  2040
ggcgggctga gcgccgccgc gctcgccaag ctctcgtccc gcagccagga cgcgctctcc  2100
ggcgccagcg gcatcgcgga gcaggcgctc gcgcagatac ggatcgtgca ggcgttcgtc  2160
ggcgaggagc gcgagatgcg ggcctactcg gcggcgctgg ccgtggcgca gaggatcggc  2220
taccgcagcg gcttcgccaa gggtctcggc ctcggcggca cctacttcac cgtcttctgc  2280
tgctacgggc tcctgctctg gtacggcggc cacctcgtgc gcgcccagca caccaacggc  2340
gggctcgcca tcgccaccat gttctccgtc atgatcggcg gactgtaagg cccaccacac  2400
cactctctcc ttctcctgct cctcggcccg cccgtcgtca ttgctgctga cggtgtctgt  2460
ggatcgcgtg cagggccctc gggcagtcgg cgccgagcat ggccgcgttc gccaaggcgc  2520
gtgtggcggc tgccaagatc ttccgcatca tcgaccacag gccgggcatc tcctcgcgcg  2580
acggcgcgga gccagagtcg gtgacggggc gggtggagat gcggggcgtg gacttcgcgt  2640
acccgtcgcg gccggacgtc cccatcctgc gcggcttctc gctgagcgtg cccgccggga  2700
agaccatcgc gctggtgggc agctccggct ccgggaagag cacggtggtt tcgctcatcg  2760
agaggttcta cgaccccagc gcaggtatac tacctagtac tgttactact tttagcgcat  2820
taatctgagg atgtccagtt cgcttgcttg ccaatcgcca ttgccatcgc aacaatacat  2880
tgccaactgc cattgctggg tagactagta ctgtagtaca gtagcagtta gaagaagcct  2940
ccactgtaca ttgcattgcc aaacaaaagt gaattgtgca gtaactctgt accaccacat  3000
tgacatggaa atgaagtgaa tgcttggagc atgcagagct ggccggcctc atgggctgct  3060
gctacctgct agctagccaa ccagaaccag ccatcctctt tcttgctttt ctttttactt  3120
tctttggtcg tggctgtttg tggtcataca tacattcacg cgcagagcag aagagctagc  3180
taagctaggt gggtgtgcct gcaacgcggg acaaagaaaa ctatttgttg cctggcaaga  3240
tgctactgtt gcctagcaca tgcctgccat tgaccgactg ctcagtgaga agtggttcag  3300
ttgtgctgtt gacagtatag atagatatat atatagtagc cctgtatatt ttctttttca  3360
gacaagaaaa aaagaagaac gagatgaagt ctgcaattcg gttttggcag ggcaaatcct  3420
gctggacggg cacgacctca ggtcgctgaa gctgcgatgg ctgcggcggc agatcgggct  3480
ggtgagccag gagccggcgc tgttcgcgac gagcatcagg gagaacctgc tgctggggcg  3540
ggacagccag agcgcgacgc tggcggagat ggaggaggcg gccagggtgg ccaacgccca  3600
ctccttcatc atcaaactcc ccgacggcta cgacacgcag gtccgtcccg tatagctagc  3660
tcactagctg cactgccact tctctcgctt gctccccacc gttgctgcct gttgctctcc  3720
aatccacttg tcggtgtctg gaccacacgt gcctgcttgc ctagctgctc cacatctgct  3780
ttccctgtcc aaccttatgc aactcactca gtcactctat actatatcaa atacatttct  3840
agagtttaaa gcttatctta gaataaatgc atctttagct acgagacaac ctaacttcag  3900
ttgttgttgt ttttttact ttctctcttc tcaaaaatac attgattacg tctttacagc  3960
gatcttttta ttccaaacct aaaaatgcat gcactcactc taaaagcgca aagggagcat  4020
ctttttcccc catcatctgc acgcagcctt ttcttttcct catgtcacga gggactgaag  4080
gtgtgtatgc agcgtcaagt catccatccg ttccactcca ctcactcatg cgtcgcgcac  4140
tctgcgctcg tgcctgcccg gggctaaagc tttagtagct agcctcagat cagatactgt  4200
tcgtgtttgt taggccgcgg cagcggcaca tgagctcatg acagccggca gcaccaccac  4260
caacaccatg gaagaggggt cggggtccat cacatagaca tagatgcctg ttgtagacta  4320
gggacgggag ggcaattgtt aggcgcctgt tgccatcgca tttgctgctg tgggttgcca  4380
acaagtaaca tgccaggatg ctttgctatc acgcacagga caggaggaga ggtccttttt  4440
ctcgacacaa gatctactaa actagcactt gctgatgagt gcataggatg aatggatgat  4500
gaacatctag agtgagagag agaaaatatg ttaataataa taaagagtag taatagtagt  4560
agtaggatta agaatcaacc tggggtacgt aggaagaggt acaatcccta ggaatctaga  4620
gtatgagaag tatgggagga gttgtgagtg aaacggaaca aattccgagt tggtattttg  4680
tcgggaatgt caagttgatt tttgatccta gtgcaagcaa gaattatcaa tcactcagac  4740
tcagcctgtc tgtgtctgtc caccccagct cttgctactc tacttactac tgtgctacta  4800
gtggtagggt aggtatcttc cataaactgt tattataaac tgtcatctga gaaagagagc  4860
cagtcaaacc catgctgctg cttattttta atcactgtca aatggcaggc aggcaggcag  4920
tctggttagt taataacatc tgggaagggt ttaatcaaac caaatcaaat catacgaaat  4980
ctagaggcca catgggatgg ggccatatgt actgtactag cataagtagc ggctagattt  5040
tattagaaca cggactcaca ctcccataac tataactgac tttgatcatg attccttgcc  5100
aagcaatgct cgcatgccca tgcatgcatc atccctggtc aaactcaaac actctccacc  5160
gtcagggaat aagacttatt attttattaa caattccatt tttatttatt aattacggct  5220
ggacgaggag tactagttta tttgatgaga gacatggcag tccaagtcaa actcgtttgt  5280
ctgaccatgg cggtgatggc cggttgcagg ttggggagcg cggcctgcag ctctccggtg  5340
ggcagaagca gcgcatcgcc atcgcccgcg ccatgctcaa gaaccccgcc atcctgctgc  5400
tggacgaggc caccagcgcg ctggactccg agtctgagaa gctcgtgcag gaggcgctgg  5460
accgcttcat gatcgggcgc accaccctgg tgatcgcgca caggctgtcc accatccgca  5520
aggccgacgt ggtggccgtg ctgcagggcg gcgccgtctc cgagatgggc gcgcacgacg  5580
agctgatggc caagggcgag aacggcacct acgccaagct catccgcatg caggagcagg  5640
cgcacgaggc ggcgctcgtc aacgcccgcc gcagcagcgc caggccctcc agcgcccgca  5700
actccgtcag ctcgcccatc atgacgcgca actcctccta cggccgctcc ccctactccc  5760
gccgcctctc cgacttctcc acctccgact tcaccctctc catccacgac ccgcaccacc  5820
accaccggac catggcggac aagcagctgg cgttccgcgc cggcgccagc tccttcctgc  5880
gcctcgccag gatgaactcg cccgagtggg cctacgcgct cgccggctcc atcggctcca  5940
tggtctgcgg ctccttcagc gccatcttcg cctacatcct cagcgccgtg ctcagcgtct  6000
actacgcgcc ggacccgcgg tacatgaagc gcgagatcgc aaaatactgc tacctgctca  6060
```

```
tcggcatgtc ctccgcggcg ctgctgttca acacggtgca gcacgtgttc tgggacacgg  6120
tgggcgagaa cctgaccaag cgggtgcgcg agaagatgtt cgccgccgtg ctccgcaacg  6180
agatcgcctg gttcgacgcg gacgagaacg ccagcgcgcg cgtggccgcc aggctagcgc  6240
tggacgccca gaacgtgcgc tccgccatcg gggaccgcat ctccgtcatc gtccagaact  6300
cggcgctgat gctggtggcc tgcaccgcgg ggttcgtcct ccagtggcgc ctcgcgctcg  6360
tgctcctcgc cgtgttcccg ctcgtcgtgg gcgccaccgt gctgcagaag atgttcatga  6420
agggcttctc gggggacctg gaggccgcgc acgccagggc gacgcagatc gcgggcgagg  6480
ccgtggccaa cctgcgcacc gtggccgcgt tcaacgcgga gcgcaagatc acggggctgt  6540
tcgaggccaa cctgcgcggc ccgctccggc gctgcttctg gaaggggcag atcgccggca  6600
gcggctacgg cgtggcgcag ttcctgctgt acgcgtccta cgcgctgggg ctgtggtacg  6660
cggcgtggct ggtgaagcac ggcgtgtccg acttctcgcg caccatccgc gtgttcatgg  6720
tgctgatggt gtccgcgaac ggcgccgccg agacgctgac gctggcgccg gacttcatca  6780
agggcgggcg cgcgatgcgg tcggtgttcg agacgatcga ccgcaagacg gaggtggagc  6840
ccgacgacgt ggacgcggcg ccggtgccgg agcggccgag gggcgaggtg gagctgaagc  6900
acgtggactt ctcgtacccg tcgcggccgg acatccaggt gttccgcgac ctgagcctcc  6960
gtgcgcgggc cgggaagacg ctggcgctgg tggggccgag cgggtgcggc aagagctcgg  7020
tgctggcgct ggtgcagcgg ttctacgagc ccacgtccgg gcgcgtgctc ctggacggca  7080
aggacgtgcg caagtacaac ctgcgggcgc tgcggcgcgt ggtggcggtg gtgccgcagg  7140
agccgttcct gttcgcggcg agcatccacg agaacatcgc gtacgggcgc gagggcgcga  7200
cggaggcgga ggtggtggag gcggcggcgc aggcgaacgc gcaccggttc atcgcggcgc  7260
tgccggaggg gtaccggacg caggtgggcg agcgcggggt gcagctgtcg ggagggcagc  7320
ggcagcggat cgcgatcgcg cgcgcgctgg tgaagcaggc ggccatcgtg ctgctggacg  7380
aggcgaccag cgcgctggac gccgagtcgg agcggtgcgt gcaggaggcg ctggagcgcg  7440
cggggtccgg gcgcaccacc atcgtggtgg cgcaccggct ggccacggtg cgcggcgcgc  7500
acaccatcgc ggtcatcgac gacggcaagg tggcggagca ggggtcgcac tcgcacctgc  7560
tcaagcacca tcccgacggg tgctacgcgc ggatgctgca gctgcagcgg ctgacgggcg  7620
cggcggccgg gcccgggccg tcgacctcgt gcaacggggc cgcgtaggac ggaatggatg  7680
gatggatggg tttggttcct cgagagattg atgggtgagg aagctgaagc tccggatcaa  7740
atggtggtac tccatgatcg caacaatgag gggaaaaaaa gaaaggagaa aatacggtgg  7800
ttcatatgat tgtacaattt gacgatctgt ttgagtcggg gttttaggat gatgtaaacc  7860
ttcactcgcc tttttttac tcttgtttct catccgcatc agtatcatct atctacatac  7920
agtgtcagag atgggaactg atccgcatca tcatctacct cccaaggcac cccagattgt  7980
attaatgtac ttagttagcc tgttttatat atacttataa gtaccaaata gcagaatttt  8040
actccttatc tgcagtagca cgaaagaaga aacggcaagc tacacctatc tctggaagca  8100
aaagaatctc cccattctct ctcttcctac gaggacaccc catccttttc agacagacag  8160
acagacggac caaactgcac cacccaagaa ccgatcgaga gcagaggtag cattctctgc  8220
actgtagagt gtagaccata ctacgctgct ctcgagacat gatcccggga atatctaccg  8280
aattgtttgt cagtggcata gccgcatagc tctcagctgc ctaatgaatt gtttggtgcc  8340
aaccgcgctg caggcttgca gacgacccgg gaagggtcag ggattgcaca actactagca  8400
tcagtggaga gcgaaaggcc agaacggcag gcttgcagga aaacagggac cgtgagtttg  8460
acctggcctt ggggtgggga gtcagtcagt cacatgcgat gcgatgcagt ggaggaaccc  8520
atcttccaac gcacgcggca cgattgattt cagggttgct ttcgccgctg ccaatccacc  8580
gatccctgga cactggtgcg ttccttcgtc gcacatgacg gtgcgtcgcc ccaaccgcac  8640
aggactggga gaagggacgg attgggg                                     8667

SEQ ID NO: 2            moltype = DNA  length = 4140
FEATURE                 Location/Qualifiers
source                  1..4140
                        mol_type = genomic DNA
                        organism = Zea mays
SEQUENCE: 2
atgtctagca gcgacccgga ggagatcagg gcgcgcgtcg tcgttctcgg ttcgccccat  60
gccgacggcg gcgacgagtg ggcccggccc gagctcgagg ccttccatct gccgtctccc  120
gcccaccagc ctcctggctt cctagccggg caaccggaag cagcagagca acccacgctc  180
cctgctcctg ctggccgcag cagcagcagc agcaacacgc ctactacatc tgccggtggc  240
ggcgctgctc ctcctcctcc ttcttcgcct ccccctccgc cggcttctct ggagaccgag  300
cagccgccca atgccaggcc agcctccgcc ggcgccaatg acagcaagaa gcccaccccg  360
cccgccgccc tgcgcgacct cttccgcttc gccgacggcc tcgactgcgc gctcatgctc  420
atcggcaccc tcggcgcgct cgtccacggc tgctcgctcc ccgtcttcct ccgcttcttc  480
gccgacctcg tcgactcctt cggctcccac gccgacgacc cggacaccat ggtccgcctc  540
gtcgtcaagt acgccttcta cttcctcgtc gtcggagcgg caatctgggc atcctcgtgg  600
gcagagatct cttgctggat gtggaccggc gagcggcagt cgacgcggat gcggatccgg  660
tacctggacg cggcgctgcg gcaggacgtg tccttcttcg acaccgacgt gcgggcctcg  720
gacgtgatct acgccatcaa cgcggacgca gtggtggtgc aggacgccat cagcgagaag  780
ctgggcaacc tcatccacta catggccacc ttcgtggccg gcttcgtcgt ggggttcacg  840
gccgcgtggc agctggcgct ggtcacgctg gccgtggtgc cgctcatcgc cgtcatcggc  900
gggctgagcg ccgccgcgct cgccaagctc tcgtcccgca gccaggacgc gctctccggc  960
gccagcggca tcgcggagca ggcgctcgcg cagatacgga tcgtgcaggc gttcgtcggc  1020
gaggagcgcg agatgcgggc ctactcggcg gcgctggccg tggcgcagag gatcggctac  1080
cgcagcggct tcgccaaggg tctcggcctc ggcggcacct acttcaccgt cttctgctgc  1140
tacgggctcc tgctctggta cggcggccac ctcgtgcgcg cccagcacac caacggcggg  1200
ctcgccatcg ccaccatgtt ctccgtcatg atcggcggac tggccctcgg gcagtcggcg  1260
ccgagcatgg ccgcgttcgc caaggcgcgt gtggcggctg ccaagatctt ccgcatcatc  1320
gaccacaggc cgggcatctc ctcgcgcgac ggcgcggagc cagagtcggt gacggggcgg  1380
gtggagatgc ggggcgtgga cttcgcgtac ccgtcgcggc cggacgtccc catcctgcgc  1440
ggcttctcgc tgagcgtgcc cgccgggaag accatcgcgc tggtgggcag ctccggctcc  1500
gggaagagca cggtggtttc gctcatcgag aggttctacg accccagcgc agggcaaatc  1560
ctgctggacg ggcacgacct caggtcgctg aagctgcgat ggctgcggcg gcagatcggg  1620
ctggtgagcc aggagccggc gctgttcgcg acgagcatca gggagaacct gctgctgggg  1680
```

```
cgggacagcc agagcgcgac gctggcggag atggaggagg cggccagggt ggccaacgcc  1740
cactccttca tcatcaaact ccccgacggc tacgacacgc aggttgggga gcgcggcctg  1800
cagctctccg gtgggcagaa gcagcgcatc gccatcgccc gcgccatgct caagaacccc  1860
gccatcctgc tgctggacga ggccaccagc gcgctggact ccgagtctga gaagctcgtg  1920
caggaggcgc tggaccgctt catgatcggg cgcaccaccc tggtgatcgc gcacaggctg  1980
tccaccatcc gcaaggccga cgtggtggcc gtgctgcagg gcggcgccgt ctccgagatg  2040
ggcgcgcacg acgagctgat ggccaagggc gagaacggca cctacgccaa gctcatccgc  2100
atgcaggagc aggcgcacga ggcggcgctc gtcaacgccc gccgcagcag cgccaggccc  2160
tccagcgccc gcaactccgt cagctcgccc atcatgacgc gcaactcctc ctacggccgc  2220
tccccctact cccgccgcct ctccgacttc tccacctccg acttcaccct ctccatccac  2280
gacccgcacc accaccaccg gaccatggcg gacaagcagc tggcgttccg cgccggcgcc  2340
agctccttcc tgcgcctcgc caggatgaac tcgcccgagt gggcctacgc gctcgccggc  2400
tccatcggct ccatggtctg cggctccttc agcgccatct tcgcctacat cctcagcgcc  2460
gtgctcagcg tctactacgc gccggacccg cggtacatga agcgcgagat cgcaaaatac  2520
tgctacctgc tcatcggcat gtcctccgcg gcgctgctgt tcaacacggt gcagcacgtg  2580
ttctgggaca cggtgggcga gaacctgacc aagcgggtgc gcgagaagat gttcgccgcc  2640
gtgctccgca acgagatcgc ctggttcgac gcggacgaga acgccagcgc gcgcgtggcc  2700
gccaggctag cgctggacgc ccagaacgtg cgctccgcca tcggggaccg catctccgtc  2760
atcgtccaga actcggcgct gatgctggtg gcctgcaccg cggggttcgt cctccagtgg  2820
cgcctcgcgc tcgtgctcct cgccgtgttc ccgctcgtcg tgggcgccac cgtgctgcag  2880
aagatgttca tgaagggctt ctcgggggac ctggaggccg cgcacgccag ggcgacgcag  2940
atcgcgggcg aggccgtggc caacctgcgc accgtggccg cgttcaacgc ggagcgcaag  3000
atcacggggc tgttcgaggc caacctgcgc ggcccgctcc ggcgctgctt ctggaagggg  3060
cagatcgccg gcagcggcta cggcgtggcg cagttcctgc tgtacgcgtc ctacgcgctg  3120
gggctgtggt acgcggcgtg gctggtgaag cacggcgtgt ccgacttctc gcgcaccatc  3180
cgcgtgttca tggtgctgat ggtgtccgcg aacggcgccg ccgagacgct gacgctggcg  3240
ccggacttca tcaagggcgg gcgcgcgatg cggtcggtgt tcgagacgat cgaccgcaag  3300
acggaggtgg agcccgacga cgtggacgcg gcgccggtgc cggagcggcc gaggggcgag  3360
gtggagctga agcacgtgga cttctcgtac ccgtcgcggc cggacatcca ggtgttccgc  3420
gacctgagcc tccgtgcgcg ggccgggaag acgctggcgc tggtggggcc gagcgggtgc  3480
ggcaagagct cggtgctggc gctggtgcag cggttctacg agcccacgtc cgggcgcgtg  3540
ctcctggacg gcaaggacgt gcgcaagtac aacctgcggg cgctgcggcg cgtggtggcg  3600
gtggtgccgc aggagccgtt cctgttcgcg gcgagcatcc acgagaacat cgcgtacggg  3660
cgcgagggcg cgacggaggc ggaggtggtg gaggcggcgg cgcaggcgaa cgcgcaccgg  3720
ttcatcgcgg cgctgccgga ggggtaccgg acgcaggtgg gcgagcgcgg ggtgcagctg  3780
tcgggagggc agcggcagcg gatcgcgatc gcgcgcgcgc tggtgaagca ggcggccatc  3840
gtgctgctgg acgaggcgac cagcgcgctg gacgccgagt cggagcggtg cgtgcaggag  3900
gcgctggagc gcgcggggtc cggcgcgacc accatcgtgg tggcgcaccg gctggccacg  3960
gtgcgcggcg cgcacaccat cgcggtcatc gacgacggca aggtggcgga gcaggggtcg  4020
cactcgcacc tgctcaagca ccatcccgac gggtgctacg cgcggatgct gcagctgcag  4080
cggctgacgg gcgcggcggc cgggcccggg ccgtcgacct cgtgcaacgg ggccgcgtag  4140
```

```
SEQ ID NO: 3            moltype = AA  length = 1379
FEATURE                 Location/Qualifiers
source                  1..1379
                        mol_type = protein
                        organism = Zea mays
SEQUENCE: 3
MSSSDPEEIR ARVVVLGSPH ADGGDEWARP ELEAFHLPSP AHQPPGFLAG QPEAAEQPTL  60
PAPAGRSSSS SNTPTTSAGG GAAPPPPSSP PPPPASLETE QPPNARPASA GANDSKKPTP  120
PAALRDLFRF ADGLDCALML IGTLGALVHG CSLPVFLRFF ADLVDSFGSH ADDPDTMVRL  180
VVKYAFYFLV VGAAIWASSW AEISCWMWTG ERQSTRMRIR YLDAALRQDV SFFDTDVRAS  240
DVIYAINADA VVVQDAISEK LGNLIHYMAT FVAGFVVGFT AAWQLALVTL AVVPLIAVIG  300
GLSAAALAKL SSRSQDALSG ASGIAEQALA QIRIVQAFVG EEREMRAYSA ALAVAQRIGY  360
RSGFAKGLGL GGTYFTVFCC YGLLLWYGGH LVRAQHTNGG LAIATMFSVM IGGLALGQSA  420
PSMAAFAKAR VAAAKIFRII DHRPGISSRD GAEPESVTGR VEMRGVDFAY PSRPDVPILR  480
GFSLSVPAGK TIALVGSSGS GKSTVVSLIE RFYDPSAGQI LLDGHDLRSL KLRWLRRQIG  540
LVSQEPALFA TSIRENLLLG RDSQSATLAE MEEAARVANA HSFIIKLPDG YDTQVGERGL  600
QLSGGQKQRI AIARAMLKNP AILLLDEATS ALDSESEKLV QEALDRFMIG RTTLVIAHRL  660
STIRKADVVA VLQGGAVSEM GAHDELMAKG ENGTYAKLIR MQEQAHEAAL VNARRSSARP  720
SSARNSVSSP IMTRNSSYGR SPYSRRLSDF STSDFTLSIH DPHHHHRTMA DKQLAFRAGA  780
SSFLRLARMN SPEWAYALAG SIGSMVCGSF SAIFAYILSA VLSVYYAPDP RYMKREIAKY  840
CYLLIGMSSA ALLFNTVQHV FWDTVGENLT KRVREKMFAA VLRNEIAWFD ADENASARVA  900
ARLALDAQNV RSAIGDRISV IVQNSALMLV ACTAGFVLQW RLALVLLAVF PLVVGATVLQ  960
KMFMKGFSGD LEAAHARATQ IAGEAVANLR TVAAFNAERK ITGLFEANLR GPLRRCFWKG  1020
QIAGSGYGVA QFLLYASYAL GLWYAAWLVK HGVSDFSRTI RVFMVLMVSA NGAAETLTLA  1080
PDFIKGGRAM RSVFETIDRK TEVEPDDVDA APVPERPRGE VELKHVDFSY PSRPDIQVFR  1140
DLSLRARAGK TLALVGPSGC GKSSVLALVQ RFYEPTSGRV LLDGKDVRKY NLRALRRVVA  1200
VVPQEPFLFA ASIHENIAYG REGATEAEVV EAAAQANAHR FIAALPEGYR TQVGERGVQL  1260
SGGQRQRIAI ARALVKQAAI VLLDEATSAL DAESERCVQE ALERAGSGRT TIVVAHRLAT  1320
VRGAHTIAVI DDGKVAEQGS HSHLLKHHPD GCYARMLQLQ RLTGAAAGPG PSTSCNGAA   1379
```

```
SEQ ID NO: 4            moltype = DNA  length = 80
FEATURE                 Location/Qualifiers
source                  1..80
                        mol_type = other DNA
                        note = editing junction sequence
                        organism = synthetic construct
```

```
SEQUENCE: 4
acagtggatg catatgcaac aaaaccaaaa cagatggtta tggacactgg tgcgttcctt  60
cgtcgcacat gacggtgcgt                                              80

SEQ ID NO: 5            moltype = DNA  length = 83
FEATURE                 Location/Qualifiers
source                  1..83
                        mol_type = other DNA
                        note = editing junction sequence
                        organism = synthetic construct
SEQUENCE: 5
gtggatgcat atgcaacaaa accaaaacag atggttagcg gatcctggac actggtgcgt  60
tccttcgtcg cacatgacgg tgc                                          83

SEQ ID NO: 6            moltype = DNA  length = 80
FEATURE                 Location/Qualifiers
source                  1..80
                        mol_type = other DNA
                        note = editing junction sequence
                        organism = synthetic construct
SEQUENCE: 6
gcccaccagc ctcctggctt cctagccggg caaccggaag agcaacccac gctccctgct  60
cctgctggcc gcagcagcag                                              80

SEQ ID NO: 7            moltype = DNA  length = 80
FEATURE                 Location/Qualifiers
source                  1..80
                        mol_type = other DNA
                        note = editing junction sequence
                        organism = synthetic construct
SEQUENCE: 7
agagatctct tgctggatgt ggaccggcga gcggcagtcg ctccttctcc tgctcctcgg  60
cccgcccgtc gtcattgctg                                              80

SEQ ID NO: 8            moltype = DNA  length = 80
FEATURE                 Location/Qualifiers
source                  1..80
                        mol_type = other DNA
                        note = editing junction sequence
                        organism = synthetic construct
SEQUENCE: 8
agagatctct tgctggatgt ggaccggcga gcggcagtcg ctgctctggt acggcggcca  60
cctcgtgcgc gcccagcaca                                              80

SEQ ID NO: 9            moltype = DNA  length = 2008
FEATURE                 Location/Qualifiers
source                  1..2008
                        mol_type = genomic DNA
                        organism = Zea mays
SEQUENCE: 9
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttg caaatagctt gacctatata  300
atacttcatc cattttatta gtacatccat ttaggattta gggttgatgg tttctataga  360
ctaattttta gtacatccat tttattcttt ttagtctcta aatttttaa aactaaaact  420
ctattttagt tttttattta ataatttaga tataaaatga aataaaataa attgactaca  480
aataaaacaa atacccttta agaaataaaa aaactaagca aacattttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
```

```
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtc                                     2008

SEQ ID NO: 10          moltype = DNA  length = 3681
FEATURE                Location/Qualifiers
source                 1..3681
                       mol_type = genomic DNA
                       note = Lachnospiraceae bacterium ND2006
                       organism = unidentified
SEQUENCE: 10
tcgaagctcg agaagttcac caactgctac tcgctgagca agacgctgcg gttcaaggcg  60
atccccgtcg ggaagaccca ggagaacatc gacaacaagc ggctcctggt cgaggacgag  120
aagcgcgccg aggactacaa gggcgtcaag aagctgctgg accggtacta cctctccttc  180
atcaacgacg tcctgcactc gatcaagctc aagaacctga acaactacat ctcgctgttc  240
cgcaagaaga cacggaccga gaaggagaac aaggagctcg agaacctcga gatcaacctg  300
cgcaaggaga tcgcgaaggc gttcaagggc aacgaggggt acaagagcct gttcaagaaa  360
gacatcatcg agaccatcct gccggagttc ctggacgaca aggacgagat cgcgctggtg  420
aactcgttca acgggttcac cacggccttc accgggtttt tcgacaaccg ggagaacatg  480
ttcagcgagg aggccaagtc gaccagcatc gccttccggt gcatcaacga gaacctcacc  540
cgctacatca gcaacatgga catcttcgag aaggtggacg ccatcttcga caagcacgag  600
gtccaggaga tcaaggaaaa gatcctgaac tcggactacg acgtggaaga cttctttgag  660
ggcgagttct tcaacttcgt cctcacccag gagggcatcg acgtctacaa cgccatcatc  720
ggcggcttcg tgacggagag cggcgagaag atcaagggcc tcaacgagta catcaacctc  780
tacaaccaga agactaagca gaagctcccg aagttcaagc cgctgtacaa gcaagtcctg  840
agcgaccggg agtccctctc gttctacggc gagggctaca cgagcgacga ggaggtgctg  900
gaggtgttcc gcaacacgct gaacaagaac agcgagatct tcagctcgat caagaaactc  960
gagaagctgt tcaagaactt cgacgagtac agcagcgccg gcatcttcgt caagaacggg  1020
cccgcgatca gcaccatcag caaggacatc ttcggggagt ggaacgtgat ccgcgacaag  1080
tggaacgccg agtacgacga catccacctc aagaaaaagg cggtggtcac ggagaagtac  1140
gaggacgacc gccggaagtc cttcaagaaa atcgggagct tcagcctcga gcagctccag  1200
gagtacgcgg acgccgacct gagcgtggtg gagaagctca aggagatcat catccagaag  1260
gtcgacgaga tctacaaggt ctacggctcg agcgagaagc tgttcgacgc ggacttcgtg  1320
ctggagaagt ccctcaagaa gaacgacgcc gtggtggcca tcatgaagga tctgctcgac  1380
agcgtgaagt cgttcgagaa ctacatcaag gcattctttg gggagggcaa ggagacgaac  1440
cgggacgagt ccttctacgg ggacttcgtg ctcgcgtacg acatcctcct gaaggtcgac  1500
cacatctacg acgcgatccg gaactacgtc acgcagaagc cctacagcaa ggacaagttc  1560
aagctctact tccagaaccc gcagttcatg ggcgggtggg acaaggacaa ggagaccgac  1620
taccgggcca cgatcctgcg gtacgggtcc aagtactacc tcgccatcat ggacaagaag  1680
tacgccaagt gcctccagaa gattgacaag gacgacgtga acgggaacta cgagaagatc  1740
aactacaagc tcctcccggg gcccaacaag atgctgccga aggtgttctt cagcaagaag  1800
tggatggcct actacaaccc ctcggaggac atccagaaga tatacaagaa cggcacgttc  1860
aaaaaggggg acatgttcaa cctgaacgac tgccacaagc tgatcgactt tttcaaggac  1920
agcatcagcc gctacccgaa gtggtcgaac gcctacgact tcaacttctc ggagacggag  1980
aagtacaagg acattgcggg cttctaccgg gaggtggagg agcagggcta caaggtctcc  2040
ttcgagagcg cctccaagaa agaggtggac aagctcgtgg aggagggcaa gctgtacatg  2100
ttccagatct acaacaagga cttctcggac aagtcgcacg gcaccccgaa cctccacacg  2160
atgtacttca agctgctgtt cgacgagaac aaccacgggc agatccgcct cagcggcggg  2220
gcggagctgt tcatgcgccg cgcgtccctc aagaaggagg agctggtcgt gcaccccgcc  2280
aactccccga tcgcgaacaa gaaccccgac aaccccaaga agacaaccac cctctcgtac  2340
gacgtctaca aggacaagcg gttctcggag gaccagtacg agctgcacat cccgatcgcc  2400
atcaacaagt gccccaagaa catcttcaag atcaacaccg aggtgcgggt gctgctcaag  2460
cacgacgaca acccctacgt catcgggatc gaccgcggcg agcggaacct gctctacatc  2520
gtggtcgtgg acgggaaggg gaacatcgtg gagcagtaca gcctgaacga gatcatcaac  2580
aacttcaacg gcatccgcat caagacggac taccacagcc tcctggacaa gaaggagaag  2640
gagcggttcg aggcgcggca gaactggacc tccatcgaga acatcaagga gctgaaggcc  2700
ggctacatca gccaggtcgt gcacaagatc tgcgagctcg tggagaagta cgacgcggtg  2760
atcgcgctgg aggacttgaa cagcgggttc aagaactccc gggtcaaggt cgagaagcag  2820
gtctaccaga agttcgagaa gatgctgatc gacaagctca actacatggt ggacaagaag  2880
tccaacccct gcgccaccgg cggcgccctc aagggctacc agatcaccaa caagttcgag  2940
tccttcaagt cgatgtctac gcagaacggg ttcatttttct acatcccggc gtggctcacc  3000
agcaagatcg acccgagcac gggcttcgtc aacctcctga agaccaagta caccagcatc  3060
gcggacagca agaagttcat ctcctcgttc gaccgcatca tgtacgtccc cgaggaagac  3120
ctgttcgagt tcgccctcga ctacaagaac ttctcccgga cggacgccga ctacatcaaa  3180
aagtggaagc tctacagcta cggcaaccgg atccgcatct tccgcaaccc caagaagaac  3240
aatgtgttcg actgggagga ggtgtgcctg acgagcgcct acaaggagct cttcaacaag  3300
tacggcatca actaccagca aggggacatc cgcgcgctgc tctgcgagca gtccgacaag  3360
gcgttctact cgtcgttcat ggccctgatg agcctcatgc tccagatgcg caacagcatc  3420
accggccgga cggacgtgga cttcctgatc agcccggtca agaacagcga cggcattttc  3480
tacgacagcc ggaactacga ggcccaggag aacgccatcc tccccaagaa cgccgacgcg  3540
aacggcgcct acaacatcgc gcggaaggtg ctgtgggcca tcggccagtt taaaaaggcg  3600
gaggacgaga agctggacaa ggtcaagatc gccatcagca acaaggagtg gctcgagtac  3660
gcgcagacga gcgtgaagca c                                            3681
```

```
SEQ ID NO: 11          moltype = DNA  length = 30
FEATURE                Location/Qualifiers
source                 1..30
                       mol_type = genomic DNA
                       organism = Solanum lycopersicum
SEQUENCE: 11
ggatctaaga agagaagaat taaacaagat                                   30

SEQ ID NO: 12          moltype = DNA  length = 23
FEATURE                Location/Qualifiers
source                 1..23
                       mol_type = genomic DNA
                       organism = Zea mays
SEQUENCE: 12
gatctctata tactgtcact cgc                                          23

SEQ ID NO: 13          moltype = DNA  length = 23
FEATURE                Location/Qualifiers
source                 1..23
                       mol_type = genomic DNA
                       organism = Zea mays
SEQUENCE: 13
gtctcttctt aatataaata ccg                                          23

SEQ ID NO: 14          moltype = DNA  length = 23
FEATURE                Location/Qualifiers
source                 1..23
                       mol_type = genomic DNA
                       organism = Zea mays
SEQUENCE: 14
ggatgatgta aaccttcact cgc                                          23

SEQ ID NO: 15          moltype = DNA  length = 23
FEATURE                Location/Qualifiers
source                 1..23
                       mol_type = genomic DNA
                       organism = Zea mays
SEQUENCE: 15
gccgctgcca atccaccgat ccc                                          23

SEQ ID NO: 16          moltype = DNA  length = 23
FEATURE                Location/Qualifiers
source                 1..23
                       mol_type = genomic DNA
                       organism = Zea mays
SEQUENCE: 16
ctagccgggc aaccggaagc agc                                          23

SEQ ID NO: 17          moltype = DNA  length = 23
FEATURE                Location/Qualifiers
source                 1..23
                       mol_type = genomic DNA
                       organism = Zea mays
SEQUENCE: 17
ctcgtcgtcg gagcggcaat ctg                                          23

SEQ ID NO: 18          moltype = DNA  length = 23
FEATURE                Location/Qualifiers
source                 1..23
                       mol_type = genomic DNA
                       organism = Zea mays
SEQUENCE: 18
ccgctccgac gacgaggaag tag                                          23

SEQ ID NO: 19          moltype = DNA  length = 23
FEATURE                Location/Qualifiers
source                 1..23
                       mol_type = genomic DNA
                       organism = Zea mays
SEQUENCE: 19
ggtaccggat ccgcatccgc gtc                                          23

SEQ ID NO: 20          moltype = DNA  length = 23
FEATURE                Location/Qualifiers
source                 1..23
                       mol_type = genomic DNA
                       organism = Zea mays
```

```
SEQUENCE: 20
cgttgatggc gtagatcacg tcc                                    23

SEQ ID NO: 21          moltype = DNA  length = 23
FEATURE                Location/Qualifiers
source                 1..23
                       mol_type = genomic DNA
                       organism = Zea mays
SEQUENCE: 21
tcatgatcgg cggactgtaa ggc                                    23

SEQ ID NO: 22          moltype = DNA  length = 200
FEATURE                Location/Qualifiers
source                 1..200
                       mol_type = genomic DNA
                       organism = Zea mays
SEQUENCE: 22
cggcgtatgt gccaaaaact tcgtcacaga gagggccata agaaacatgg cccacggccc  60
aatacgaagc accgcgacga agcccaaaca gcagtccgta ggtggagcaa agcgctgggt  120
aatacgcaaa cgttttgtcc caccttgact aatcacaaga gtggagcgta ccttataaac  180
cgagccgcaa gcaccgaatt                                        200

SEQ ID NO: 23          moltype = DNA  length = 23
FEATURE                Location/Qualifiers
source                 1..23
                       mol_type = other DNA
                       note = primer
                       organism = synthetic construct
SEQUENCE: 23
tgagtcgggg tagatctcaa ggc                                    23

SEQ ID NO: 24          moltype = DNA  length = 25
FEATURE                Location/Qualifiers
source                 1..25
                       mol_type = other DNA
                       note = primer
                       organism = synthetic construct
SEQUENCE: 24
tctttgatct gaagcaatgg ctggc                                  25

SEQ ID NO: 25          moltype = DNA  length = 25
FEATURE                Location/Qualifiers
source                 1..25
                       mol_type = other DNA
                       note = primer
                       organism = synthetic construct
SEQUENCE: 25
tgtagcagta gaagagtcca actgg                                  25

SEQ ID NO: 26          moltype = DNA  length = 24
FEATURE                Location/Qualifiers
source                 1..24
                       mol_type = other DNA
                       note = primer
                       organism = synthetic construct
SEQUENCE: 26
tcaccagttg gactcttcta ctgc                                   24

SEQ ID NO: 27          moltype = DNA  length = 24
FEATURE                Location/Qualifiers
source                 1..24
                       mol_type = other DNA
                       note = primer
                       organism = synthetic construct
SEQUENCE: 27
tagaacctct cgatgagcga aacc                                   24

SEQ ID NO: 28          moltype = AA  length = 23
FEATURE                Location/Qualifiers
source                 1..23
                       mol_type = protein
                       organism = Zea mays
SEQUENCE: 28
ALMLIGTLGA LVHGCSLPVF LRF                                    23
```

```
SEQ ID NO: 29          moltype = AA  length = 18
FEATURE                Location/Qualifiers
source                 1..18
                       mol_type = protein
                       organism = Zea mays
SEQUENCE: 29
LVVKYAFYFL VVGAAIWA                                                18

SEQ ID NO: 30          moltype = AA  length = 20
FEATURE                Location/Qualifiers
source                 1..20
                       mol_type = protein
                       organism = Zea mays
SEQUENCE: 30
LIHYMATFVA GFVVGFTAAW                                              20

SEQ ID NO: 31          moltype = AA  length = 23
FEATURE                Location/Qualifiers
source                 1..23
                       mol_type = protein
                       organism = Zea mays
SEQUENCE: 31
LALVTLAVVP LIAVIGGLSA AAL                                          23

SEQ ID NO: 32          moltype = AA  length = 23
FEATURE                Location/Qualifiers
source                 1..23
                       mol_type = protein
                       organism = Zea mays
SEQUENCE: 32
LGGTYFTVFC CYGLLLWYGG HLV                                          23

SEQ ID NO: 33          moltype = AA  length = 23
FEATURE                Location/Qualifiers
source                 1..23
                       mol_type = protein
                       organism = Zea mays
SEQUENCE: 33
GGLAIATMFS VMIGGLALGQ SAP                                          23

SEQ ID NO: 34          moltype = AA  length = 8
FEATURE                Location/Qualifiers
source                 1..8
                       mol_type = protein
                       organism = Zea mays
SEQUENCE: 34
GSSGSGKS                                                           8

SEQ ID NO: 35          moltype = AA  length = 4
FEATURE                Location/Qualifiers
source                 1..4
                       mol_type = protein
                       organism = Zea mays
SEQUENCE: 35
LVSQ                                                               4

SEQ ID NO: 36          moltype = AA  length = 10
FEATURE                Location/Qualifiers
source                 1..10
                       mol_type = protein
                       organism = Zea mays
SEQUENCE: 36
LSGGQKQRIA                                                         10

SEQ ID NO: 37          moltype = AA  length = 7
FEATURE                Location/Qualifiers
source                 1..7
                       mol_type = protein
                       organism = Zea mays
SEQUENCE: 37
ILLLDEA                                                            7

SEQ ID NO: 38          moltype = AA  length = 4
FEATURE                Location/Qualifiers
source                 1..4
                       mol_type = protein
                       organism = Zea mays
```

```
SEQUENCE: 38
SALD                                                                    4

SEQ ID NO: 39          moltype = AA  length = 6
FEATURE                Location/Qualifiers
source                 1..6
                       mol_type = protein
                       organism = Zea mays
SEQUENCE: 39
VIAHRL                                                                  6

SEQ ID NO: 40          moltype = AA  length = 23
FEATURE                Location/Qualifiers
source                 1..23
                       mol_type = protein
                       organism = Zea mays
SEQUENCE: 40
MVCGSFSAIF AYILSAVLSV YYA                                               23

SEQ ID NO: 41          moltype = AA  length = 23
FEATURE                Location/Qualifiers
source                 1..23
                       mol_type = protein
                       organism = Zea mays
SEQUENCE: 41
YCYLLIGMSS AALLFNTVQH VFW                                               23

SEQ ID NO: 42          moltype = AA  length = 23
FEATURE                Location/Qualifiers
source                 1..23
                       mol_type = protein
                       organism = Zea mays
SEQUENCE: 42
ISVIVQNSAL MLVACTAGFV LQW                                               23

SEQ ID NO: 43          moltype = AA  length = 23
FEATURE                Location/Qualifiers
source                 1..23
                       mol_type = protein
                       organism = Zea mays
SEQUENCE: 43
LALVLLAVFP LVVGATVLQK MFM                                               23

SEQ ID NO: 44          moltype = AA  length = 23
FEATURE                Location/Qualifiers
source                 1..23
                       mol_type = protein
                       organism = Zea mays
SEQUENCE: 44
YGVAQFLLYA SYALGLWYAA WLV                                               23

SEQ ID NO: 45          moltype = AA  length = 23
FEATURE                Location/Qualifiers
source                 1..23
                       mol_type = protein
                       organism = Zea mays
SEQUENCE: 45
VFMVLMVSAN GAAETLTLAP DFI                                               23

SEQ ID NO: 46          moltype = AA  length = 8
FEATURE                Location/Qualifiers
source                 1..8
                       mol_type = protein
                       organism = Zea mays
SEQUENCE: 46
GPSGCGKS                                                                8

SEQ ID NO: 47          moltype = AA  length = 4
FEATURE                Location/Qualifiers
source                 1..4
                       mol_type = protein
                       organism = Zea mays
SEQUENCE: 47
VVPQ                                                                    4

SEQ ID NO: 48          moltype = AA  length = 10
FEATURE                Location/Qualifiers
```

```
source                1..10
                      mol_type = protein
                      organism = Zea mays
SEQUENCE: 48
LSGGQRQRIA                                                    10

SEQ ID NO: 49         moltype = AA  length = 7
FEATURE               Location/Qualifiers
source                1..7
                      mol_type = protein
                      organism = Zea mays
SEQUENCE: 49
IVLLDEA                                                       7

SEQ ID NO: 50         moltype = AA  length = 4
FEATURE               Location/Qualifiers
source                1..4
                      mol_type = protein
                      organism = Zea mays
SEQUENCE: 50
SALD                                                          4

SEQ ID NO: 51         moltype = AA  length = 6
FEATURE               Location/Qualifiers
source                1..6
                      mol_type = protein
                      organism = Zea mays
SEQUENCE: 51
VVAHRL                                                        6

SEQ ID NO: 52         moltype = AA  length = 1377
FEATURE               Location/Qualifiers
source                1..1377
                      mol_type = protein
                      note = predicted protein sequence after editing
                      organism = synthetic construct
SEQUENCE: 52
MSSSDPEEIR ARVVVLGSPH ADGGDEWARP ELEAFHLPSP AHQPPGFLAG QPEEQPTLPA  60
PAGRSSSSSN TPTTSAGGGA APPPPSSPPP PPASLETEQP PNARPASAGA NDSKKPTPPA  120
ALRDLFRFAD GLDCALMLIG TLGALVHGCS LPVFLRFFAD LVDSFGSHAD DPDTMVRLVV  180
KYAFYFLVVG AAIWASSWAE ISCWMWTGER QSTRMRIRYL DAALRQDVSF FDTDVRASDV  240
IYAINADAVV VQDAISEKLG NLIHYMATFV AGFVVGFTAA WQLALVTLAV VPLIAVIGGL  300
SAAALAKLSS RSQDALSGAS GIAEQALAQI RIVQAFVGEE REMRAYSAAL AVAQRIGYRS  360
GFAKGLGLGG TYFTVFCCYG LLLWYGGHLV RAQHTNGGLA IATMFSVMIG GLALGQSAPS  420
MAAFAKARVA AAKIFRIIDH RPGISSRDGA EPESVTGRVE MRGVDFAYPS RPDVPILRGF  480
SLSVPAGKTI ALVGSSGSGK STVVSLIERF YDPSAGQILL DGHDLRSLKL RWLRRQIGLV  540
SQEPALFATS IRENLLLGRD SQSATLAEME EAARVANAHS FIIKLPDGYD TQVGERGLQL  600
SGGQKQRIAI ARAMLKNPAI LLLDEATSAL DSESEKLVQE ALDRFMIGRT TLVIAHRLST  660
IRKADVVAVL QGGAVSEMGA HDELMAKGEN GTYAKLIRMQ EQAHEAALVN ARRSSARPSS  720
ARNSVSSPIM TRNSSYGRSP YSRRLSDFST SDFTLSIHDP HHHHRTMADK QLAFRAGASS  780
FLRLARMNSP EWAYALAGSI GSMVCGSFSA IFAYILSAVL SVYYAPDPRY MKREIAKYCY  840
LLIGMSSAAL LFNTVQHVFW DTVGENLTKR VREKMFAAVL RNEIAWFDAD ENASARVAAR  900
LALDAQNVRS AIGDRISVIV QNSALMLVAC TAGFVLQWRL ALVLLAVFPL VVGATVLQKM  960
FMKGFSGDLE AAHARATQIA GEAVANLRTV AAFNAERKIT GLFEANLRGP LRRCFWKGQI  1020
AGSGYGVAQF LLYASYALGL WYAAWLVKHG VSDFSRTIRV FMVLMVSANG AAETLTLAPD  1080
FIKGGRAMRS VFETIDRKTE VEPDDVDAAP VPERPRGEVE LKHVDFSYPS RPDIQVFRDL  1140
SLRARAGKTL ALVGPSGCGK SSVLALVQRF YEPTSGRVLL DGKDVRKYNL RALRRVVAVV  1200
PQEPFLFAAS IHENIAYGRE GATEAEVVEA AAQANAHRFI AALPEGYRTQ VGERGVQLSG  1260
GQRQRIAIAR ALVKQAAIVL LDEATSALDA ESERCVQEAL ERAGSGRTTI VVAHRLATVR  1320
GAHTIAVIDD GKVAEQGSHS HLLKHHPDGC YARMLQLQRL TGAAAGPGPS TSCNGAA     1377

SEQ ID NO: 53         moltype = AA  length = 436
FEATURE               Location/Qualifiers
source                1..436
                      mol_type = protein
                      note = predicted protein sequence after editing
                      organism = synthetic construct
SEQUENCE: 53
MSSSDPEEIR ARVVVLGSPH ADGGDEWARP ELEAFHLPSP AHQPPGFLAG QPEAAEQPTL  60
PAPAGRSSSS SNTPTTSAGG GAAPPPPSSP PPPPASLETE QPPNARPASA GANDSKKPTP  120
PAALRDLFRF ADGLDCALML IGTLGALVHG CSLPVFLRFF ADLVDSFGSH ADDPDTMVRL  180
VVKYAFYFLV VGAAIWASSW AEISCWMWTG ERQSGPRAVG AEHGRVRQGA CGGCQDLPHH  240
RPQAGHLLAR RRGARVGDGA GGDAGRGLRV PVAAGRPHPA RLLAERARRE DHRAGGQLRL  300
REEHGGFAHR EVLRPQRRAN PAGRARPQVA EAAMAAAADR AGEPGAGAVR DEHQGEPAAG  360
AGQPERDAGG DGGGGQGGQR PLLHHQTPRR LRHAGWGARP AALRWAEAAH RHRPRHAQEP  420
RHPAAGRGHQ RAGLRV                                             436

SEQ ID NO: 54         moltype = AA  length = 1210
FEATURE               Location/Qualifiers
```

```
source                  1..1210
                        mol_type = protein
                        note = predicted protein sequence after editing
                        organism = synthetic construct
SEQUENCE: 54
MSSSDPEEIR ARVVVLGSPH ADGGDEWARP ELEAFHLPSP AHQPPGFLAG QPEAAEQPTL  60
PAPAGRSSSS SNTPTTSAGG GAAPPPPSSP PPPPASLETE QPPNARPASA GANDSKKPTP  120
PAALRDLFRF ADGLDCALML IGTLGALVHG CSLPVFLRFF ADLVDSFGSH ADDPDTMVRL  180
VVKYAFYFLV VGAAIWASSW AEISCWMWTG ERQSLLWYGG HLVRAQHTNG GLAIATMFSV  240
MIGGLALGQS APSMAAFAKA RVAAAKIFRI IDHRPGISSR DGAEPESVTG RVEMRGVDFA  300
YPSRPDVPIL RGFSLSVPAG KTIALVGSSG SGKSTVVSLI ERFYDPSAGQ ILLDGHDLRS  360
LKLRWLRRQI GLVSQEPALF ATSIRENLLL GRDSQSATLA EMEEAARVAN AHSFIIKLPD  420
GYDTQVGERG LQLSGGQKQR IAIARAMLKN PAILLLDEAT SALDSESEKL VQEALDRFMI  480
GRTTLVIAHR LSTIRKADVV AVLQGGAVSE MGAHDELMAK GENGTYAKLI RMQEQAHEAA  540
LVNARRSSAR PSSARNSVSS PIMTRNSSYG RSPYSRRLSD FSTSDFTLSI HDPHHHHRTM  600
ADKQLAFRAG ASSFLRLARM NSPEWAYALA GSIGSMVCGS FSAIFAYILS AVLSVYYAPD  660
PRYMKREIAK YCYLLIGMSS AALLFNTVQH VFWDTVGENL TKRVREKMFA AVLRNEIAWF  720
DADENASARV AARLALDAQN VRSAIGDRIS VIVQNSALML VACTAGFVLQ WRLALVLLAV  780
FPLVVGATVL QKMFMKGFSG DLEAAHARAT QIAGEAVANL RTVAAFNAER KITGLFEANL  840
RGPLRRCFWK GQIAGSGYGV AQFLLYASYA LGLWYAAWLV KHGVSDFSRT IRVFMVLMVS  900
ANGAAETLTL APDFIKGGRA MRSVFETIDR KTEVEPDDVD AAPVPERPRG EVELKHVDFS  960
YPSRPDIQVF RDLSLRARAG KTLALVGPSG CGKSSVLALV QRFYEPTSGR VLLDGKDVRK  1020
YNLRALRRVV AVVPQEPFLF AASIHENIAY GREGATEAEV VEAAAQANAH RFIAALPEGY  1080
RTQVGERGVQ LSGGQRQRIA IARALVKQAA IVLLDEATSA LDAESERCVQ EALERAGSGR  1140
TTIVVAHRLA TVRGAHTIAV IDDGKVAEQG SHSHLLKHHP DGCYARMLQL QRLTGAAAGP  1200
GPSTSCNGAA                                                        1210

SEQ ID NO: 55           moltype = DNA  length = 80
FEATURE                 Location/Qualifiers
source                  1..80
                        mol_type = other DNA
                        organism = synthetic construct
SEQUENCE: 55
cggcaccctc ggcgcgctcg tccacggctg ctcgctcccc accacaccac tctctccttc  60
tcctgctcct cggcccgccc                                             80

SEQ ID NO: 56           moltype = DNA  length = 356
FEATURE                 Location/Qualifiers
source                  1..356
                        mol_type = other DNA
                        organism = synthetic construct
SEQUENCE: 56
agagatctct tgctggatgt ggaccggcga gcggcagtcg tggggttcac ggccgcgtgg  60
cagctggcgc tggtcacgct ggccgtggtg ccgctcatcg ccgtcatcgg cgggctgagc  120
gccgccgcgc tcgccaagct ctcgtcccgc agccaggacg cgctctccgg cgccagcggc  180
atcgcggagc aggcgctcgc gcagatacgg atcgtgcagg cgttcgtcgg cgaggagcgc  240
gagatgcggg cctactcggc ggcgctggcc gtggcgcaga ggatcggcta ccgcagcggc  300
ttcgccaagg gtctcgctct ccttctcctg ctcctcggcc cgcccgtcgt cattgc      356

SEQ ID NO: 57           moltype = DNA  length = 80
FEATURE                 Location/Qualifiers
source                  1..80
                        mol_type = other DNA
                        organism = synthetic construct
SEQUENCE: 57
cctcctcctc cttcttcgcc tccccctccg ccggcttctc cggtacctgg acgcggcgct  60
gcggcaggac gtgtccttct                                             80

SEQ ID NO: 58           moltype = DNA  length = 80
FEATURE                 Location/Qualifiers
source                  1..80
                        mol_type = other DNA
                        organism = synthetic construct
SEQUENCE: 58
tctcttgctg gatgtggacc ggcgagcggc agtcgacgcg cggatccggt acctggacgc  60
ggcgctgcgg caggacgtgt                                             80

SEQ ID NO: 59           moltype = DNA  length = 474
FEATURE                 Location/Qualifiers
source                  1..474
                        mol_type = other DNA
                        organism = synthetic construct
SEQUENCE: 59
gagatctctt gctggatgtg gaccggcgag cggcagtcga tccggtacct ggacgcggcg  60
ctgcggcagg acgtgtcctt cttcgacacc gacgtgcggg cctcgagccg ccgcgctcgc  120
caagctctcg tcccgcagcc aggacgcgct ctccggcgcc agcggcatcg cggagcaggc  180
gctcgcgcag atacggatcg tgcaggcgtt cgtcggcgag gagcgcgaga tgcgggccta  240
ctcggcggcg ctggccgtgg cgcagaggat cggctaccgc agcggcttcg ccaagggtct  300
cggcctcggc ggcacctact tcaccgtctt ctgctgctac gggctcctgc tctggtacgg  360
```

```
cggccacctc gtgcgcgccc agcacaccaa cggcgggctc gccatcgcca ccatgttctc  420
cgtcatgatc ggcgccacca caccactctc tccttctcct gctcctcggc ccgc        474

SEQ ID NO: 60          moltype = AA  length = 376
FEATURE                Location/Qualifiers
source                 1..376
                       mol_type = protein
                       organism = synthetic construct
SEQUENCE: 60
MSSSDPEEIR ARVVVLGSPH ADGGDEWARP ELEAFHLPSP AHQPPGFLAG QPEAAEQPTL  60
PAPAGRSSSS SNTPTTSAGG GAAPPPPSSP PPPPASLETE QPPNARPASA GANDSKKPTP  120
PAALRDLFRF ADGLDCALML IGTLGALVHG CSLPGPRAVG AEHGRVRQGA CGGCQDLPHH  180
RPQAGHLLAR RRGARVGDGA GGDAGRGLRV PVAAGRPHPA RLLAERARRE DHRAGGQLRL  240
REEHGGFAHR EVLRPQRRAN PAGRARPQVA EAAMAAAADR AGEPGAGAVR DEHQGEPAAG  300
AGQPERDAGG DGGGGQGGQR PLLHHQTPRR LRHAGWGARP AALRWAEAAH RHRPRHAQEP  360
RHPAAGRGHQ RAGLRV                                                 376

SEQ ID NO: 61          moltype = AA  length = 239
FEATURE                Location/Qualifiers
source                 1..239
                       mol_type = protein
                       organism = synthetic construct
SEQUENCE: 61
MSSSDPEEIR ARVVVLGSPH ADGGDEWARP ELEAFHLPSP AHQPPGFLAG QPEAAEQPTL  60
PAPAGRSSSS SNTPTTSAGG GAAPPPPSSP PPPPASLETE QPPNARPASA GANDSKKPTP  120
PAALRDLFRF ADGLDCALML IGTLGALVHG CSLPVFLRFF ADLVDSFGSH ADDPDTMVRL  180
VVKYAFYFLV VGAAIWASSW AEISCWMWTG ERQSWGSRPR GSWRWSRWPW CRSSPSSAG   239

SEQ ID NO: 62          moltype = AA  length = 513
FEATURE                Location/Qualifiers
source                 1..513
                       mol_type = protein
                       organism = synthetic construct
SEQUENCE: 62
MSSSDPEEIR ARVVVLGSPH ADGGDEWARP ELEAFHLPSP AHQPPGFLAG QPEAAEQPTL  60
PAPAGRSSSS SNTPTTSAGG GAAPPPPSSP PPPPASPVPG RGAAAGRVLL RHRRAGLGRD  120
LRHQRGRSGG AGRHQREAGQ PHPLHGHLRG RLRRGVHGRV AAGAGHAGRG AAHRRHRRAE  180
RRRARQALVP QPGRALRRQR HRGAGARADT DRAGVRRRGA RDAGLLGGAG RGAEDRLPQR  240
LRQGSRPRRH LLHRLLLLRA PALVRRPPRA RPAHQRRARH RHHVLRHDRR TGPRAVGAEH  300
GRVRQGACGG CQDLPHHRPQ AGHLLARRRG ARVGDGAGGD AGRGLRVPVA AGRPHPARLL  360
AERARREDHR AGGQLRLREE HGGFAHREVL RPQRRANPAG RARPQVAEAA MAAAADRAGE  420
PGAGAVRDEH QGEPAAGAGQ PERDAGGDGG GGQGGQRPLL HHQTPRRLRH AGWGARPAAL  480
RWAEAAHRHR PRHAQEPRHP AAGRGHQRAG LRV                              513

SEQ ID NO: 63          moltype = AA  length = 240
FEATURE                Location/Qualifiers
source                 1..240
                       mol_type = protein
                       organism = synthetic construct
SEQUENCE: 63
MSSSDPEEIR ARVVVLGSPH ADGGDEWARP ELEAFHLPSP AHQPPGFLAG QPEAAEQPTL  60
PAPAGRSSSS SNTPTTSAGG GAAPPPPSSP PPPPASLETE QPPNARPASA GANDSKKPTP  120
PAALRDLFRF ADGLDCALML IGTLGALVHG CSLPVFLRFF ADLVDSFGSH ADDPDTMVRL  180
VVKYAFYFLV VGAAIWASSW AEISCWMWTG ERQSTRGSGT WTRRCGRTCP SSTPTCGPRT  240

SEQ ID NO: 64          moltype = AA  length = 980
FEATURE                Location/Qualifiers
source                 1..980
                       mol_type = protein
                       organism = synthetic construct
SEQUENCE: 64
MSSSDPEEIR ARVVVLGSPH ADGGDEWARP ELEAFHLPSP AHQPPGFLAG QPEAAEQPTL  60
PAPAGRSSSS SNTPTTSAGG GAAPPPPSSP PPPPASLETE QPPNARPASA GANDSKKPTP  120
PAALRDLFRF ADGLDCALML IGTLGALVHG CSLPVFLRFF ADLVDSFGSH ADDPDTMVRL  180
VVKYAFYFLV VGAAIWASSW AEISCWMWTG ERQSIRYLDA ALRQDVSFFD TDVRASSRRA  240
RQALVPQPGR ALRRQRHRGA GARADTDRAG VRRRGARDAG LLGGAGRGAE DRLPQRLRQG  300
SRPRRHLLHR LLLLRAPALV RRPPRARPAH QRRARHRHHV LRHDRRALGQ SAPSMAAFAK  360
ARVAAAKIFR IIDHRPGISS RDGAEPESVT GRVEMRGVDF AYPSRPDVPI LRGFSLSVPA  420
GKTIALVGSS GSGKSTVVSL IERFYDPSAG QILLDGHDLR SLKLRWLRRQ IGLVSQEPAL  480
FATSIRENLL LGRDSQSATL AEMEEAARVA NAHSFIIKLP DGYDTQVGER GLQLSGGQKQ  540
RIAIARAMLK NPAILLLDEA TSALDSESEK LVQEALDRFM IGRTTLVIAH RLSTIRKADV  600
VAVLQQGAVS EMGAHDELMA KGENGTYAKL IRMQEQAHEA ALVNARRSSA RPSSARNSVS  660
SPIMTRNSSY GRSPYSRRLS DFSTSDFTLS IHDPHHHHRT MADKQLAFRA GASSFLRLAR  720
MNSPEWAYAL AGSIGSMVCG SFSAIFAYIL SAVLSVYYAP DPRYMKREIA KYCYLLIGMS  780
SAALLFNTVQ HVFWDTVGEN LTKRVREKMF AAVLRNEIAW FDADENASAR VAARLALDAQ  840
NVRSAIGDRI SVIVQNSALM LVACTAGFVL QWRLALVLLA VFPLVVGATV LQKMFMKGFS  900
GTWRPRTPGR RRSRARPWPT CAPWPRSTRS ARSRGCSRPT CAARSGAASG RGRSPAAATA  960
WRSSCCTRPT RWGCGTRRGW                                             980
```